(12) United States Patent
Tao et al.

(10) Patent No.: US 10,738,033 B2
(45) Date of Patent: Aug. 11, 2020

(54) TRK INHIBITION

(71) Applicant: NantBio, Inc., Culver City, CA (US)

(72) Inventors: Chunlin Tao, Newport Coast, CA (US);
Qinwei Wang, Alhambra, CA (US);
Sharif Asad, Lake Forest, CA (US);
Paul Weingarten, Anaheim, CA (US);
Sherry Ci, San Marino, CA (US)

(73) Assignee: NANTBIO, INC., Culver City, CA (US)

( * ) Notice: Subject to any disclaimer, the term of this patent is extended or adjusted under 35 U.S.C. 154(b) by 0 days.

(21) Appl. No.: 15/992,989

(22) Filed: May 30, 2018

(65) Prior Publication Data

US 2018/0346451 A1 Dec. 6, 2018

Related U.S. Application Data

(60) Provisional application No. 62/513,127, filed on May 31, 2017.

(51) Int. Cl.
| C07D 403/14 | (2006.01) |
| A61P 35/00 | (2006.01) |
| A61P 29/00 | (2006.01) |
| A61P 25/28 | (2006.01) |
| A61K 31/4155 | (2006.01) |

(52) U.S. Cl.
CPC ........ *C07D 403/14* (2013.01); *A61K 31/4155* (2013.01); *A61P 25/28* (2018.01); *A61P 29/00* (2018.01); *A61P 35/00* (2018.01)

(58) Field of Classification Search
CPC .................................................. C07D 403/14
See application file for complete search history.

(56) References Cited

U.S. PATENT DOCUMENTS

| 5,916,596 | A | 6/1999 | Desai et al. |
| 6,506,405 | B1 | 1/2003 | Desai et al. |
| 6,537,579 | B1 | 3/2003 | Desai et al. |
| 9,458,137 | B2 | 10/2016 | Tao et al. |
| 9,670,207 | B2 | 6/2017 | Sasmal et al. |
| 2012/0172361 | A1 | 7/2012 | Tao et al. |
| 2012/0238576 | A1 | 9/2012 | Tao et al. |
| 2013/0023497 | A1 | 1/2013 | Tao et al. |
| 2016/0168156 | A1 | 6/2016 | Kim et al. |

OTHER PUBLICATIONS

Allwein, Shawn P., et al., "Efficient synthesis of chiral phenethylamines: preparation, asymmetric hydrogenation, and mild deprotection of ene-trifluoroacetamides." Tetrahedron letters 47.36 (2006): 6409-6412.
Bishop, Justin A., et al., "Most non-parotid "acinic cell carcinomas" represent mammary analogue secretory carcinomas." The American journal of surgical pathology 37.7 (2013): 1053.
Brenca, Monica, et al., "Transcriptome sequencing identifies ETV6-NTRK3 as a gene fusion involved in GIST." The Journal of Pathology 238.4 (2016): 543-549.
Delafoy, Laure, et al., "Role of nerve growth factor in the trinitrobenzene sulfonic acid-induced colonic hypersensitivity." Pain 105.3 (2003): 489-497.
Di Mola, F. F., et al., "Nerve growth factor and Trk high affinity receptor (TrkA) gene expression in inflammatory bowel disease." Gut 46.5 (2000): 670-678.
Doebele, R. C., et al., An oncogenic NTRK Fusion in a patient with soft-tissue sarcoma with response to the tropomyosin-related kinase inhibitor LOXO-101. Cancer Discov. 2015; 5: 1049-1057.
Dou, Ying-Chun, et al., "Increased nerve growth factor and its receptors in atopic dermatitis: an immunohistochemical study." Archives of dermatological research 298.1 (2006): 31-37.
Freund-Michei, V., and N. Frossard. "The nerve growth factor and its receptors in airway inflammatory diseases." Pharmacology & Therapeutics 117.1 (2008): 52-76.
Hu, Vivian Y., et al., "Decrease in bladder overactivity with REN1820 in rats with cyclophosphamide induced cystitis." The Journal of Urology 173.3 (2005): 1016-1021.
Huang, Eric J., and Louis F. Reichardt. "Trk receptors: roles in neuronal signal transduction." Annual review of biochemistry 72.1 (2003): 609-642.
Jaggar, S. I., et al., "Inflammation of the rat urinary bladder is associated with a referred thermal hyperalgesia which is nerve growth factor dependent." British journal of anaesthesia 83.3 (1999): 442-448.
Lamb, K., et al., "Nerve growth factor and gastric hyperalgesia in the rat." Neurogastroenterology & Motility 15.4 (2003): 355-361.
Ma, Qing-Ping, and Clifford J. Woolf, "The progressive tactile hyperalgesia induced by peripheral inflammation is nerve growth factor dependent." Neuroreport 8.4 (1997): 807-810.

(Continued)

*Primary Examiner* — Brian E McDowell
(74) *Attorney, Agent, or Firm* — Mintz, Levin, Cohn, Ferris, Glovsky and Popeo, P.C.

(57) ABSTRACT

The present invention relates to the use of substituted pyrimidine derivatives to modulate tropomyosin-related kinase (Trk) family protein kinase, and the use of the substituted pyrimidine derivatives for the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA. The present invention also provides compounds of the formula:

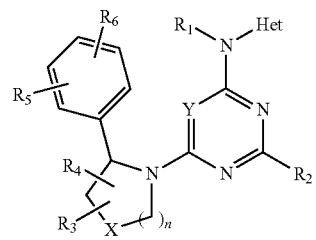

as defined herein.

7 Claims, No Drawings

(56) References Cited

OTHER PUBLICATIONS

Maryanoff, Bruce E., et al., "Pyrroloisoquinoline antidepressants. 2. In-depth exploration of structure-activity relationships." Journal of medicinal chemistry 30.8 (1987): 1433-1454.
Maryanoff, Bruce E., et al., "Pyrroloisoquinoline antidepressants. 3. A focus on serotonin." Journal of medicinal chemistry 33.10 (1990): 2793-2797.
McMahon, Stephen B., et al., "The biological effects of endogenous nerve growth factor on adult sensory neurons revealed by a trkA-IgG fusion molecule." Nature medicine 1.8 (1995): 774.
Patapoutian, Ardem, and Louis F. Reichardt. "Trk receptors: mediators of neurotrophin action." Current opinion in neurobiology 11.3 (2001): 272-280.
Prasad, Manju L., et al., "NTRK fusion oncogenes in pediatric papillary thyroid carcinoma in northeast United States." Cancer 122.7 (2016): 1097-1107.
Raychaudhuri, Siba P., et al, "K252a, a high-affinity nerve growth factor receptor blocker, improves psoriasis: an in vivo study using the severe combined immunodeficient mouse-human skin model." Journal of investigative dermatology 122.3 (2004): 812-819.
Shelton, David L., et al., "Nerve growth factor mediates hyperalgesia and cachexia in auto-immune arthritis." Pain 116.1-2 (2005): 8-16.
Sohrabji, Farida, and Danielle K. Lewis. "Estrogen-BDNF interactions: implications for neurodegenerative diseases." Frontiers in neuroendocrinology 27.4 (2006): 404-414.
Vaishnavi, Aria, et al., "TRKing down an old oncogene in a new era of targeted therapy." Cancer discovery 5.1 (2015): 25-34.
Whitesell, Luke, et al., "The stress response: implications for the clinical development of hsp90 inhibitors." Current cancer drug targets 3.5 (2003): 349-358.
Woolf, Clifford J., et al., "Nerve growth factor contributes to the generation of inflammatory sensory hypersensitivity." Neuroscience 62.2 (1994): 327-331.
Zahn, Peter K., et al., "Effect of blockade of nerve growth factor and tumor necrosis factor on pain behaviors after plantar incision." The Journal of Pain 5.3 (2004): 157-163.

TRK INHIBITION

CROSS REFERENCE TO RELATED APPLICATION

This application claims the benefit of U.S. Provisional Patent Application No. 62/513,127, filed on May 31, 2017, the disclosure of which is incorporated by reference in its entirety.

FIELD OF THE INVENTION

The present invention relates to the use of substituted pyrimidine derivatives to modulate tropomyosin-related kinase (Trk) family protein kinase, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

The tropomyosin receptor kinase (Trk) receptors are a family of tyrosine kinases that regulates synaptic strength and plasticity in the mammalian nervous system (Huang E J, Reichardt L F (2003). Annu. Rev. Biochem. 72: 609-642) (incorporated herein by reference). The Trk receptor family comprises 3 transmembrane proteins referred to as TrkA, TrkB and TrkC receptors that are encoded by the NTRK1, NTRK2 and NTRK3 genes, respectively. These receptor tyrosine kinases are expressed in human neuronal tissue and play an essential role in the physiology of development and function of the nervous system through activation by neurotrophins (Patapoutian, A. et al. (2001) Current Opinion in Neurobiology 11: 272-280) (incorporated herein by reference).

Trk kinase fusions have been described in multiple cancers including colorectal cancer, lung adenocarcinoma, salivary gland cancer, head and neck squamous cell cancer, glioblastoma multiforme, and thyroid cancer (Vaishnavi A, Le A T, Doebele R C (2015). Cancer Discov. 5 (1): 25-34; Bishop J A et al. J Surg Pathol. 2013 37(7):1053-7; Prasad M L et al. Cancer, 2016 Jan. 19; brenca M. et al. J Pathol 2016, 238(4): 543-9) (each of which is incorporated herein by reference). Trk kinase fusions have further fueled the development of pan-Trk inhibitor drugs for use in oncology. In accordance with the potential for Trk fusions to be used as molecular targets in cancer, Trk inhibition has been shown in vitro to inhibit the proliferation of cell lines expressing Trk fusions. Recent clinical study details strong clinical response to a Trk inhibitor by a sarcoma patient, and thus the patient could be rationally treated with a pan-Trk inhibitor drug (Robert C. Doebert et al. (2015) Cancer Discov. 5(10): 1049-1057) (Incorporated herein by reference).

Inhibitors of the Trk/neutrophin pathway have been demonstrated to be highly effective in numerous pre-clinical animal models of pain. Antagonistic NGF and TrkA antibodies have been shown to be efficacious in inflammatory and neuropathic pain animal models and in human clinical trials (Woolf, C. J. et al. (1994) Neuroscience 62, 327-331; Zahn, P. K. et al. (2004) J Pain 5, 157-163; McMahon5 S. B. et al., (1995) Nat. Med. 1, 774-780; Ma, Q. P. and Woolf, C. J. (1997) Neuroreport 8, 807-810; Shelton, D. L. et al. (2005) Pain 116, 8-16; Delafoy, L. et al. (2003) Pain 105, 489-497; Lamb, K. et al (2003) Neurogastroenterol Motil 15, 355-361; and Jaggar, S. I. et al. (199) Br. J. Anaesth. 83, 442-448) (each of which is incorporated herein by reference). Also promising is the utility of Trk inhibitors in the treatment of inflammatory lung diseases such as asthma (Freund-Michel, V; et al., Pharmacology & Therapeutics (2008), 117(1), 52-76) (incorporated herein by reference), interstitial cystitis (Hu Vivian Y; et. al., J of Urology (2005), 173(3), 1016-21) (incorporated herein by reference), inflammatory bowel disease including ulcerative colitis and Crohn's disease (Di Mola, F. F., et al., Gut (2000), 46(5), 670-678) (incorporated herein by reference) and inflammatory skin diseases such as atopic dermatitis (Dou, Y. C., et. Al., Archives of Dermatological Research (2006), 298(1), 31-37) (incorporated herein by reference), eczema and psoriasis (Raychaudhuri, S. P. et. al., J of Investigative Dermatology (2004), 122(3), 812-819). Modulation of the neutrophin/Trk pathway also has been shown to have an effect in the etiology of neurodegenerative diseases including multiple sclerosis, Parkinson's disease and Alzheimer's disease (Sohrabji, et. al, Neuroendocrinology (2006), 27(4), 404-414) (incorporated herein by reference).

Despite this promising research, a need exists for compounds acting as Trk kinase mediators or inhibitors.

SUMMARY OF THE INVENTION

The present invention provides an agent comprising substituted pyrimidine derivatives as described in formula (I), pharmaceutically-acceptable formulations thereof, methods for making novel compounds and compositions for using the compounds. The compounds and compositions comprising the compounds in formula (I) are useful as a Trk kinase mediator of NGF driven biological responses, an inhibitor of TrkA and other Trk kinases. The invention involves use of the compounds as Trk kinase inhibitors for the treatment of a variety of diseases associated with Trk kinases, including multiple types of cancers, acute and chronic pain, inflammation, neurodegenerative diseases, certain infectious diseases, respiratory distress, and others.

DETAILED DESCRIPTION OF THE INVENTION

The present invention is related to compounds having general Formula (I)

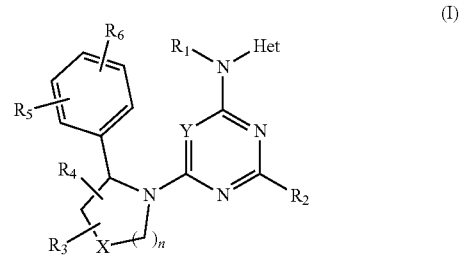

(I)

or a pharmaceutically acceptable salt thereof, wherein:
$R_1$ represents hydrogen, $C_1$-$C_4$ alkyl.
$R_2$ represents hydrogen, $NH_2$ and $C_1$-$C_4$ alkyl.
$R_3$ and $R_4$ respectively represent hydrogen, F, CN, oxo, $C_1$-$C_4$ alkyl, cycloalkyl, $C_1$-$C_6$ alkoxy, $C_2$-$C_4$ alkenyl, $C_2$-$C_4$ alkynyl.
$R_5$ and $R_6$ respectively represent hydrogen, F, Cl, Br, I, CN, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, $CON(R_7)R_8$.

$R_7$ and $R_8$ are independently selected from hydrogen, $C_1$-$C_4$ alkyl, $C_2$-$C_6$ alkenyl, $C_2$-$C_6$ alkynyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy.

n=0-3.

X represents $CH_2$, NR, O or S. R represents hydrogen, $C_1$-$C_4$ alkyl, cycloalkyl, $C_1$-$C_6$ alkoxy, $C_2$-$C_4$ alkenyl, $C_2$-$C_4$ alkynyl.

Y represents N and $CR_9$. $R_9$ is selected from hydrogen, F, Cl, Br, I, CN, $NO_2$, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, $N(R_7)R_8$ and $CON(R_7)R_8$.

Het represents $C_2$-$C_8$ heteroaryl, which is substituted with from 0 to 4 substituents independently chosen from:
(1) halogen, hydroxy, amino, amide, cyano, —COOH, —$SO_2NH_2$, oxo, nitro and alkoxycarbonyl;
(2) $CON(R_7)R_8$, $N(R_7)R_8$; and
(3) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl) amino$C_0$-$C_4$alkyl, (4- to 7-membered heterocycle) $C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term 'cycloalkyl" herein alone or as part of another group refers to fully saturated and partially unsaturated hydrocarbon rings of 3 to 9, or 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2$NR'R", —C(=O) NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term 'alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Alkoxy groups for use in the present invention may have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Alkoxy and alkylthio groups for use in present invention may be those in which an alkyl group is attached via the heteroatom bridge. Alkylthio groups for use in the present invention may have from 1 to 8 carbon atoms. Examples of such groups include the methylthio, ethylthio, n-propythiol, n-butylthiol, and like.

The term "oxo," as used herein, refers to a keto (C=O) group. An oxo group that is a substituent of a nonaromatic carbon atom results in a conversion of —$CH_2$— to —C(=O)—.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_1$-$C_6$ alkyl group, cycloalkyl, aryl, or heteroaryl.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)m (m=O, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —NH$_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula (SO$_2$)-alkyl, in which the sulfur atom is the point of attachment. Alkylsulfonyl groups for use in the present invention may include C$_1$-C$_6$ alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (0, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The term "heterocycle" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (for example lower alkyl), heterocycloalkyl, heteroaryl, alkoxy (for example lower alkoxy), nitro, monoalkylamino (for example a lower alkylamino), dialkylamino (for example an alkylamino), cyano, halo, haloalkyl (for example trifluoromethyl), alkanoyl, aminocarbonyl, monoalkylaminocarbonyl, dialkylaminocarbonyl, alkyl amido (for example lower alkyl amido), alkoxyalkyl (for example a lower alkoxy; lower alkyl), alkoxycarbonyl (for example a lower alkoxycarbonyl), alkylcarbonyloxy (for example a lower alkylcarbonyloxy) and aryl (for example phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" or "heterocycloalkyl" groups include piperazine, piperidine, morpholine, thiomorpholine, pyrrolidine, imidazolidine and thiazolide.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (for example a carbon or nitrogen atom) that is a ring member.

The term "optionally substituted" indicates that the referenced aryl or heterocyclyl or other group may be substituted at one or more substitutable positions by one or more groups independently selected from alkyl (for example lower alkyl), alkoxy (for example lower alkoxy), nitro, monoalkylamino (for example with one to six carbons), dialkylamino (for example with one to six carbons), cyano, halo, haloalkyl (for example trifluoromethyl), alkanoyl, aminocarbonyl, monoalkylaminocarbonyl, dialkylaminocarbonyl, alkyl amido (for example lower alkyl amido), alkoxyalkyl (for example a lower alkoxy and lower alkyl), alkoxycarbonyl (for example a lower alkoxycarbonyl), alkylcarbonyloxy (for example a lower alkylcarbonyloxy) and aryl (for example phenyl), said aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("-") that is not between two letters or symbols is used to indicate a point of t attachment for a substituent. For example, —CONH$_2$ is attached through the carbon atom.

A dashed cycle located inside of a heterocyle ring is used to indicate a conjugated system. The bonds between two atoms may be single bond or double bond.

The term "kinase" refers to any enzyme that catalyzes the addition of phosphate groups to a protein residue; for example, serine and threonine kineses catalyze the addition of phosphate groups to serine and threonine residues.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term 'pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition comprising a compound of the invention to the subject in need of treatment.

The term "protected" refers that the group is in modified form to preclude undesired side reactions at the protected site. Suitable protecting groups for the compounds of the present invention will be recognized by those skilled in the art in view of the present application, and with reference to standard textbooks, such as Greene, T. W. et al., Protective Groups in Organic Synthesis, John Wiley & Sons, New York (1999).

The term "pharmaceutically acceptable salt" of a compound recited herein is an acid or base salt that is suitable for use in contact with the tissues of human beings or animals without excessive toxicity or carcinogenicity, and, for example, without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is suitable. It will be apparent that each compound of Formula I may, but need not, be formulated as a hydrate, solvate or non-covalent complex. In addition, the various crystal forms and polymorphs are within the scope of the present invention.

In one embodiment, Formula (I) is in the form of (Ia) as below:

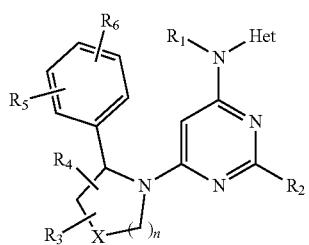

(Ia)

or a pharmaceutically acceptable salt thereof, wherein:
$R_1$ represents hydrogen, $C_1$-$C_4$ alkyl.
$R_2$ represents hydrogen, $NH_2$ and $C_1$-$C_4$ alkyl.
$R_3$ and $R_4$ respectively represent hydrogen, F, CN, oxo, $C_1$-$C_4$ alkyl, cycloalkyl, $C_1$-$C_6$ alkoxy, $C_2$-$C_4$ alkenyl, $C_2$-$C_4$ alkynyl.
$R_5$ and $R_6$ respectively represent hydrogen, F, Cl, Br, I, CN, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, $CON(R_7)R_8$.
$R_7$ and $R_8$ are independently selected from hydrogen, $C_1$-$C_4$ alkyl, $C_2$-$C_6$ alkenyl, $C_2$-$C_6$ alkynyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy.
n=0-3.
X represents $CH_2$, NR, O or S. R represents hydrogen, $C_1$-$C_4$ alkyl, cycloalkyl, $C_1$-$C_6$ alkoxy, $C_2$-$C_4$ alkenyl, $C_2$-$C_4$ alkynyl.
Het represents $C_2$-$C_8$ heteroaryl, which is substituted with from 0 to 4 substituents independently chosen from:
(1) halogen, hydroxy, amino, amide, cyano, —COOH, —$SO_2NH_2$, oxo, nitro and alkoxycarbonyl;
(2) $CON(R_7)R_8$, $N(R_7)R_8$; and
(3) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_5$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

In another embodiment, Formula (I) is in the form of (Ib) as below:

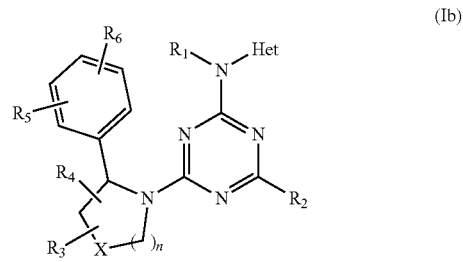

(Ib)

or a pharmaceutically acceptable salt thereof, wherein:
$R_1$ represents hydrogen, $C_1$-$C_4$ alkyl.
$R_2$ represents hydrogen, $NH_2$ and $C_1$-$C_4$ alkyl.
$R_3$ and $R_4$ respectively represent hydrogen, F, CN, oxo, $C_1$-$C_4$ alkyl, cycloalkyl, $C_1$-$C_6$ alkoxy, $C_2$-$C_4$ alkenyl, $C_2$-$C_4$ alkynyl.
$R_5$ and $R_6$ respectively represent hydrogen, F, Cl, Br, I, CN, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, $CON(R_7)R_8$.
$R_7$ and $R_8$ are independently selected from hydrogen, $C_1$-$C_4$ alkyl, $C_2$-$C_6$ alkenyl, $C_2$-$C_6$ alkynyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy.
n=0-3.
X represents $CH_2$, NR, O or S. R represents hydrogen, $C_1$-$C_4$ alkyl, cycloalkyl, $C_1$-$C_6$ alkoxy, $C_2$-$C_4$ alkenyl, $C_2$-$C_4$ alkynyl.
Het represents $C_2$-$C_8$ heteroaryl, which is substituted with from 0 to 4 substituents independently chosen from:
(1) halogen, hydroxy, amino, amide, cyano, —COOH, —$SO_2NH_2$, oxo, nitro and alkoxycarbonyl;
(2) $CON(R_7)R_8$, $N(R_7)R_8$; and
(3) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

In certain embodiments, $R_9$ of formula (I) is: F, Cl, Br, CN, $CF_3$, $CF_2H$, $CFH_2$, $CH_3$, $OCH_3$, $NH_2$.

In certain embodiments, n of formula (I) is 1.

In certain embodiments, substituted Het groups of formula (I) are listed below:

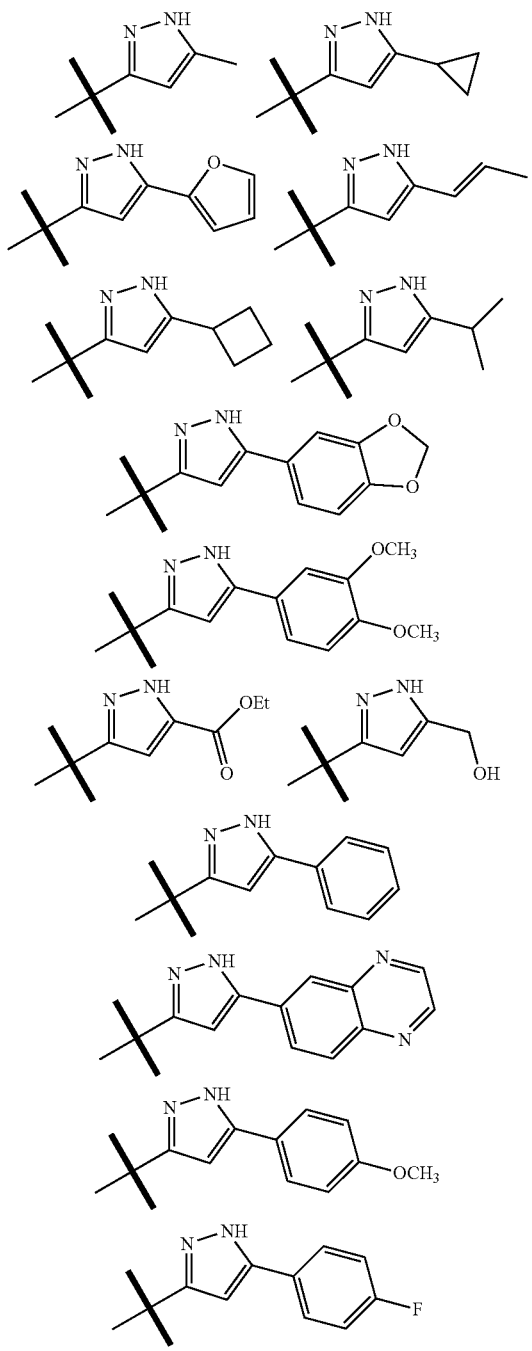

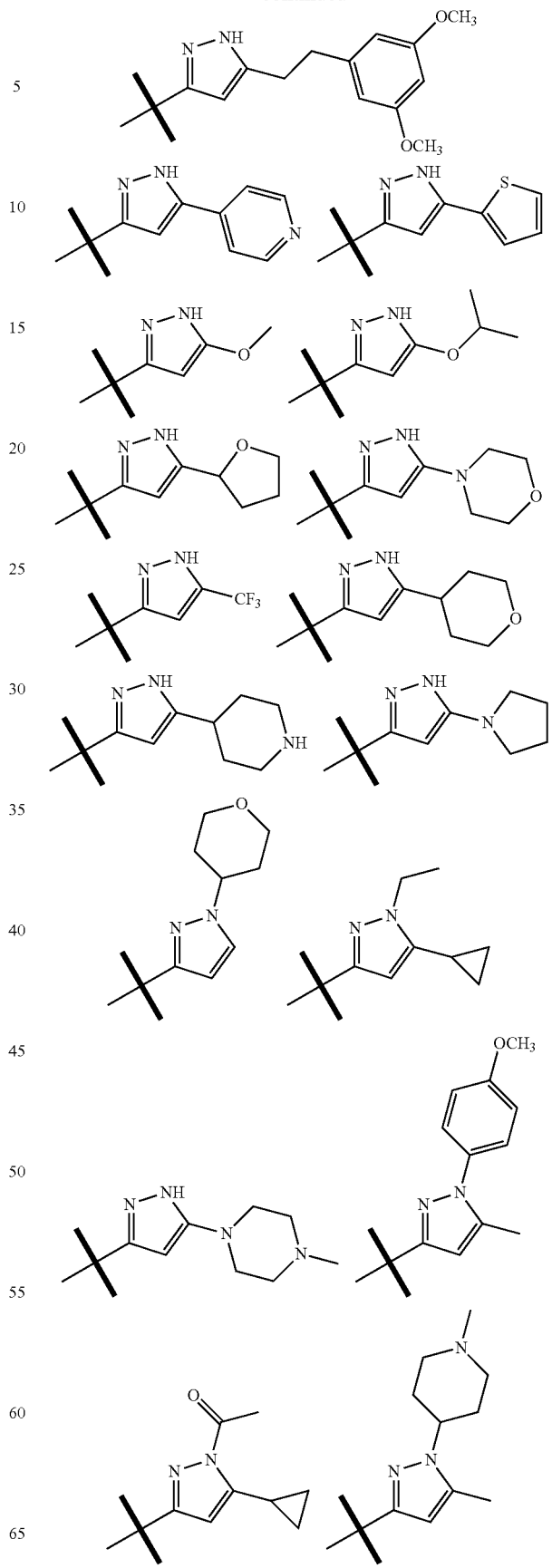

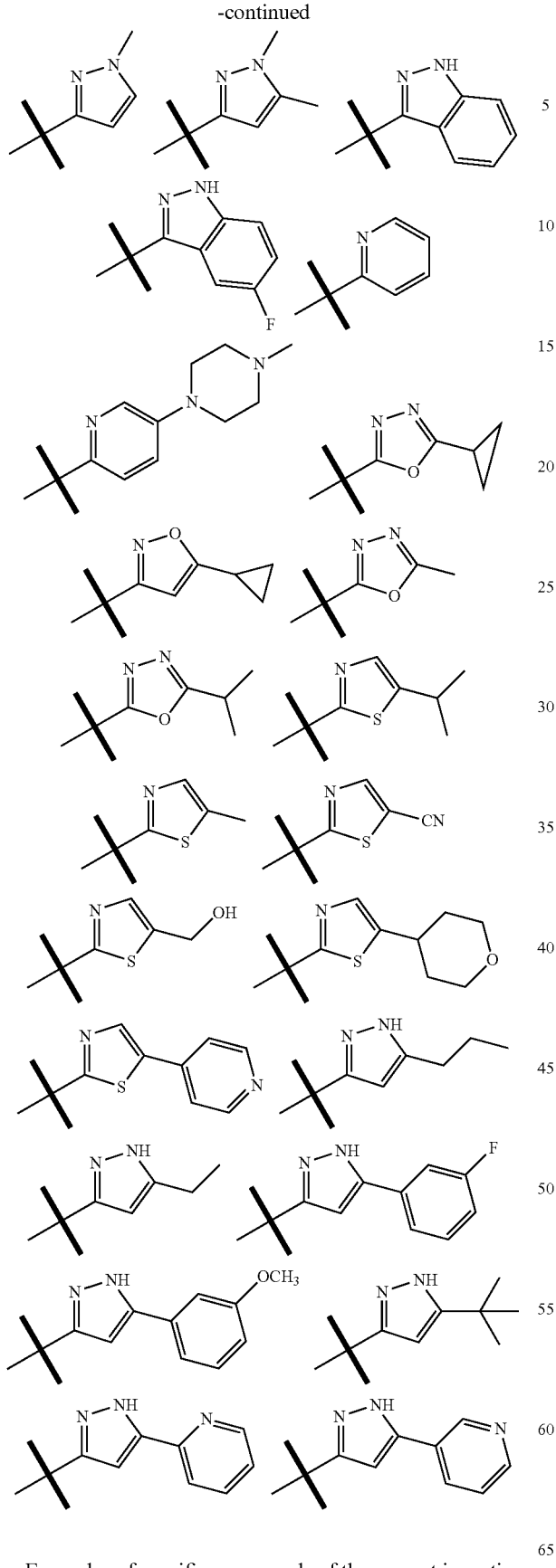
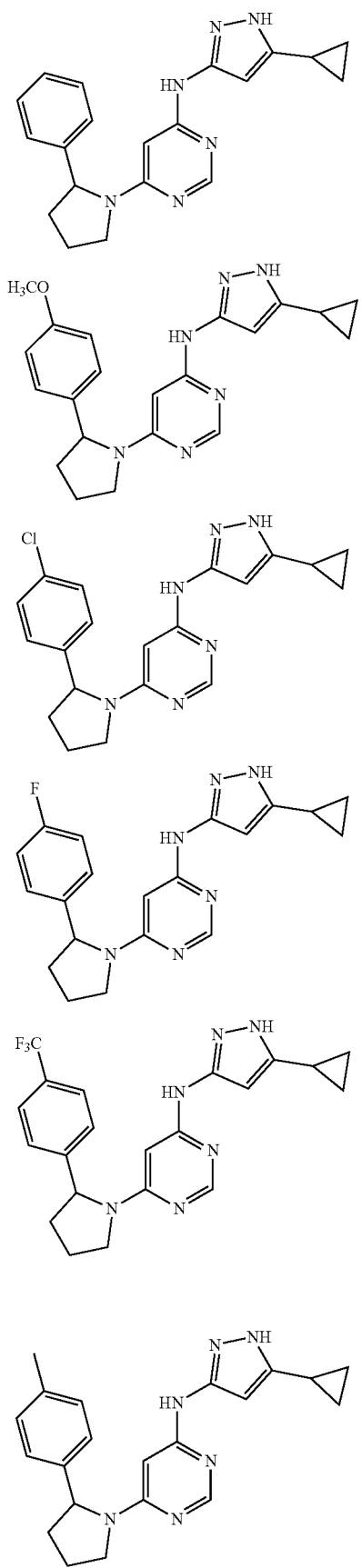
Examples of specific compounds of the present invention are those compounds defined in the following:

-continued
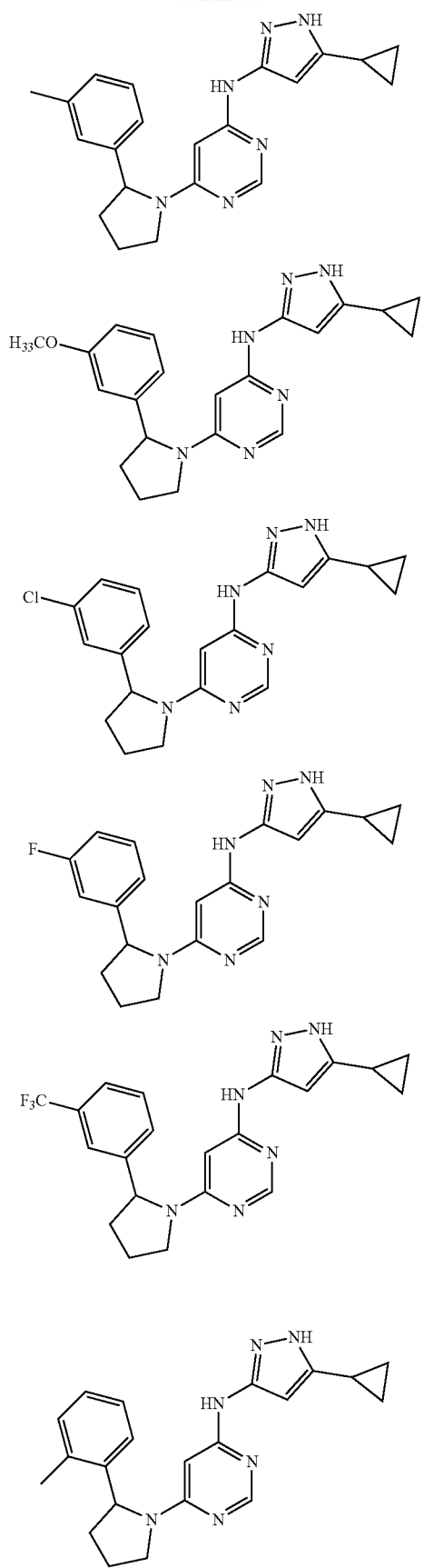
-continued
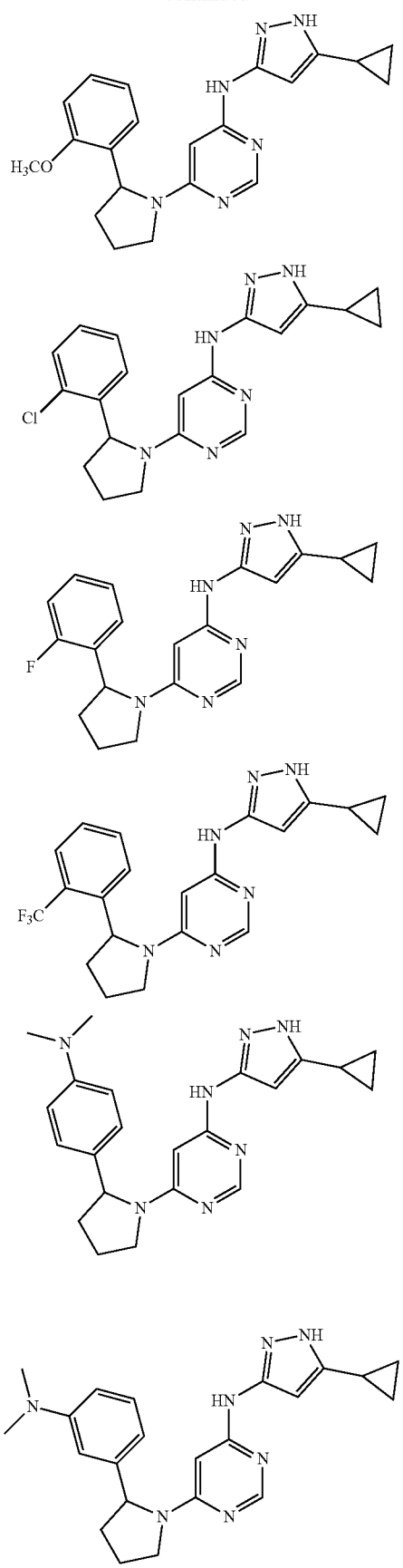

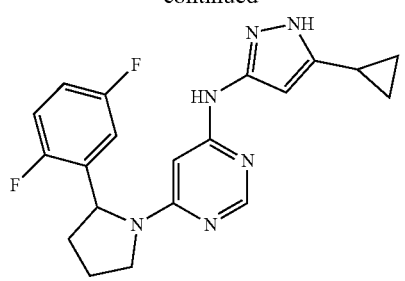
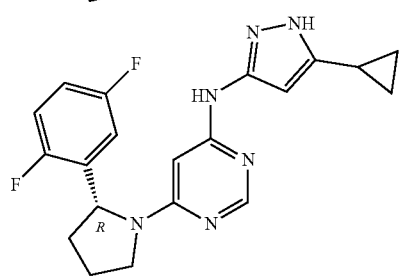
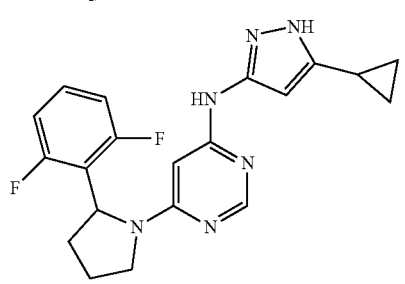
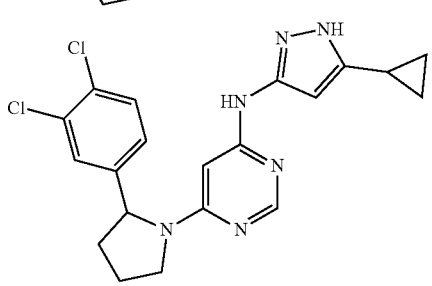
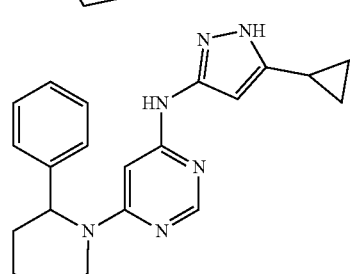
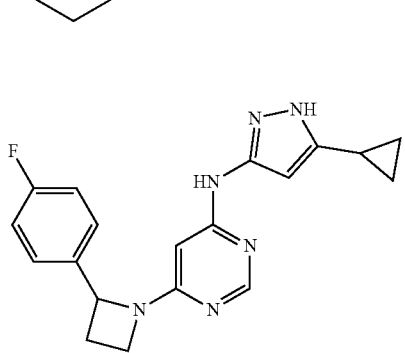
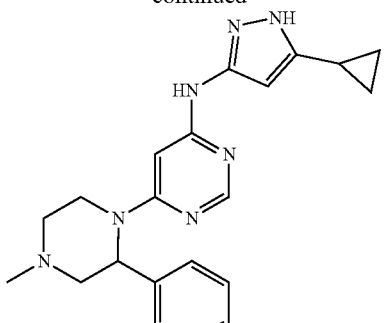
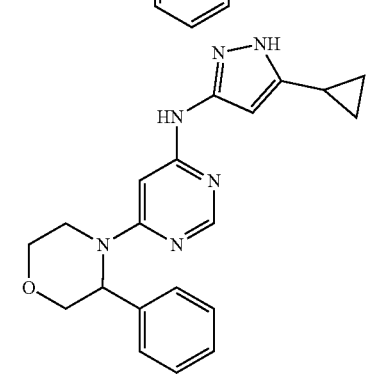
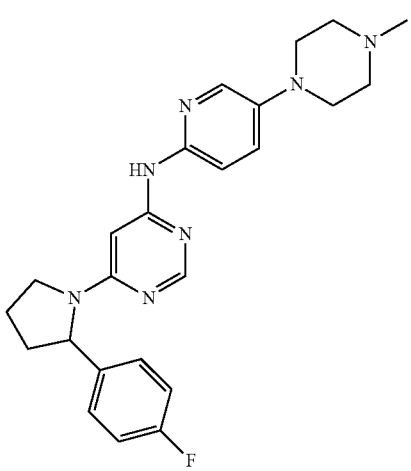
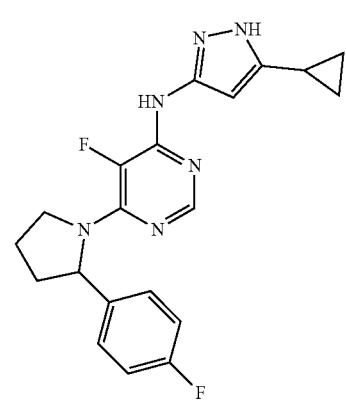

-continued
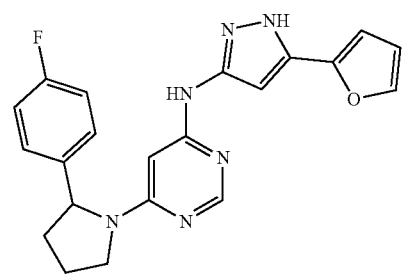
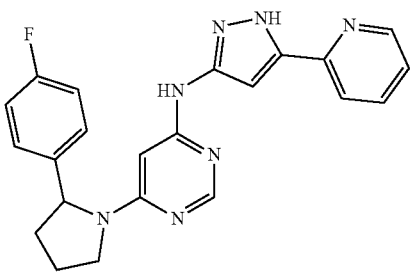
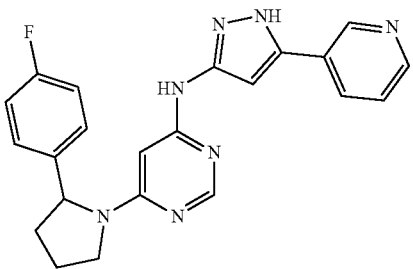
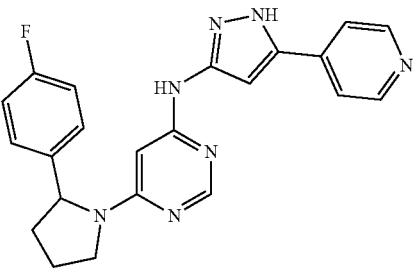
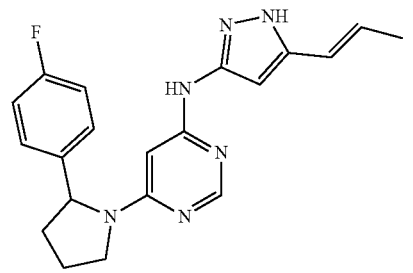
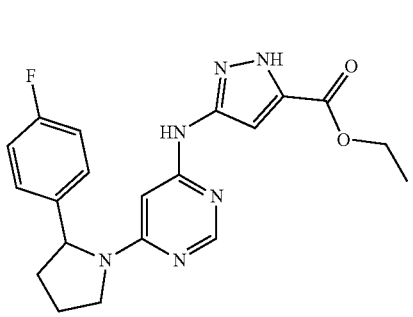
-continued
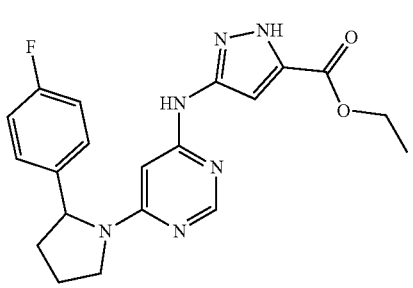

-continued
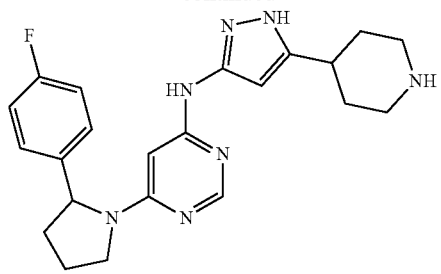
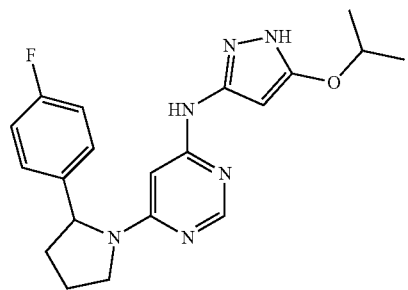
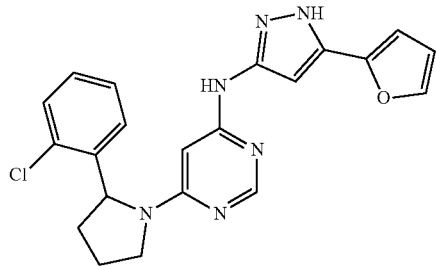
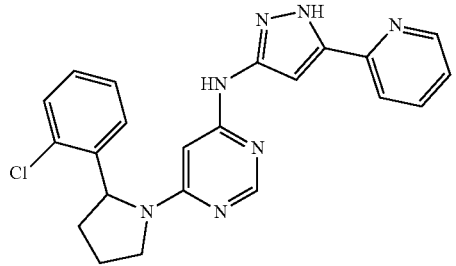
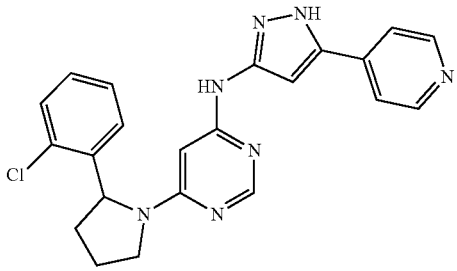
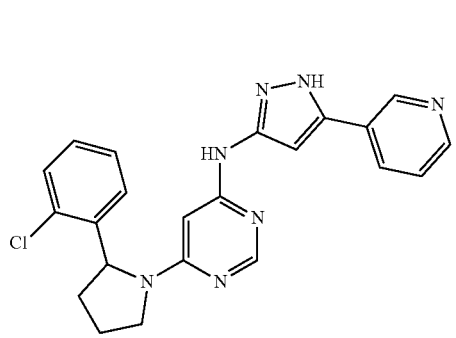
-continued
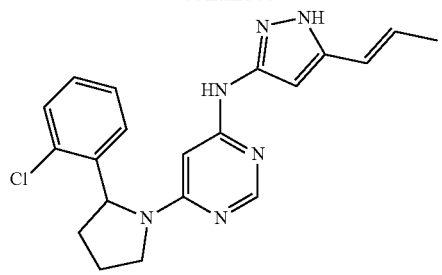
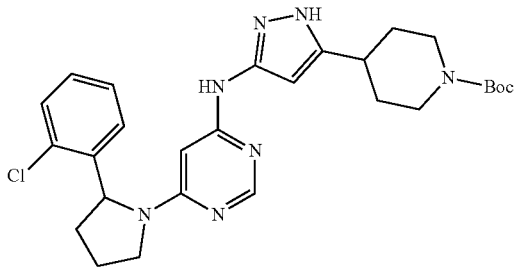
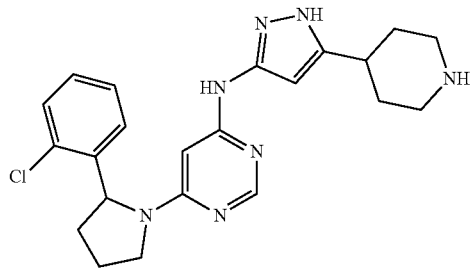
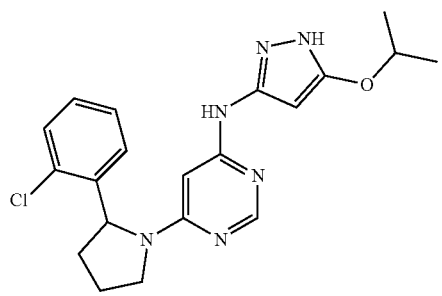
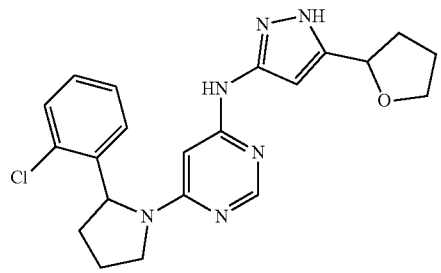
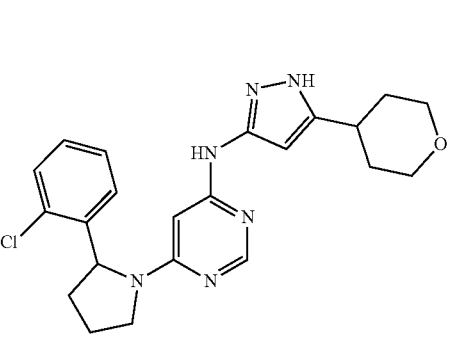

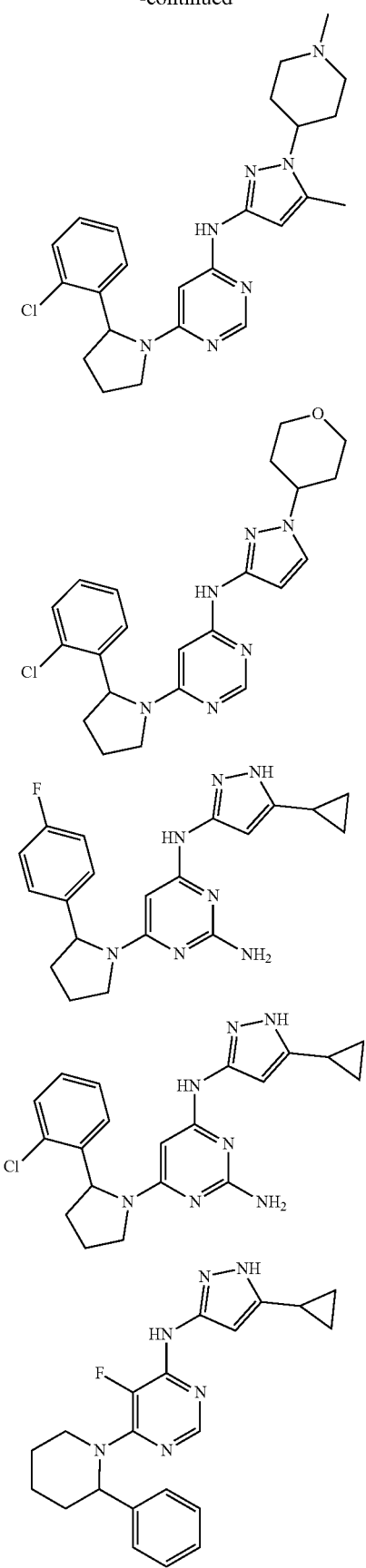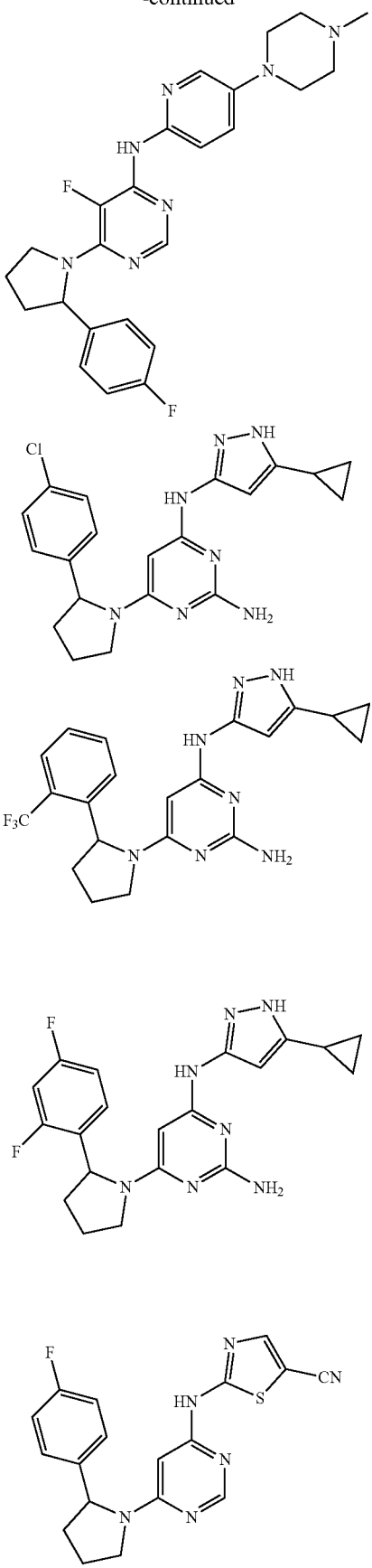

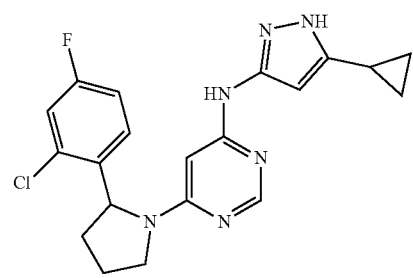
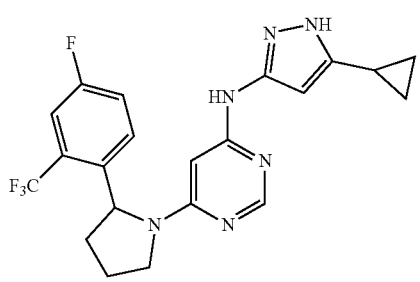
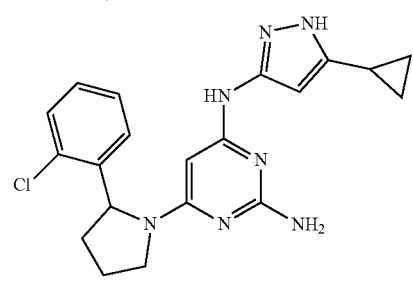
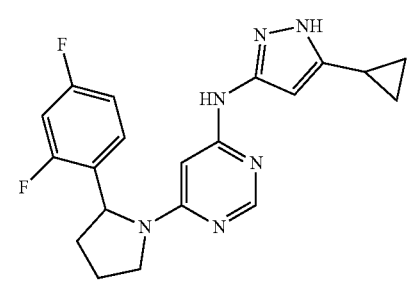
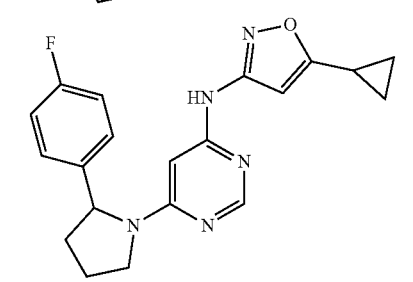
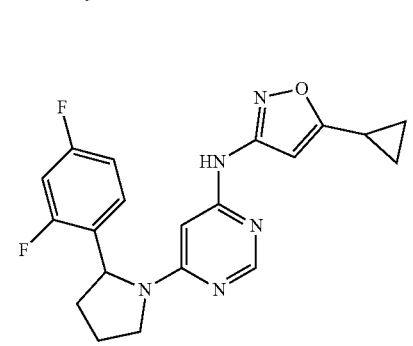
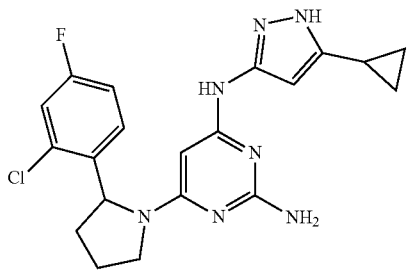
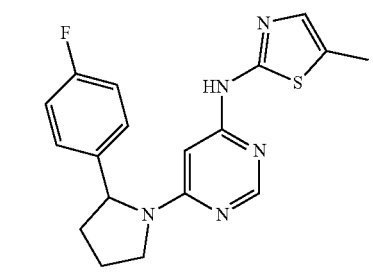
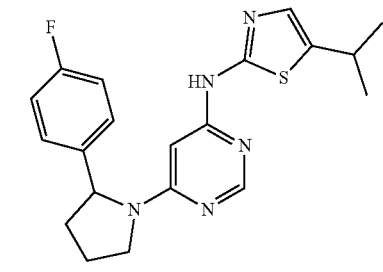
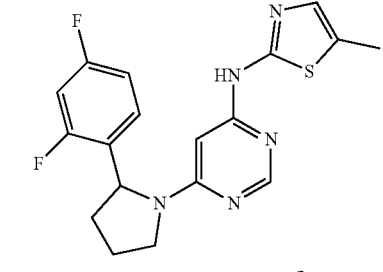
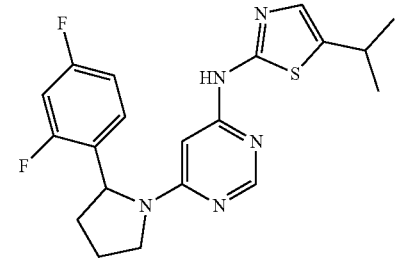
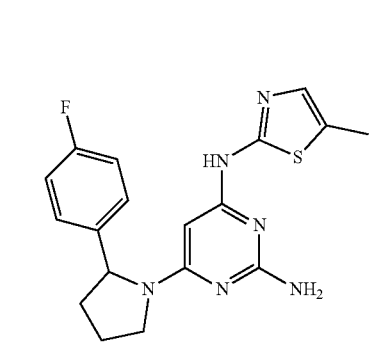

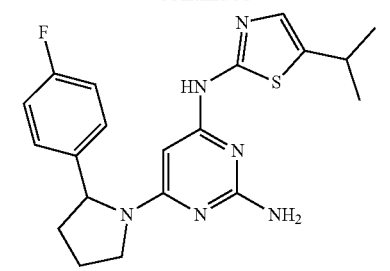
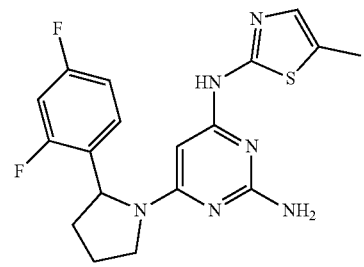
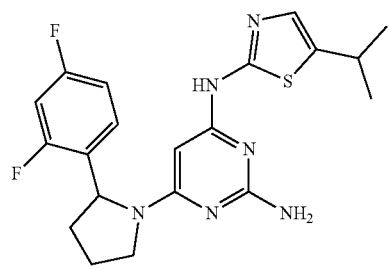
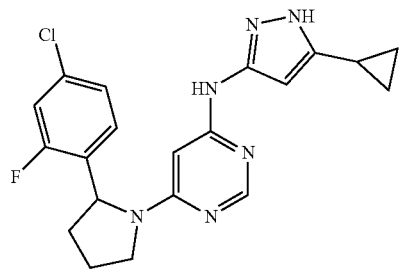
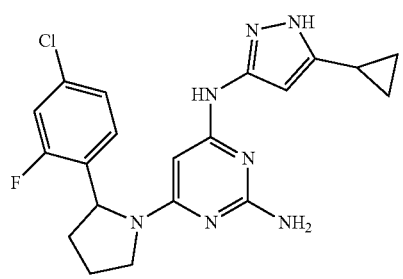
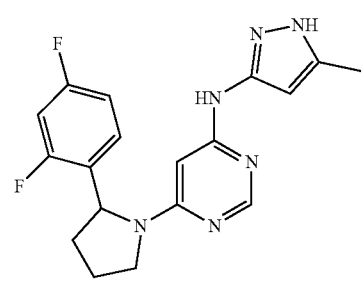
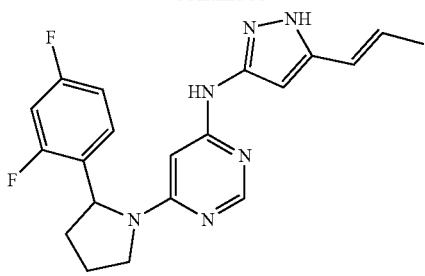
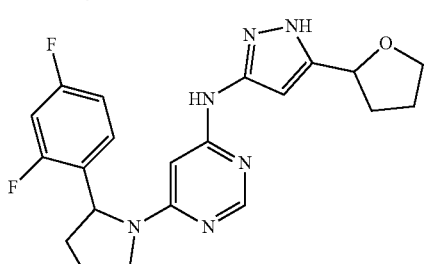
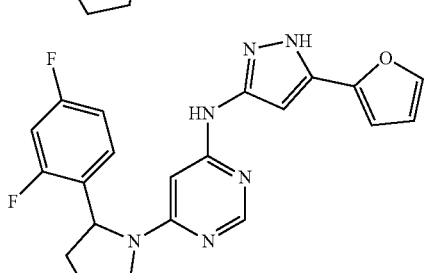
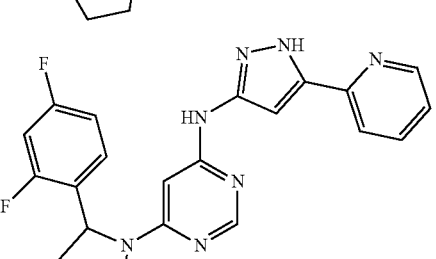
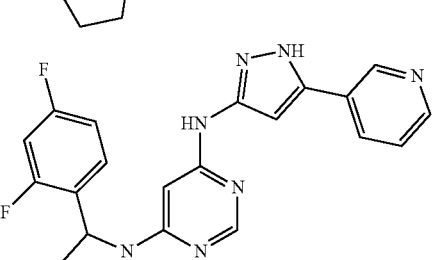
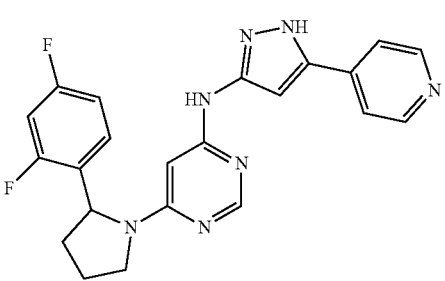

-continued
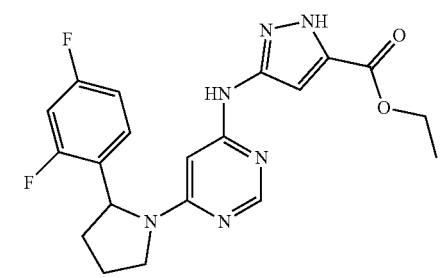
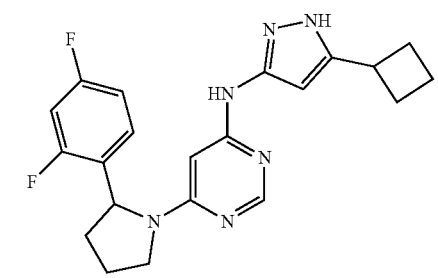
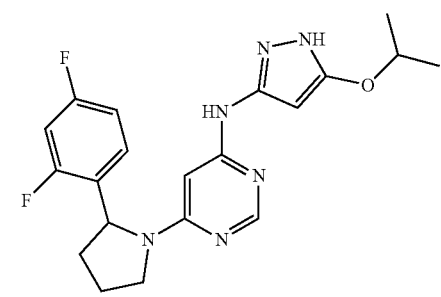
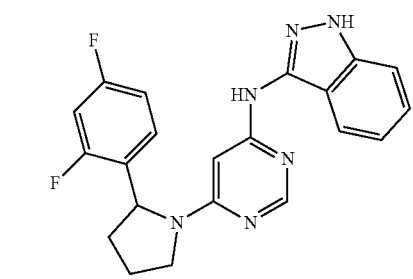
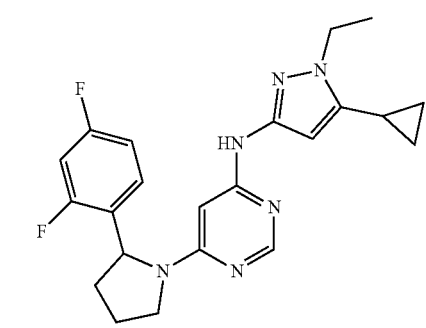
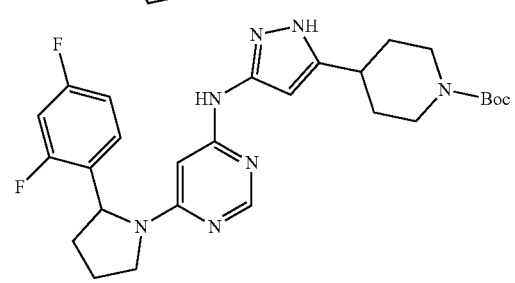
-continued
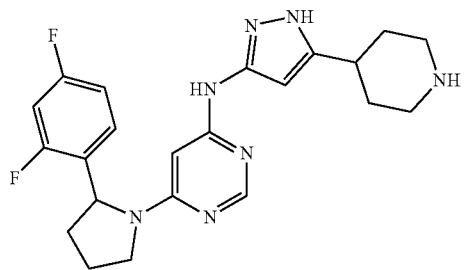
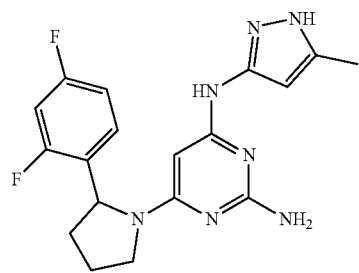
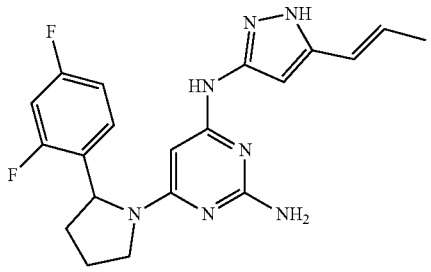
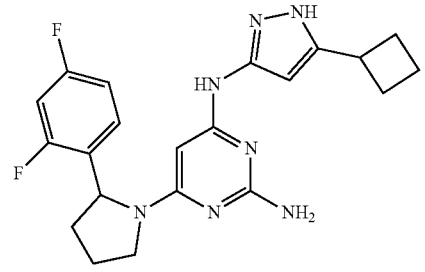
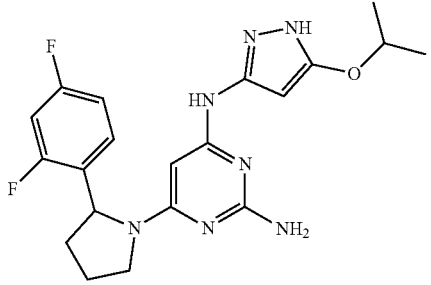
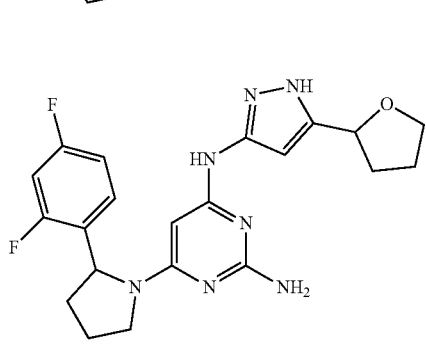

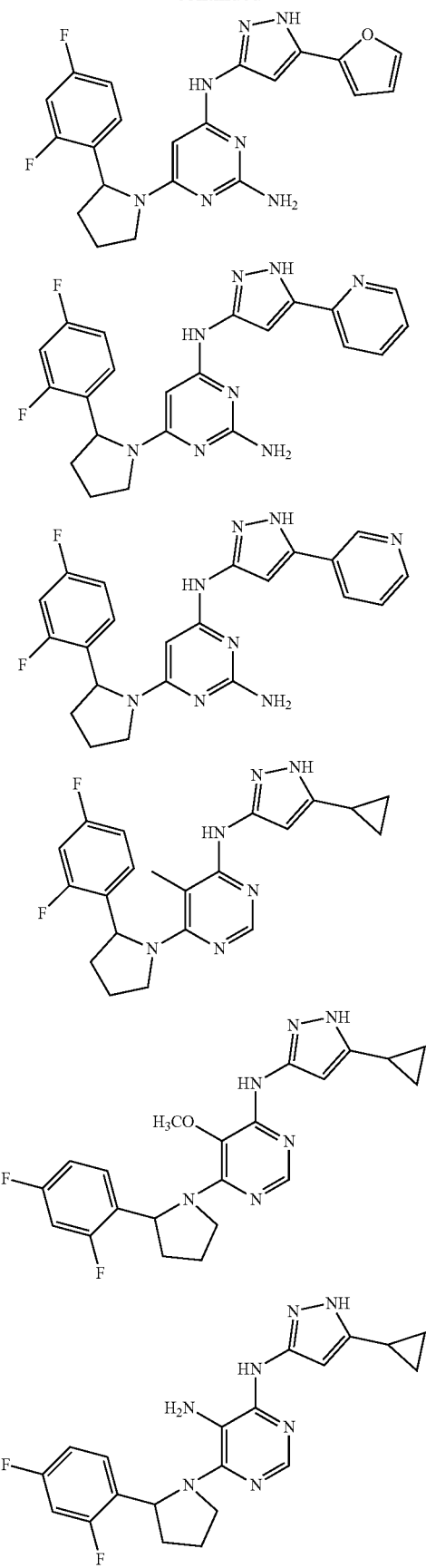
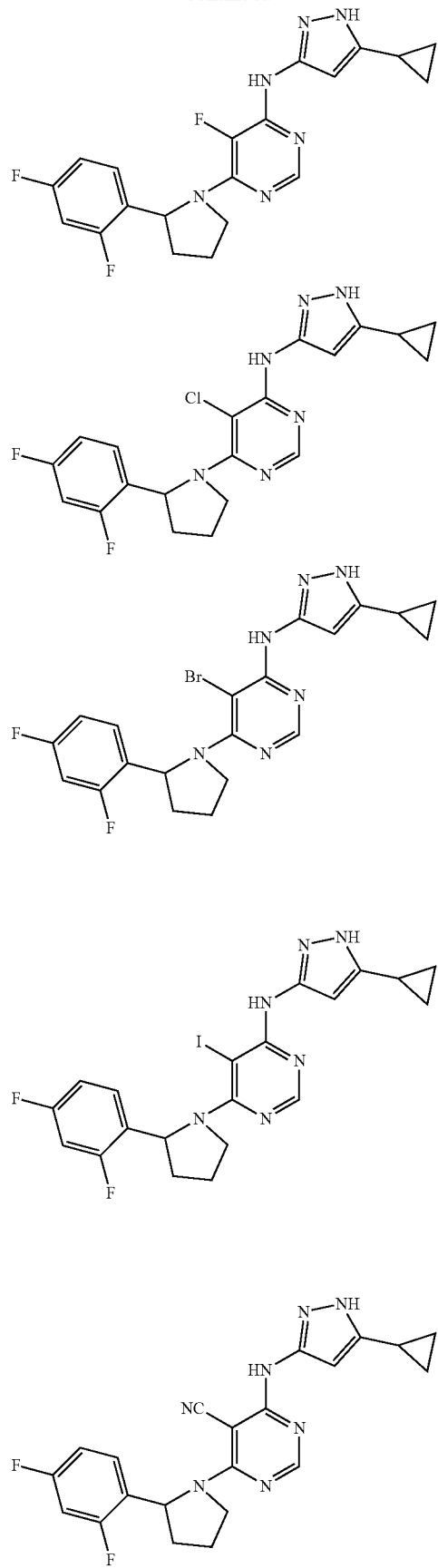

-continued
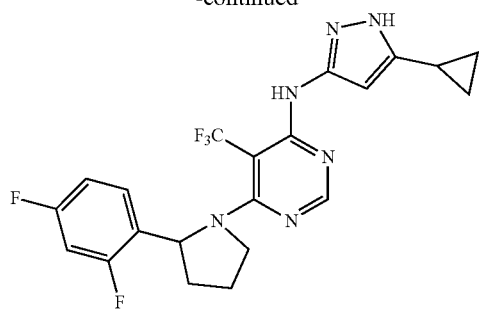
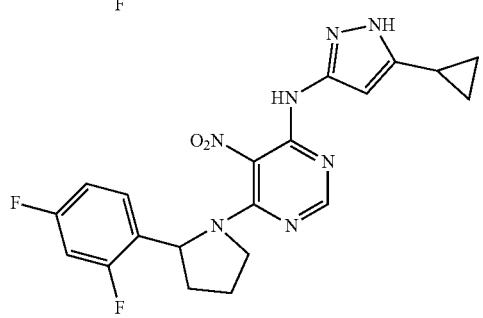
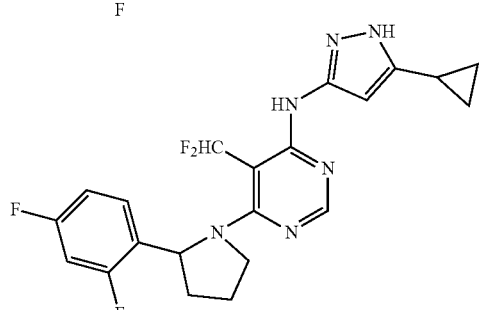
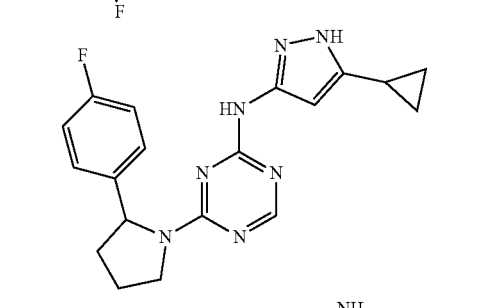
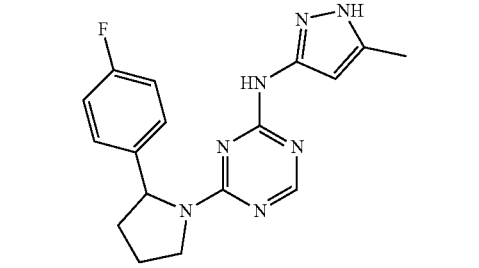
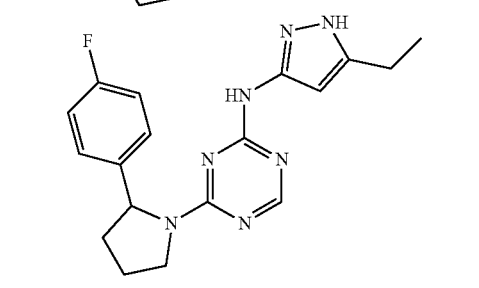
-continued
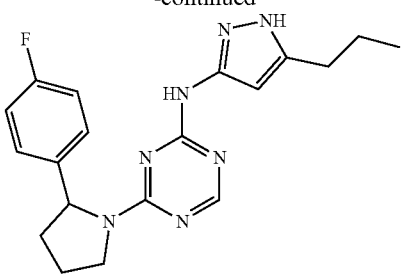
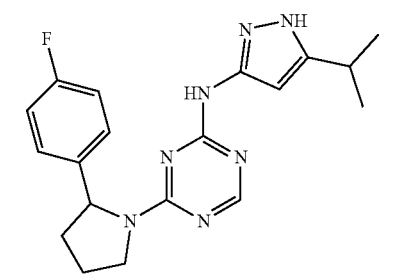
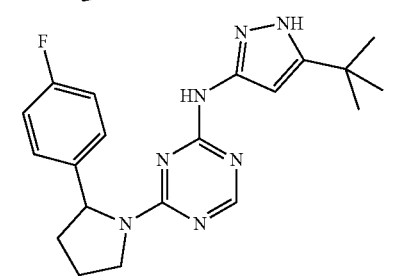
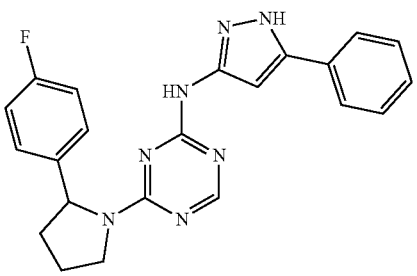
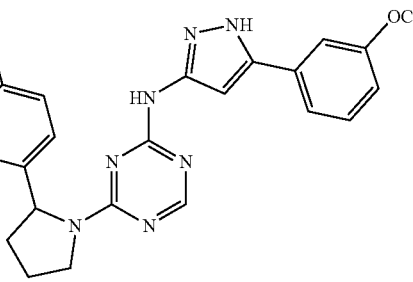
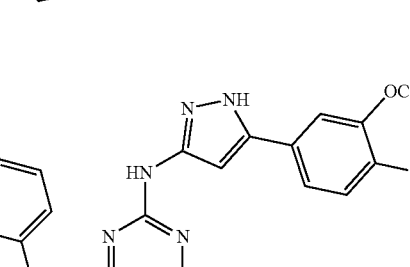

-continued
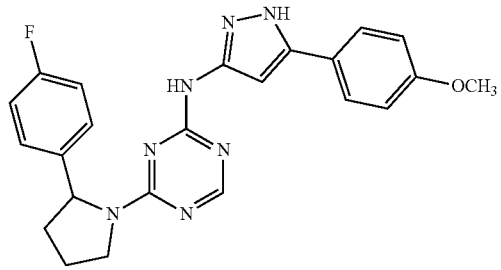
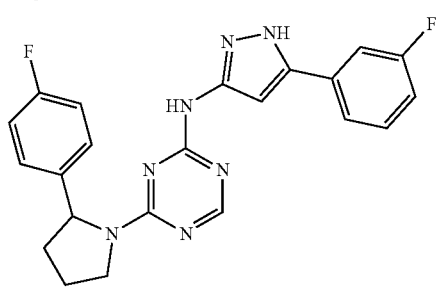
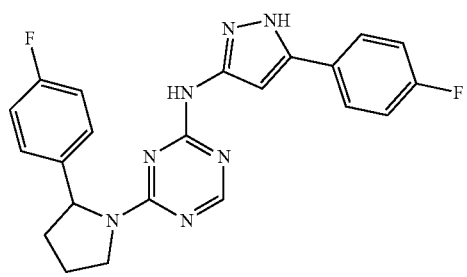
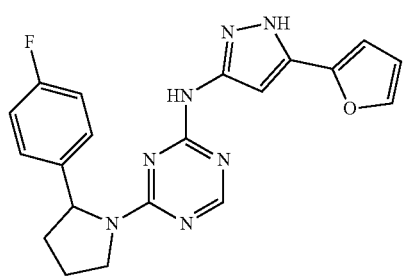
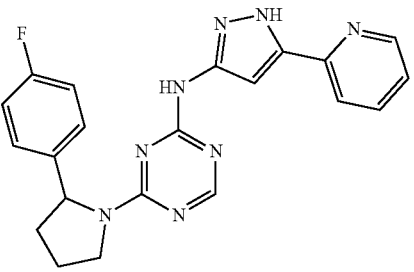
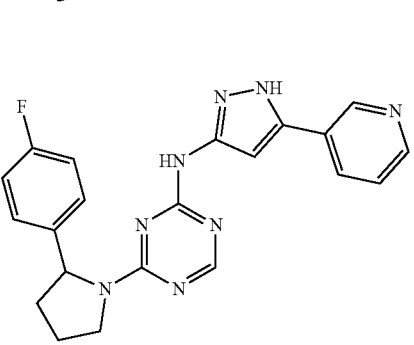
-continued
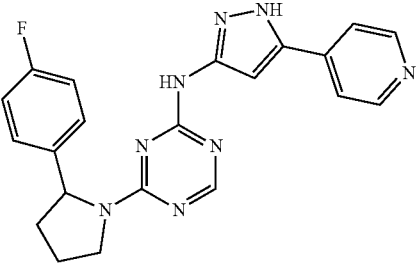
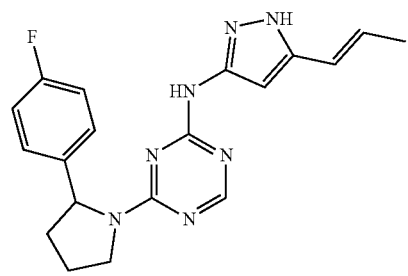
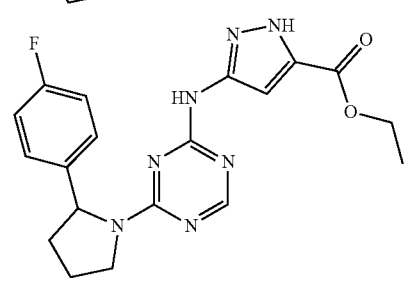
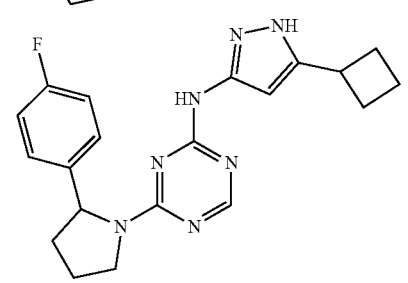
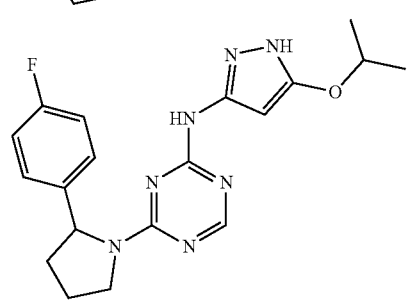
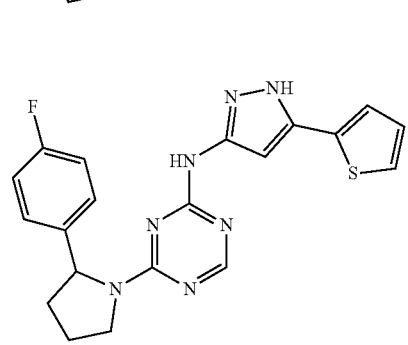

35
-continued
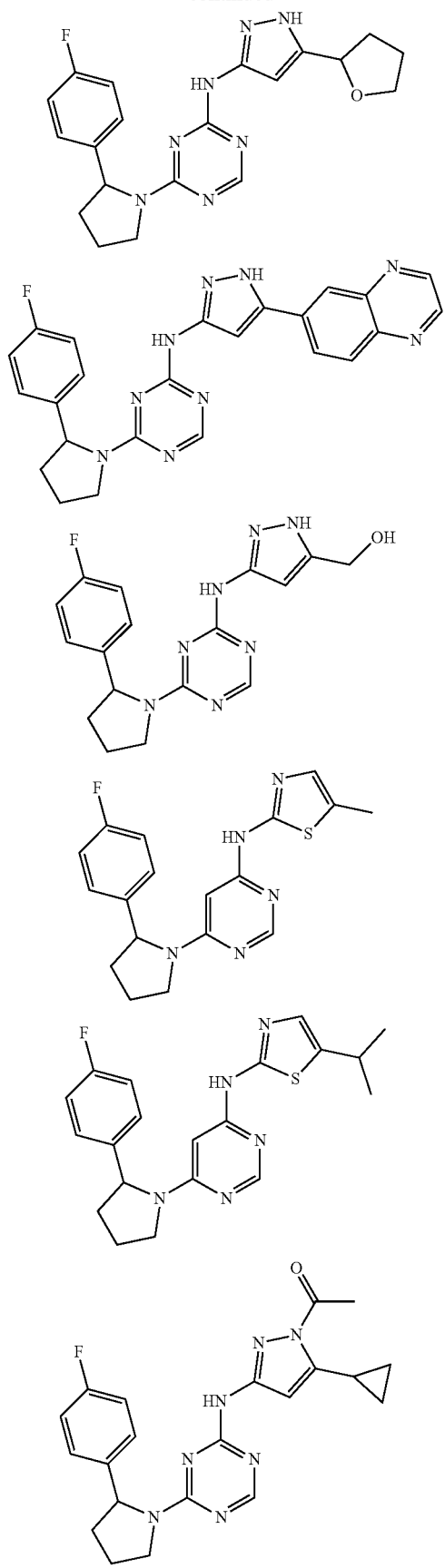
36
-continued
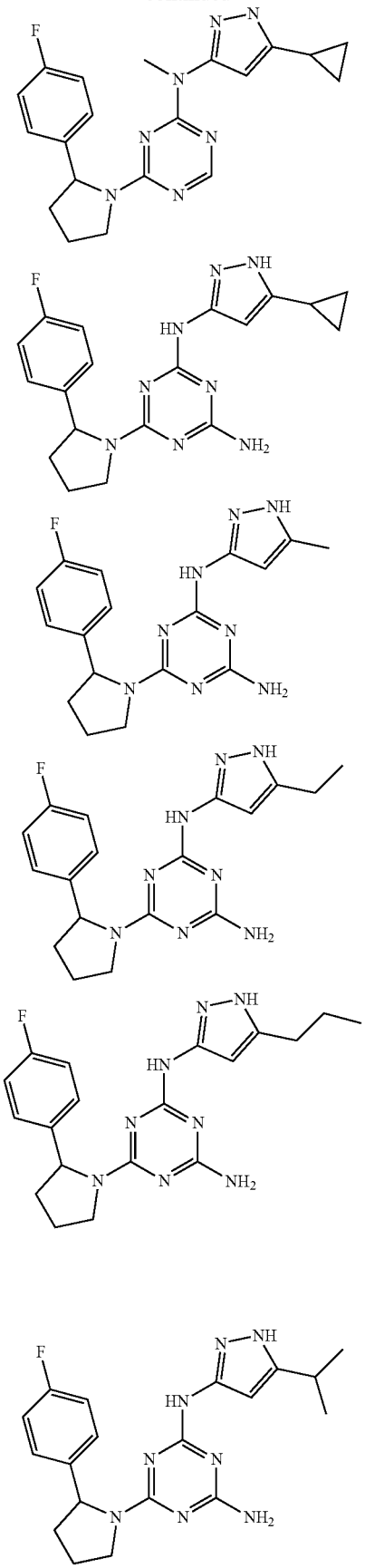

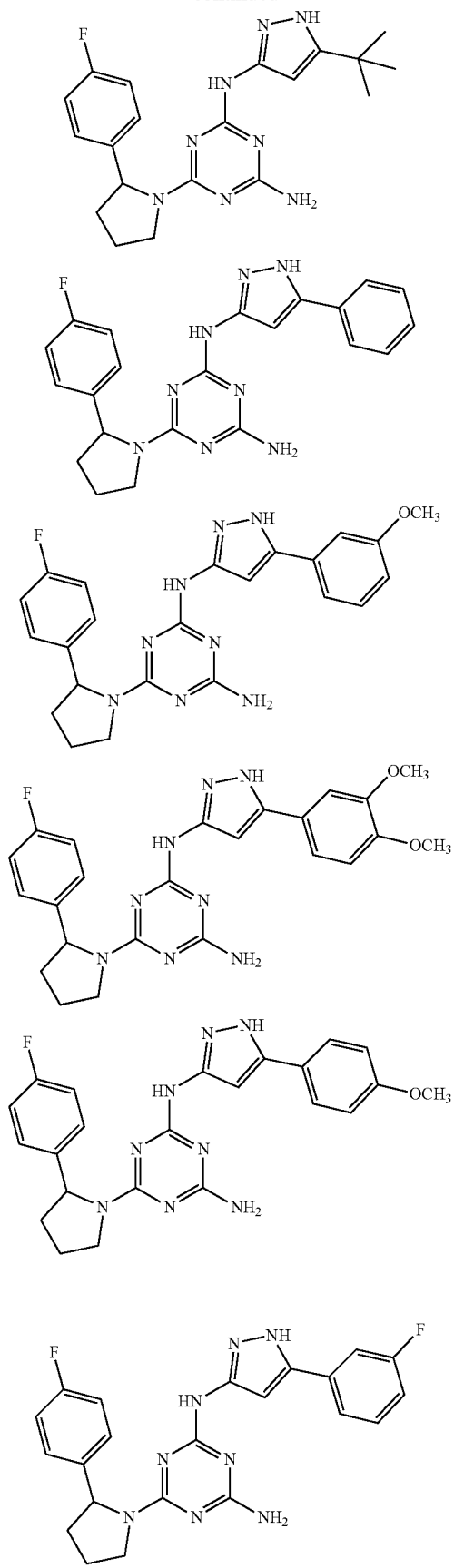
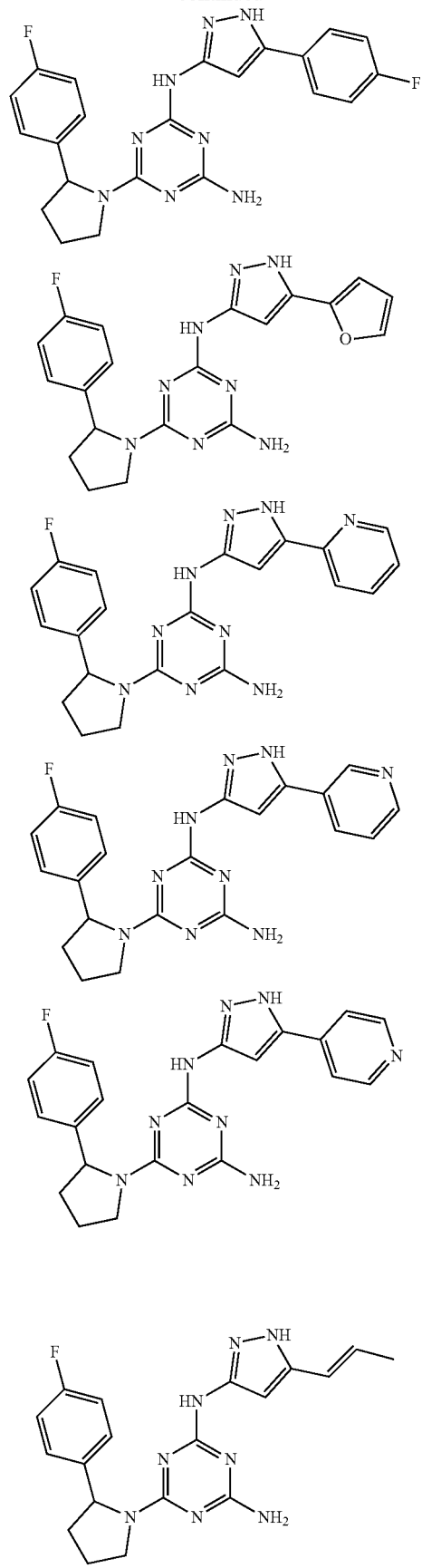

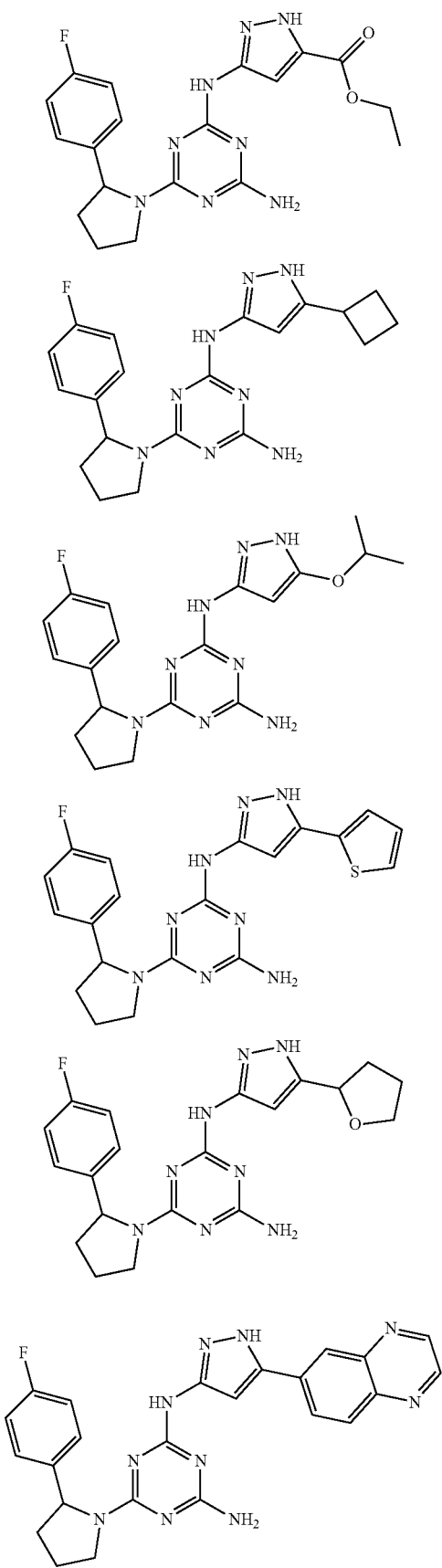
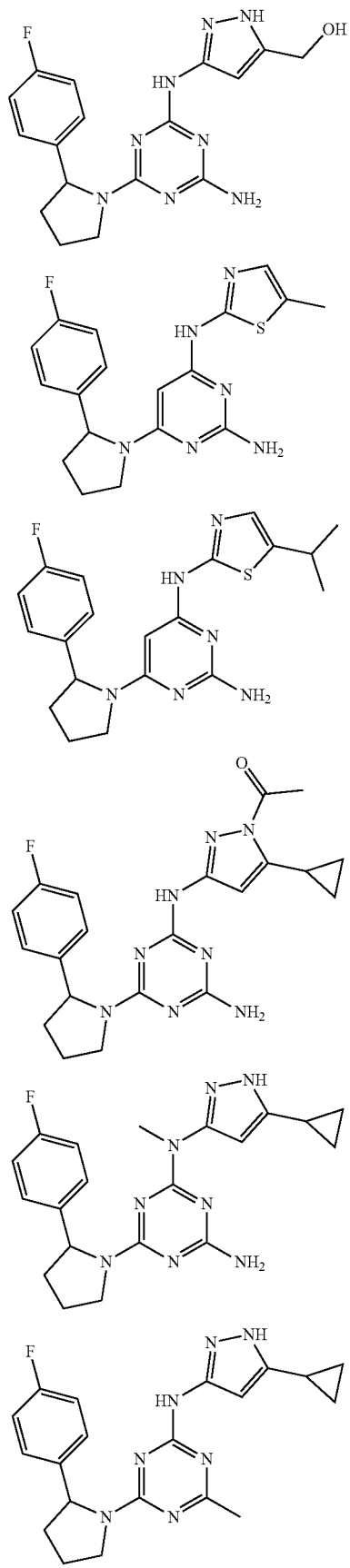

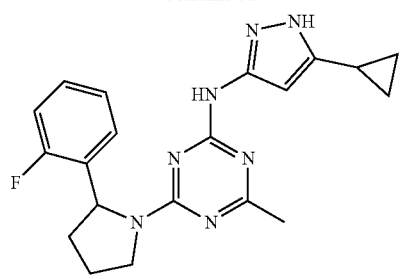
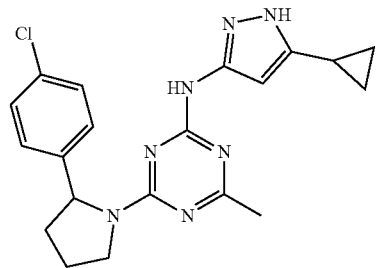
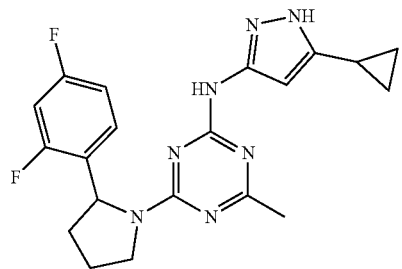
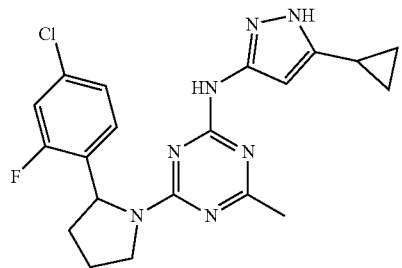
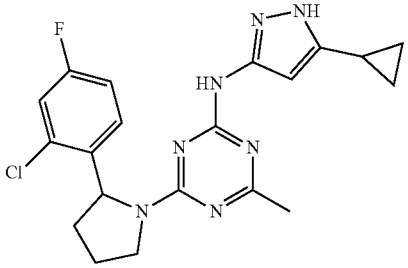
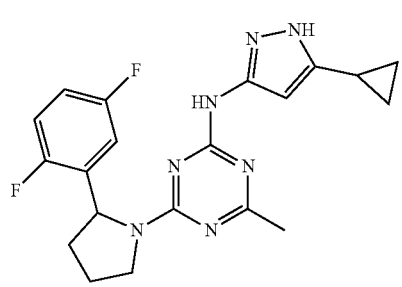
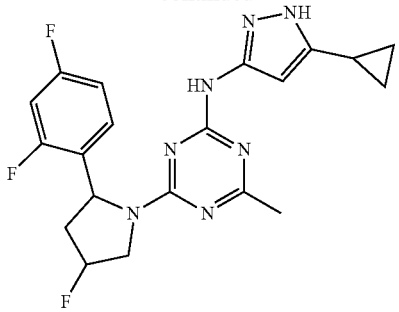
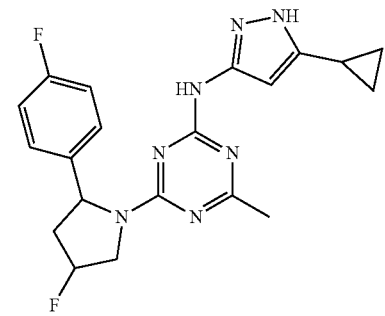
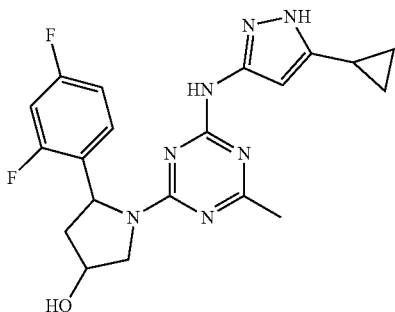
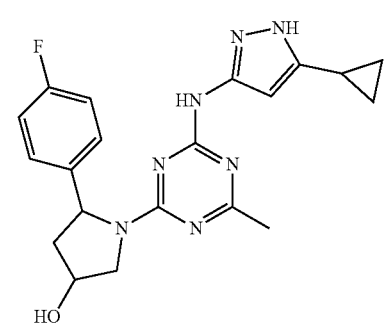
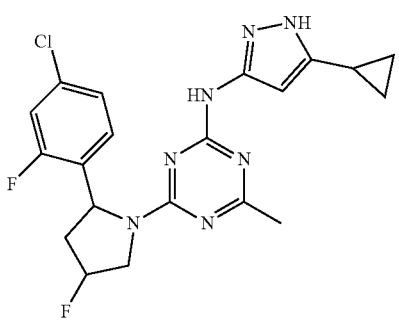

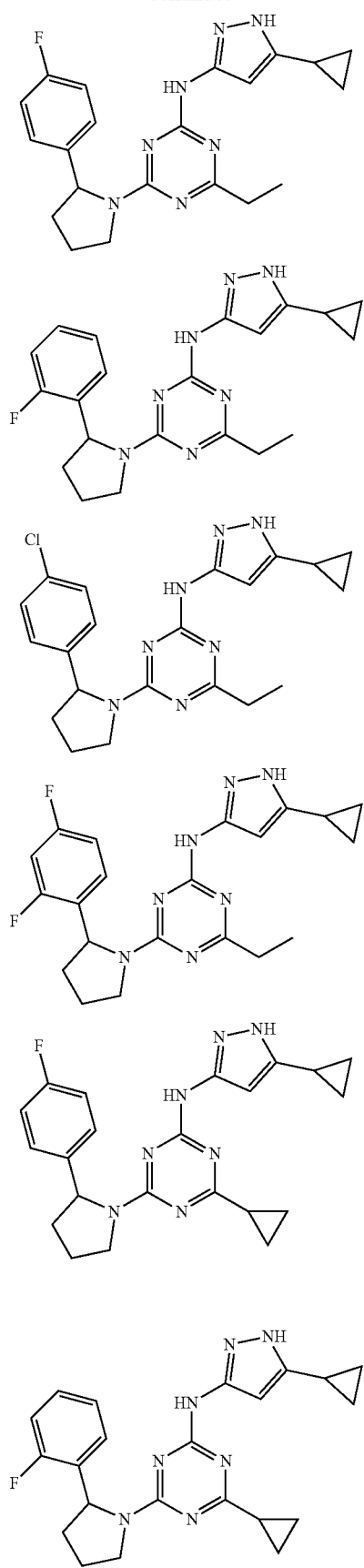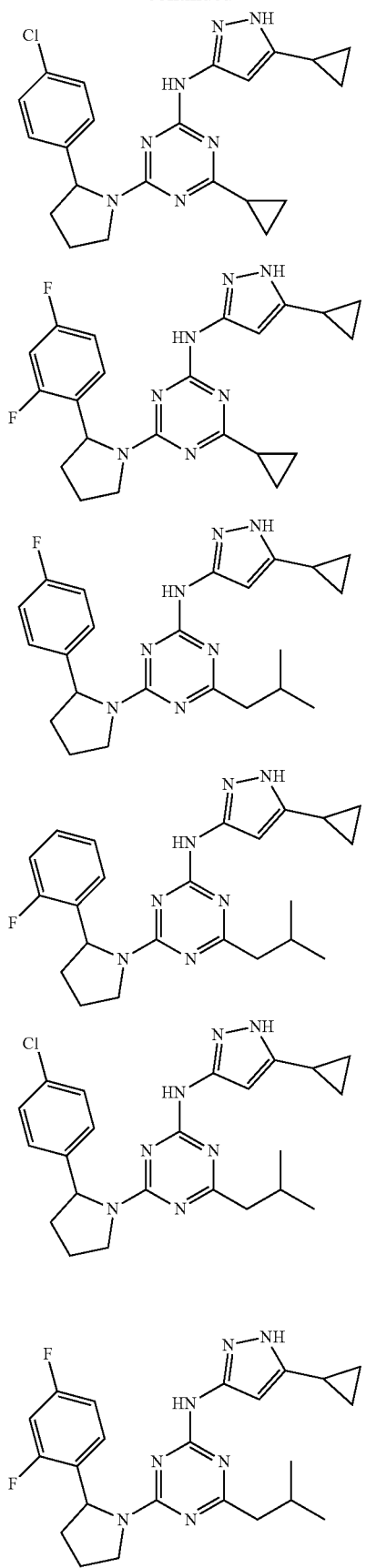

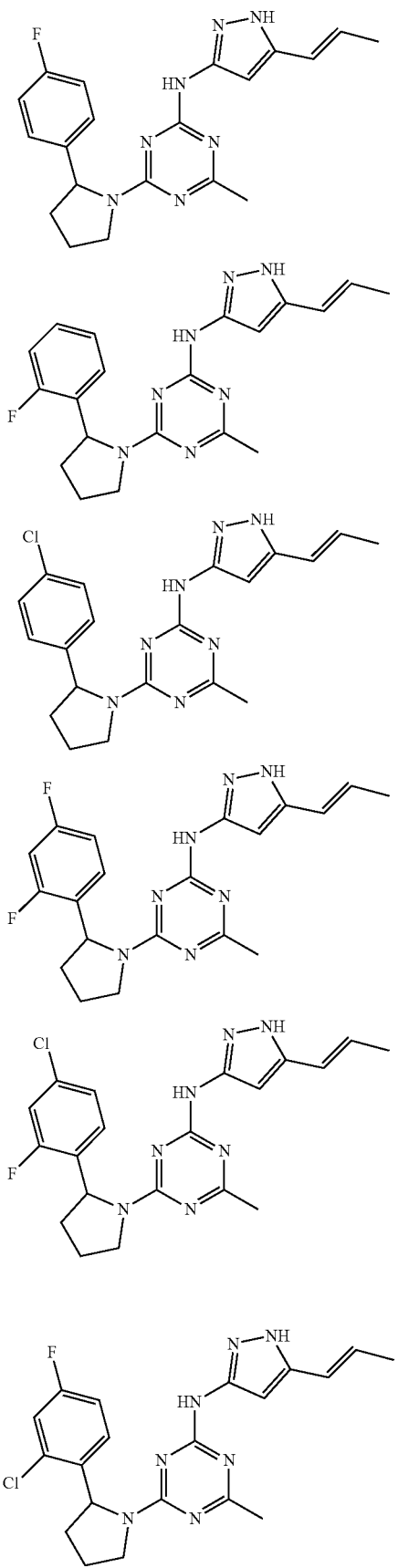
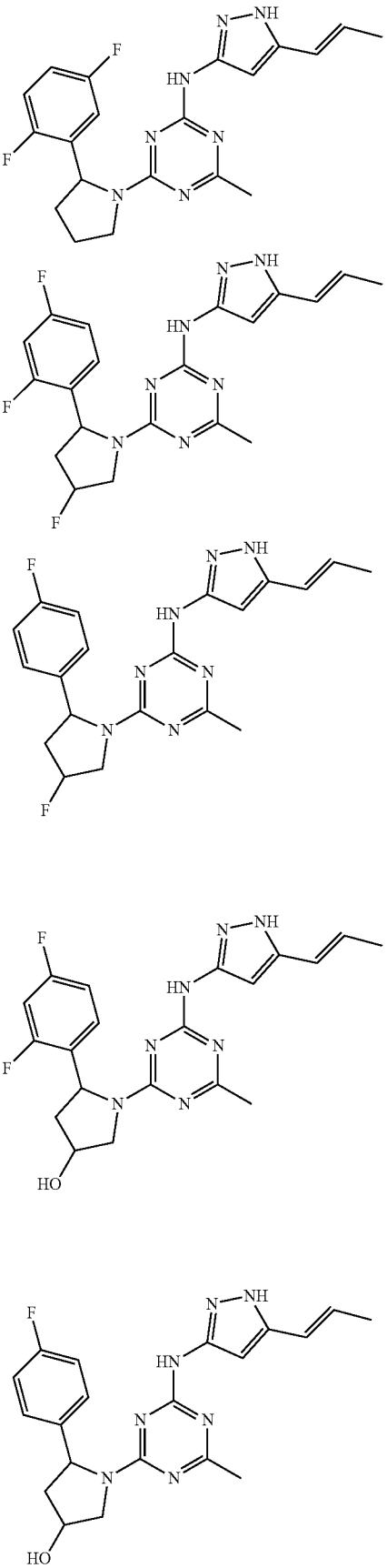

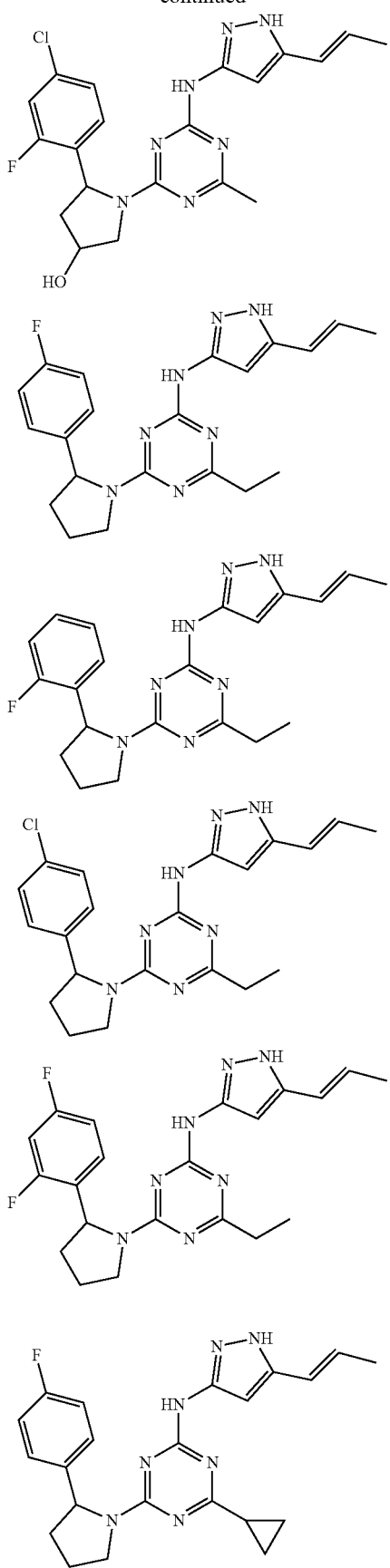
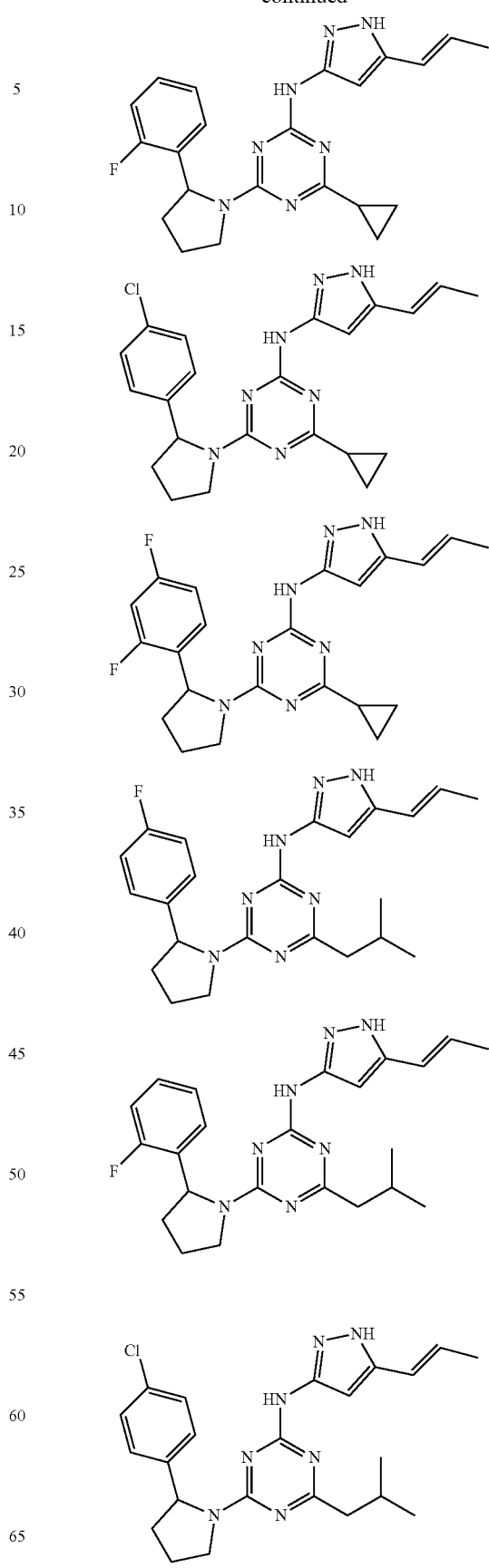

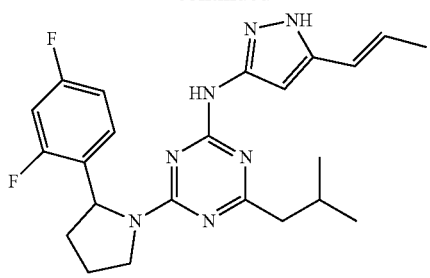
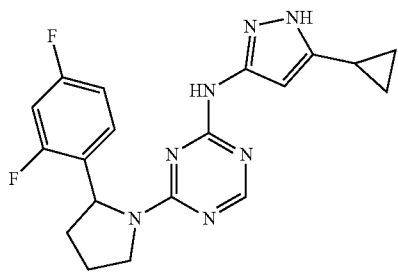
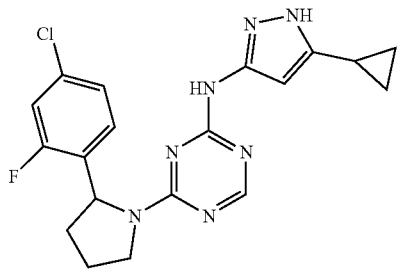
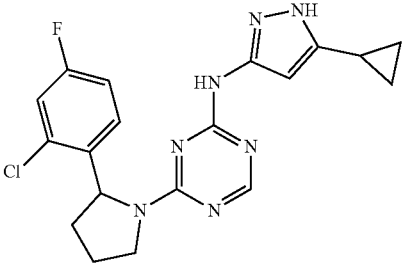
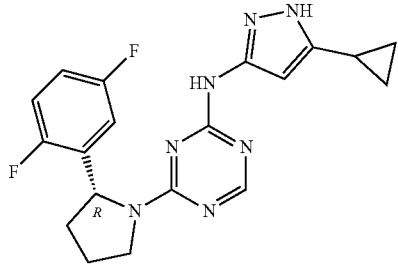
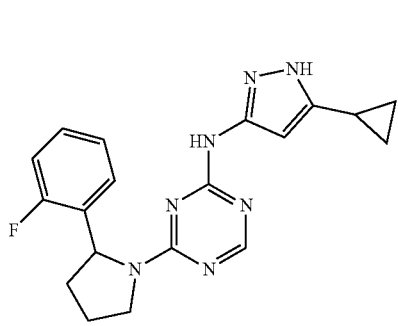
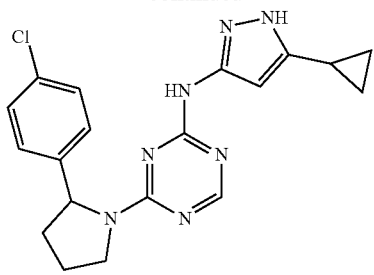
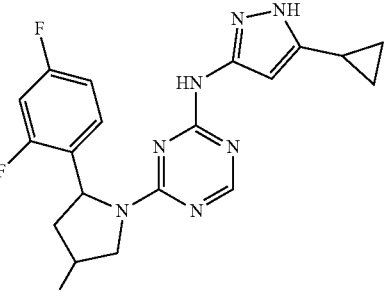
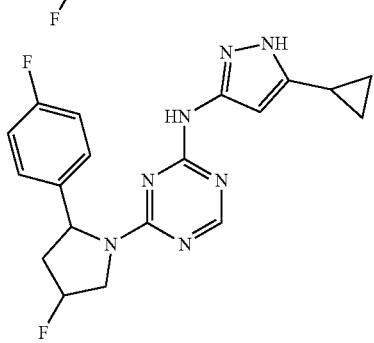
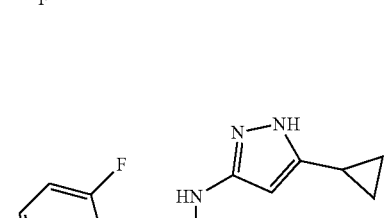
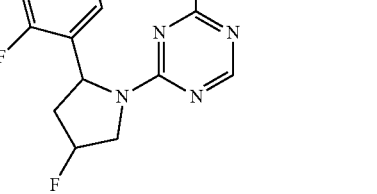
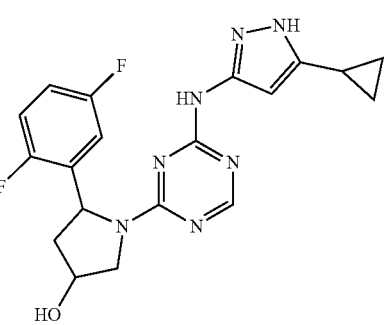

-continued
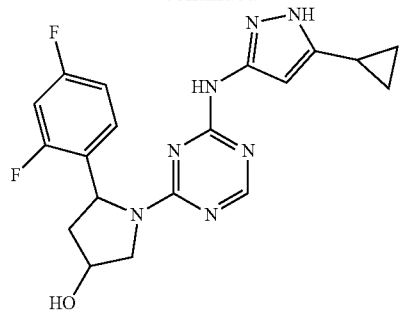
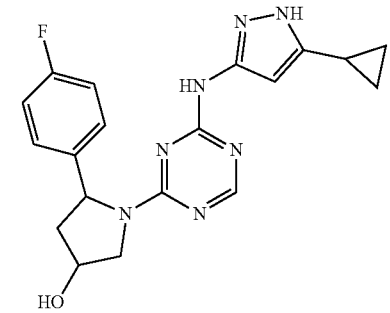
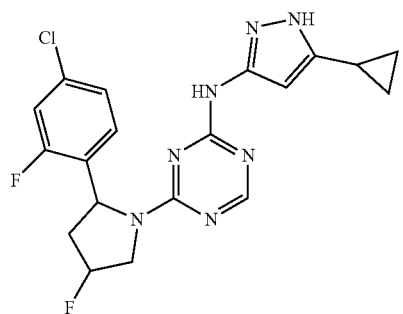
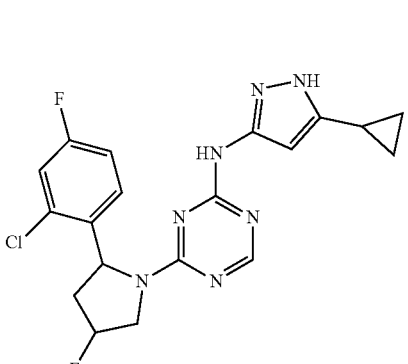
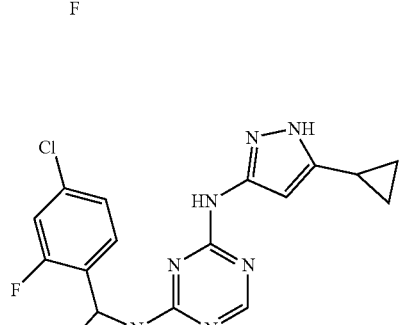
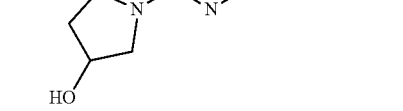
-continued
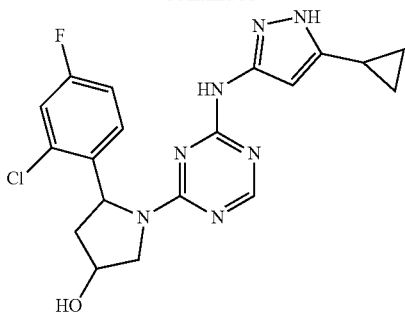
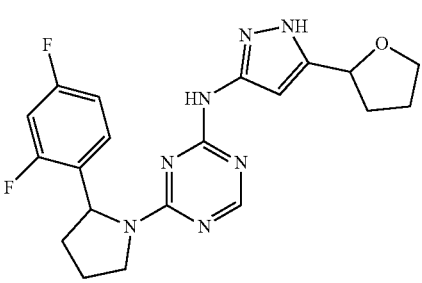
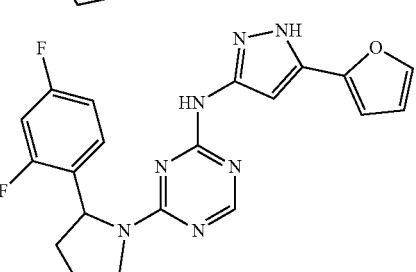
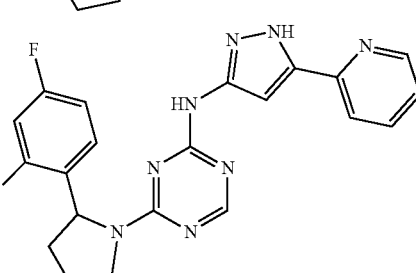
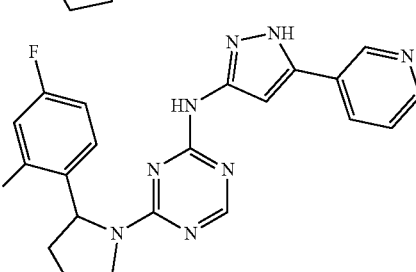
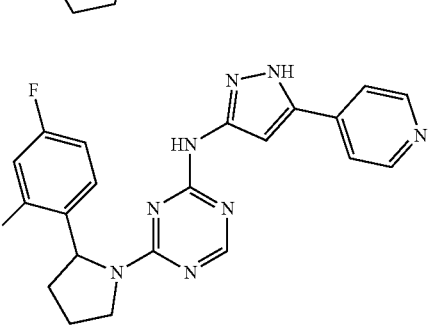

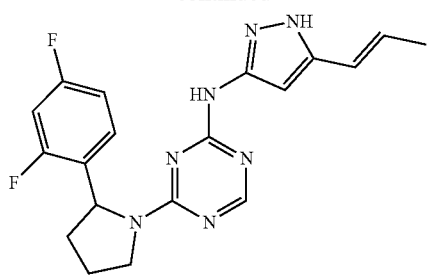
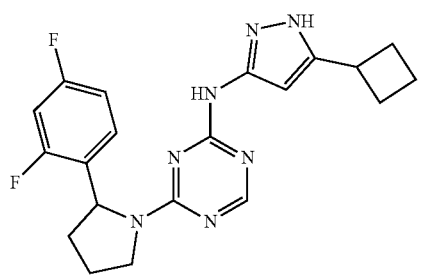
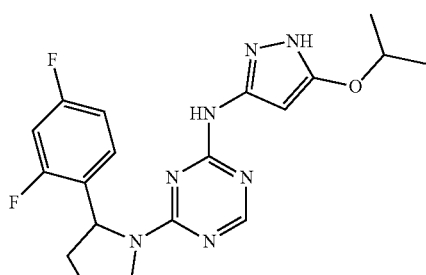
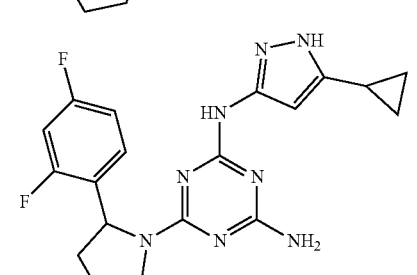
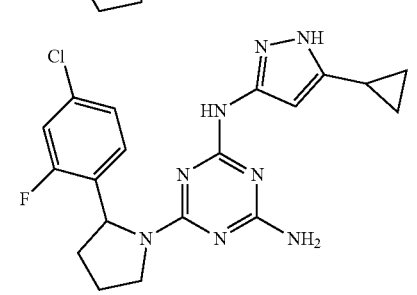
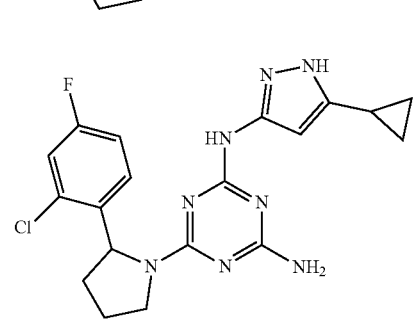
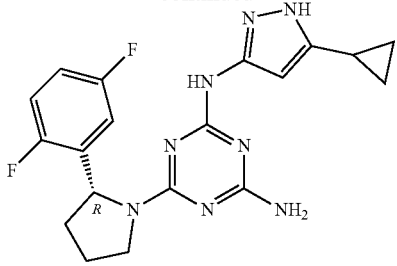
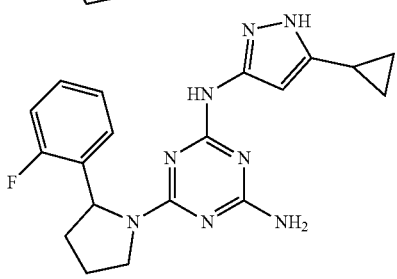
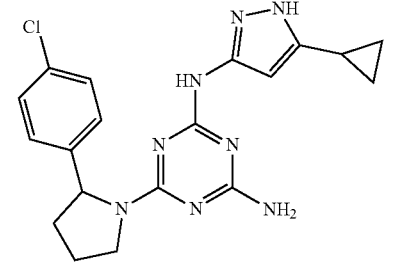
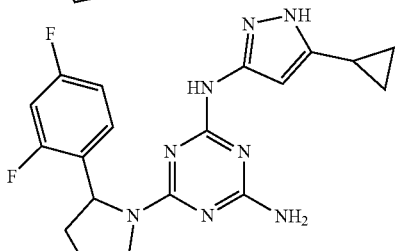
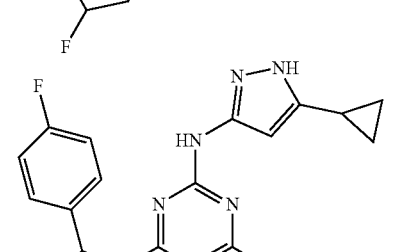
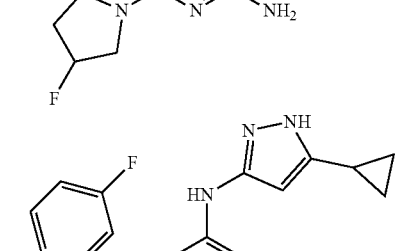
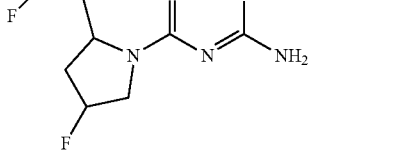

-continued
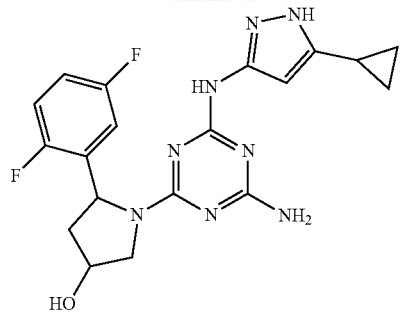
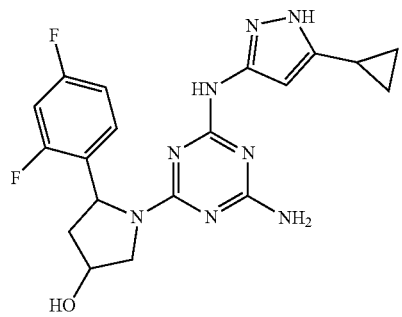
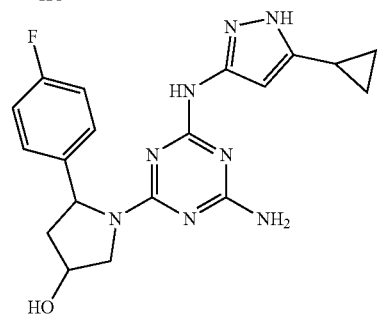
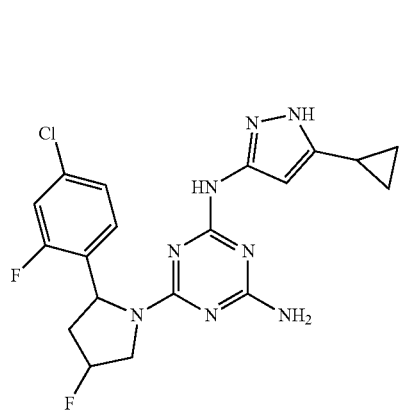
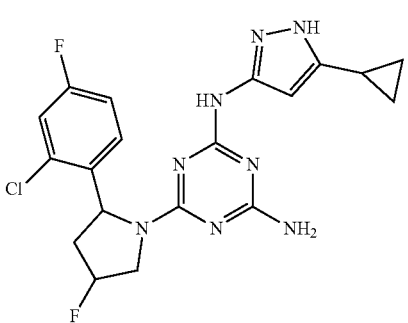
-continued
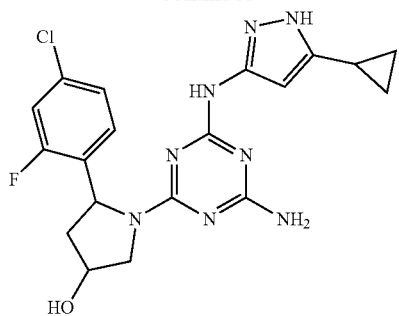
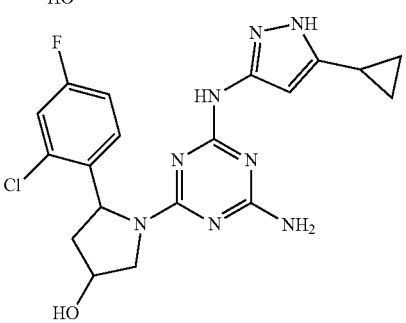
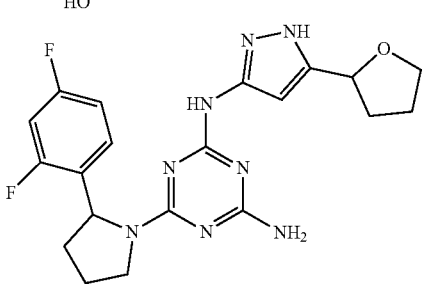
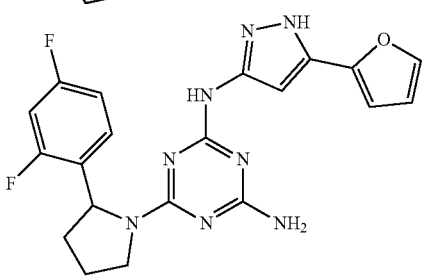
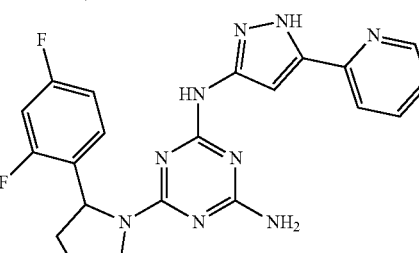
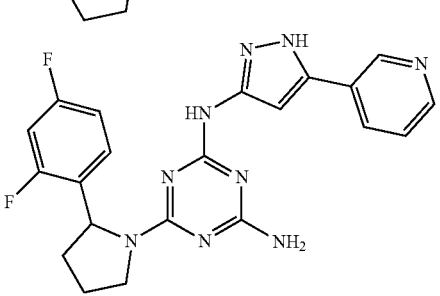

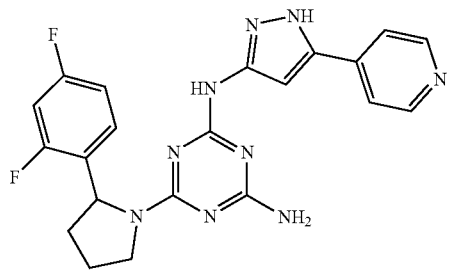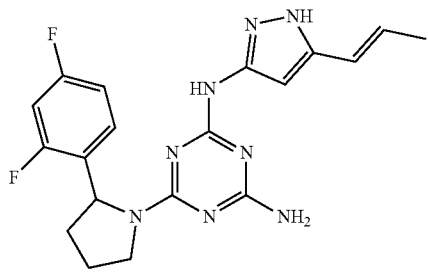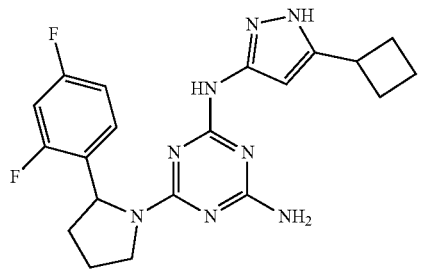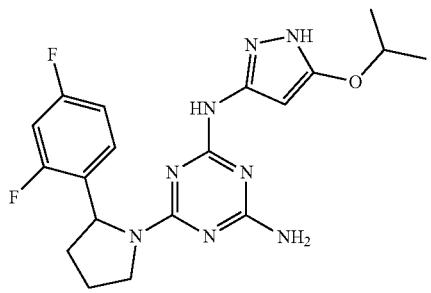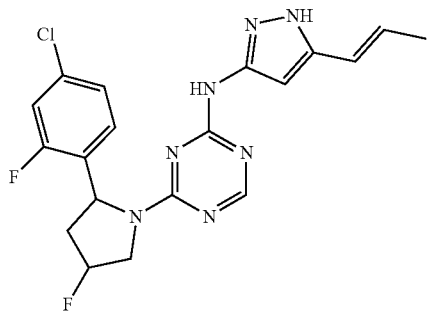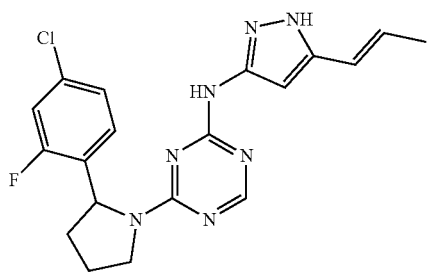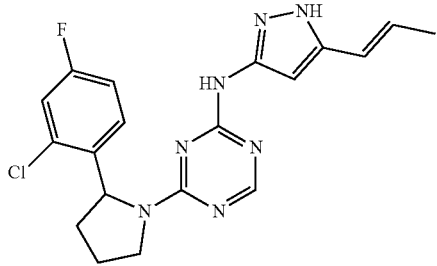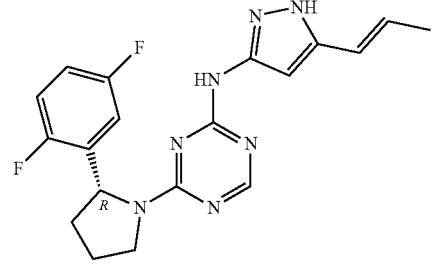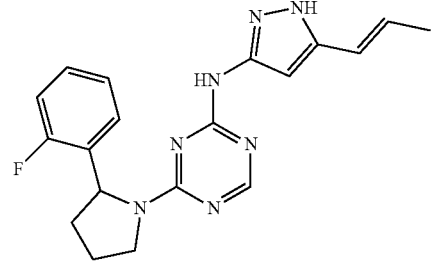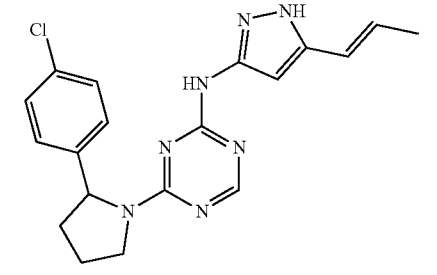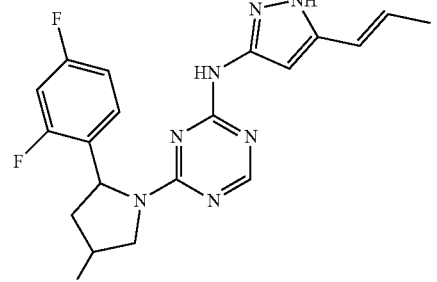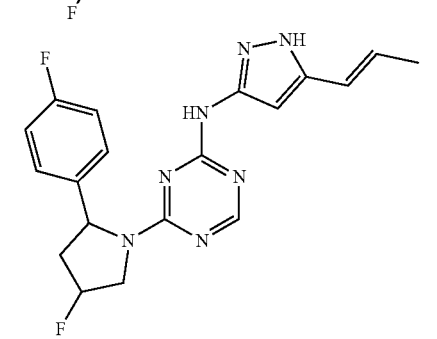

-continued
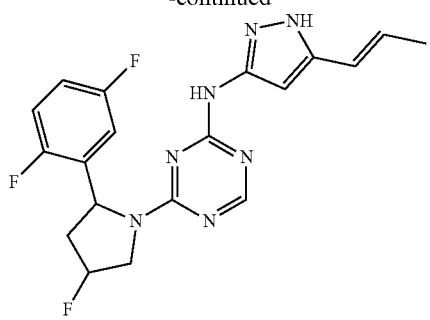
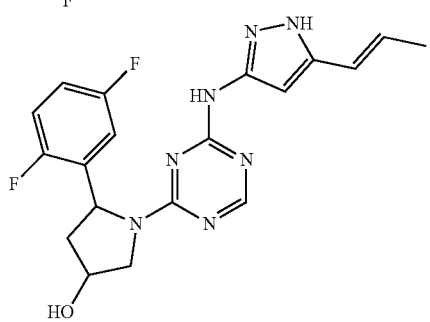
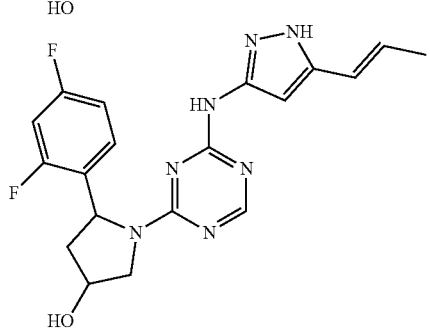
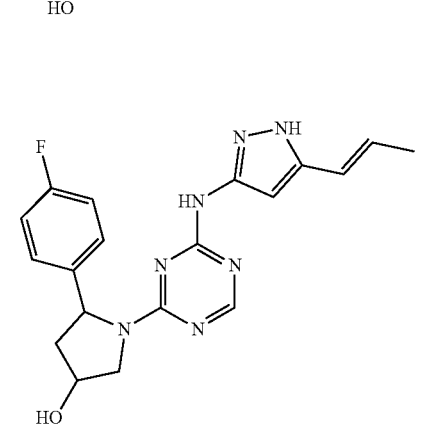
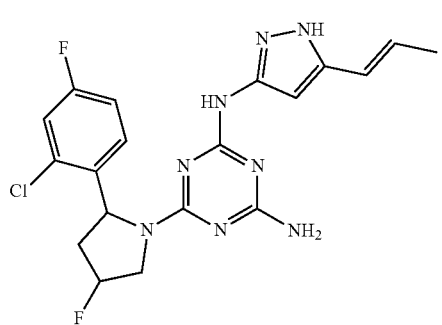
-continued
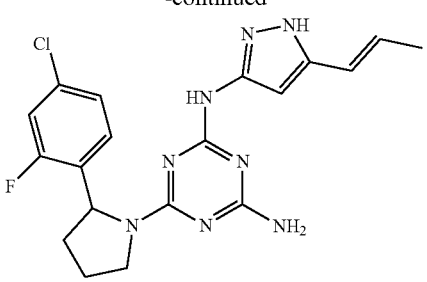
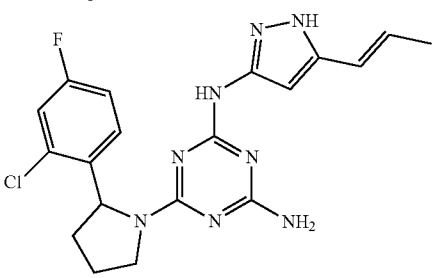
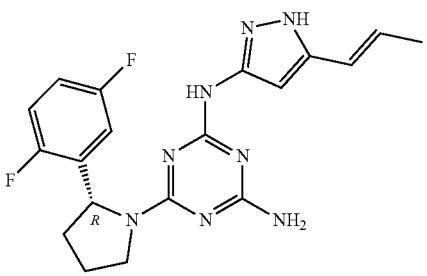
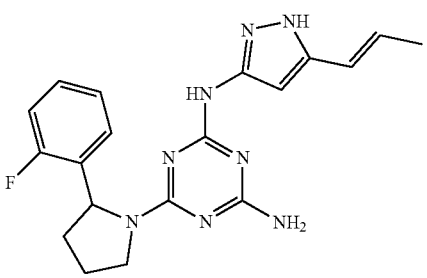
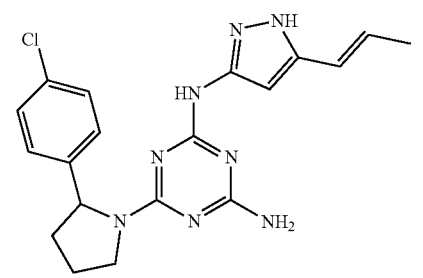
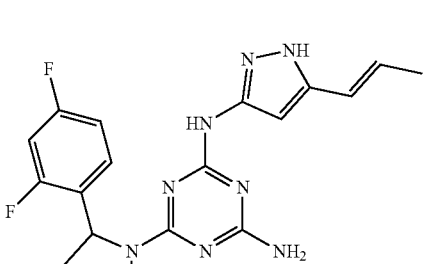

-continued

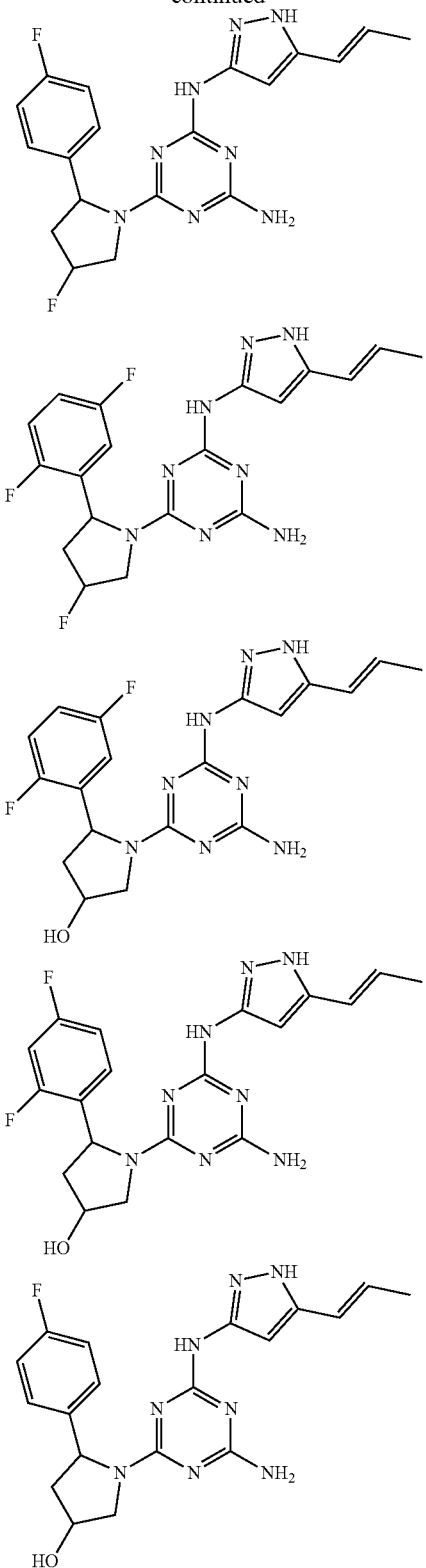

In another embodiment, a method of preparing the inventive compounds is provided. The compounds of the present invention can be generally prepared using 4,6-dichloropyrimidine, or 2-Amino-4,6-dichloropyrimidine, with various substituents on position "5". Compound (I) may contain various stereoisomers, geometric isomers, tautomeric isomers, and the like. All of possible isomers and their mixtures are included in the present invention, and the mixing ratio is not particularly limited.

By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

The compounds of Formula (I) may be prepared by use of known chemical reactions and procedures. The following general preparative methods are presented to aid one of skill in the art in synthesizing the inhibitors, with more detailed examples being presented in the experimental section describing the working examples.

Propenyl-pyrazol amine as defined in formula (II) is not commercially available. It can be prepared by several methods as described earlier (WO 2014071378) (incorporated herein by reference).

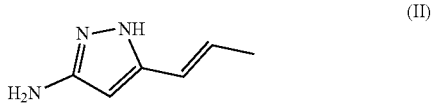

(II)

Precursors of substituted amines as defined in formula (III) can be purchased from suppliers, or synthesized from commercially available precursors using established protocols. (Journal of Medicinal Chemistry, 33(10), 2793-7; 1990; J. Med. Chem. 1987, 30, 1433; PCT Int. Appl., 2013088256, 20 Jun. 2013; U.S. Pat. Appl. Publ., 20160168156, 16 Jun. 2016)(each of which is incorporated herein by reference).

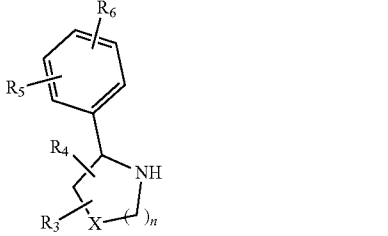

(III)

Precursors of 4,6-dichloro-pyrimidines as defined in formula (IVa) and 4,6-dichloro-1,3,5-triazine as defined in formula (IVb) can be purchased from suppliers, or prepared according to using established protocols (PCT Int. Appl., 2010144345, 16 Dec. 2010; PCT Int. Appl., 2010144338, 16 Dec. 2010; F PCT Int. Appl., 2010144359, 16 Dec. 2010) (each of which is incorporated herein by reference).

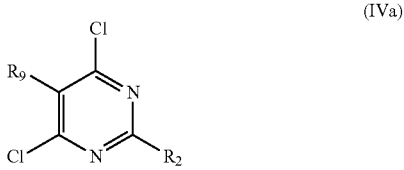

(IVa)

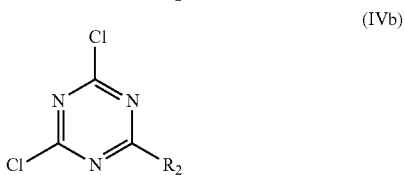

(IVb)

Generally, precursors of hetero-amine (Het-NHR$_1$) can be purchased from suppliers. Precursors of substituted pyrazol-amine as defined in formula (V), where "W" and "Z" has been described, but not limited to the part "substituted Het groups", can be purchased from suppliers.

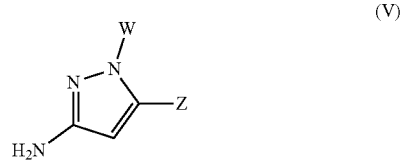

(V)

The preparation of the compounds of formula (I) in this invention can be carried out by methods listed in scheme 1.

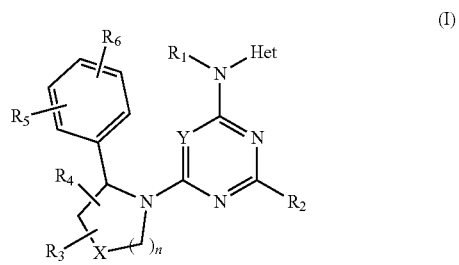

(I)

As shown in scheme 1, compound (I) can be synthesized by the reaction of 4,6-dichloropyrimidine, or 4,6-dichloro-1,3,5-triazine, with a sequence of substituted amine (III) to give monochloropyrimidine intermediate of compound b, which can react with hetero-amine (Het-NHR1) to produce the final compound (I). The reaction can be stepwise or in one pot. Alternative sequence can also be used to make pyrimidine derivatives.

Scheme 1

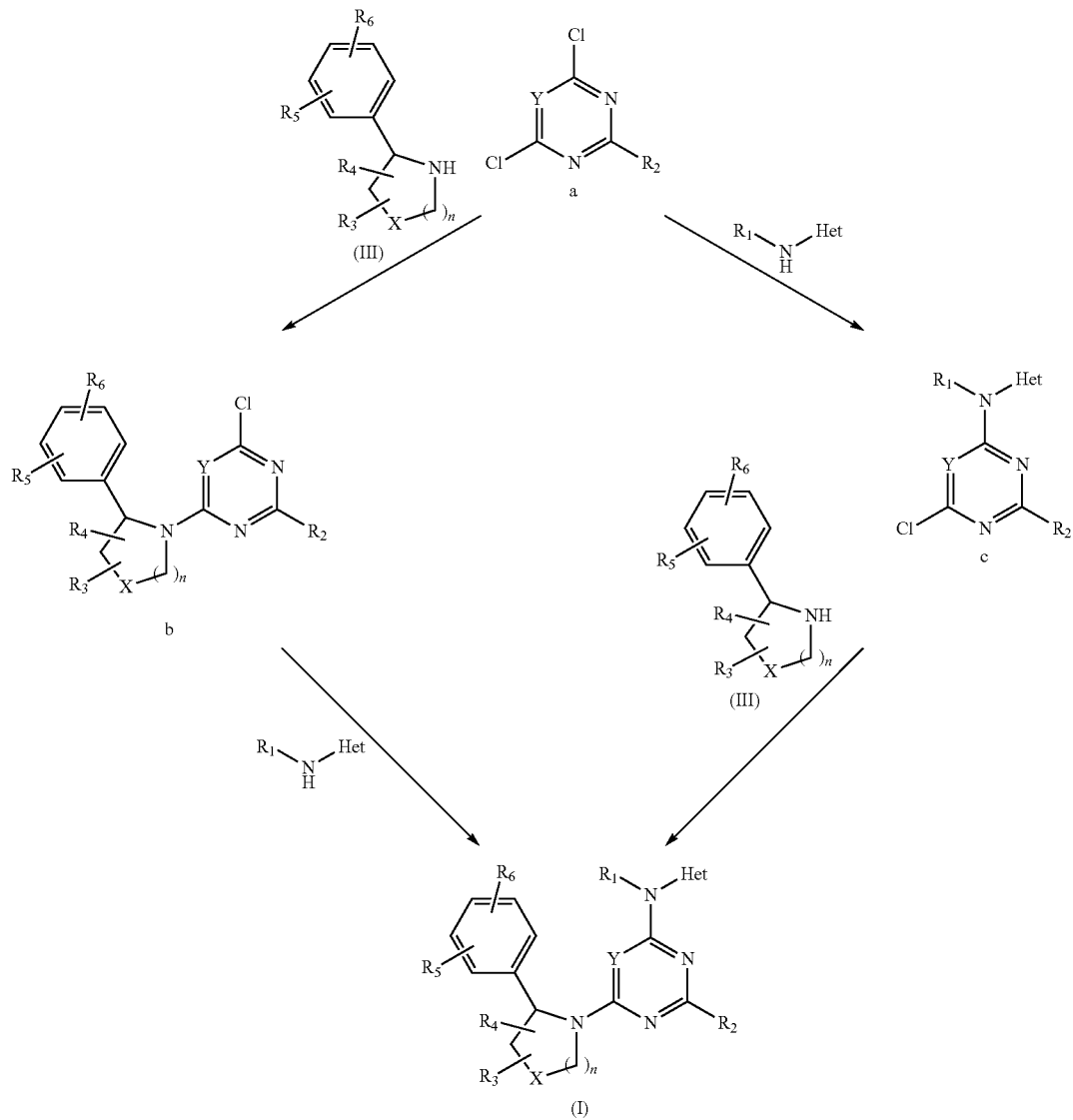

The reaction may be conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane. dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. For example, the reaction may be carried out the reaction at a temperature of from −50° C. to 200° C.

The present invention provides compositions of matter that are formulations of one or more active drugs and a pharmaceutically-acceptable carrier. In this regard, the invention provides a composition for administration to a mammalian subject, which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In certain embodiments, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, suitable methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing heterocyclic derivatives and methods useful for the in vivo delivery of heterocyclic derivatives in the form of nanoparticles, which are suitable for any of the aforesaid routes of administration.

U.S. Pat. Nos. 5,916,596, 6,506,405 and 6,537,579 (each of which is incorporated herein by reference) teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, for example, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

In accordance with the invention, the compounds of the invention may be used to treat diseases associated with undesired cellular proliferation or hyperproliferation, wherein the disease or condition is associated with a kinase, comprising identifying the mammal afflicted with said disease or condition and administering to said afflicted mammal a composition comprising the compound of formula 1.

The invention also provides methods of treating a mammal afflicted with the above diseases and conditions. The amount of the compounds of the present invention that may be combined with the carrier materials to produce a composition in a single dosage form will vary depending upon the host treated, the particular mode of administration. The compositions may be formulated so that a dosage of between 0.01-100 mg/kg body weight/day of the inhibitor can be administered to a patient receiving these compositions.

In one embodiment, the invention compounds are administered in combination with another active agent such as, for example, chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58) (incorporated herein by reference).

The exemplary therapeutic agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate ($NaHCO_3$) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to analyze the purity of triazine derivatives. HPLC was performed on a Phenomenex Synergi Polar-RP, 4 u, 80 A, 150×4.6 mm column using a vShimadzusystem equipted with SPD-M10A Phosphodiode Array Detector. Mobile phase A was water and mobile phase B was acetonitrile with a gradient from 20% to 80% B over 60 minutes and re-equilibrate at A/B (80:20) for 10 minutes. UV detection was at 220 and 54 nm.

Example 1

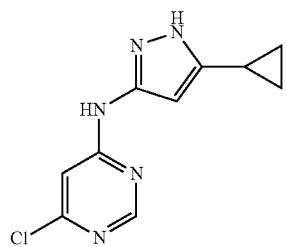

A solution of 5-cyclopropyl-1H-pyrazol-3-amine (17.50 g, 142.09 mmol) and 4,6-dichloropyrimidine (23.28 g, 156.30 mmol) in isopropanol (100 mL) was added DIPEA (49.50 mL, 36.73 g, 284.19 mmol). The mixture was stirred for 24 h in a RBF at 85° C. Isopropanol solvent was removed from the reaction mixture under reduced pressure and the residue was dissolved in DCM (200 mL). The solution was washed with $H_2O$ (2×150 mL) and the combined aqueous layer was extracted with 10% IPA/DCM. The organic layers were then combined, dried, and concentrated to afford yellow solids. This solid was triturated with DCM and collected by filtration to afford 6-chloro-N-(5-cyclopropyl-1H-pyrazol-3-yl)pyrimidin-4-amine compound 1 (23.3 g, 69.5%) as beige solid. $^1$H NMR (400 MHz, DMSO-d): δ 12.13 (bs, 1H), 10.13 (s, 1H), 8.40 (s, 1H), 7.39 (bs, 1H), 5.93 (bs, 1H), 1.85 (m, 1H), 0.90 (m, 2H), 0.66 (m, 2H). MS (ESI): Calcd. for $C_{10}H_{10}ClN_5$: 235, found 236 (MH$^+$).

Example 2

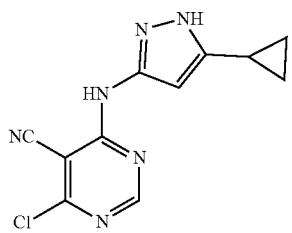

To a cold solution of 4,6-dichloropyrimidine-5-carbonitrile (500 mg, 2.87 mmol) in THF (10 mL) was added N,N-diisopropylethylamine (1.00 ml g, 5.75 mmol), followed by a solution of 3-cylopropyl-1-H-pyrazole amine (354 mg, 2.87 mmol) at 0° C. The resulting mixture was stirred at 0° C. for 2 hours. TLC was checked and the reaction was completed. After cooled to room temperature, half-saturated ammonium chloride in water (80 mL) was added and the mixture was stirred at room temperature for 15 min. The resulting solids were collected by filtration, washed by water to afford product compound 2 as yellow solids. (644 mg, 86% yield). $^1$H NMR (400 MHz, DMSO-$d_6$) δ 12.42 (br, 1H), 10.35 (br, 1H), 8.55 (s, 1H), 6.12 (s, 1H), 1.89 (m, 1H), 0.92 (m, 2H), 0.67 (m, 2H); ESI-MS: calcd for ($C_{11}H_9ClN_6$) 260, found 261 (MH$^+$).

Example 3

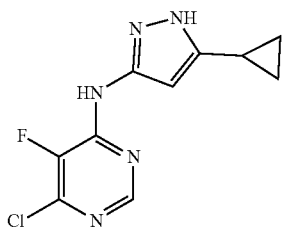

The solution of 4,6-dichloro-5-fluoropyrimidine (873 mg, 2.87 mmol), 3-cylopropyl-1-H-pyrazole amine (644 mg, 5.23 mmol) and N,N-diisopropylethylamine (2.28 m, 13.07 mmol) in THF (5 mL) was stirred at room temperature for overnight. TLC was checked and the reaction was completed. After removal of the solvents, the residue was triturated by half-saturated ammonium chloride in water (15 mL) and stirred at room temperature for 15 min. The resulting solids were collected by filtration, washed by water to afford compound 3 as beige solids. (1.15 g, 86% yield). $^1$H NMR (400 MHz, DMSO-$d_6$) δ 12.23 (br, 1H), 10.19 (br, 1H), 8.22 (s, 1H), 6.27 (s, 1H), 1.89 (m, 1H), 0.93 (m, 2H), 0.67 (m, 2H); ESI-MS: calcd for ($C_{10}H_9ClFN_5$) 253, found 254 (MH$^+$).

Example 4

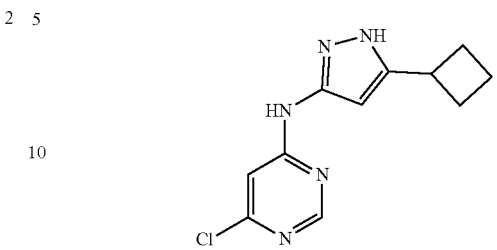

A solution of 4,6-dichloropyrimidine (542.96 mg, 3.64 mmol) and 5-cyclobutyl-1H-pyrazol-3-amine (500 mg, 3.64 mmol) in isopropanol (5 mL) was added DIPEA (1.90 mL, 1.41 g, 10.93 mmol). The mixture was stirred for 18 h in a sealed tube at 85° C. The reaction mixture was quenched with half-saturated NH4Cl solution and extracted with 10% IPA/DCM (3×50 mL). The combined organic extracts were dried over anhydrous $Na_2SO_4$ and concentrated in vacuo to obtain compound 4 as yellow oil (855 mg, 94%). The crude product was used for the next step without further purification. MS (ESI): Calcd. for $C_{11}H_{12}ClN_5$: 249, found 250 (MH$^+$).

Example 5

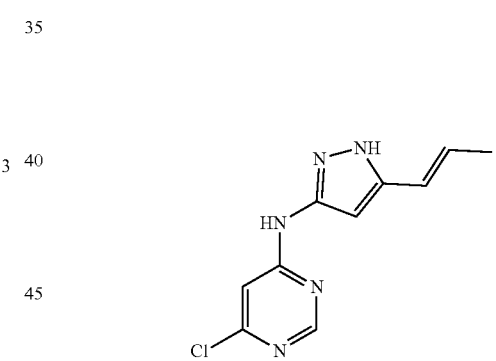

A solution of 4,6-dichloropyrimidine (604.80 mg, 4.06 mmol) and (E)-5-(prop-1-en-1-yl)-1H-pyrazol-3-amine (500 mg, 4.06 mmol) in isopropanol (5 mL) was added DIPEA (2.12 mL, 1.57 g, 12.18 mmol). The mixture was stirred for 18 h in a sealed tube at 85° C. The reaction mixture was quenched with half-saturated NH4Cl solution and extracted with 10% IPA/DCM (3×50 mL). The combined organic extracts were dried over anhydrous $Na_2SO_4$ and concentrated in vacuo to obtain compound 5 as yellow oil (905 mg, 95%). The crude product was used for the next step without further purification. MS (ESI): Calcd. for $C_{10}H_{10}ClN_5$: 235, found 236 (MH$^+$).

Example 6

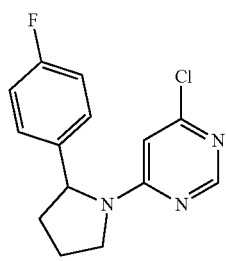

6

A solution of 4,6-dichloropyrimidine (450.86 mg, 3.03 mmol) and 2-(4-fluorophenyl)pyrrolidine (500.00 mg, 3.03 mmol) in isopropanol (~5 mL) was added DIPEA (1.58 mL, 9.08 mmol). The solution was stirred for 5 h at rt. $H_2O$ (50 mL) was added to the cooled solution and extracted with 10% MeOH/DCM (3×50 mL). The combined organic extracts were dried over anhydrous $Na_2SO_4$ and concentrated in vacuo to afford 4-chloro-6-(2-(4-fluorophenyl)pyrrolidin-1-yl)pyrimidine compound 6 (806 mg, 96%) as beige solids. The crude product was used in the next step without further purification. MS (ESI): Calcd. for $C_{14}H_{13}ClFN_3$: 277, found 278 ($MH^+$).

Example 7

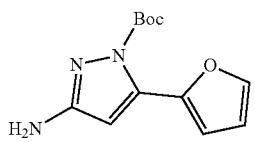

7

To a cold solution of 5-amino-3-(2-furyl)pyrazole (1.00 g g, 6.70 mmol) in THF (20 ml) was added a suspension of sodium hydride (60% in mineral oil, 322 mg, 8.05 mmol) in THF (6 ml) at 0° C. slowly. After stirring at 0° C. for 30 minute, di-tert-butyldicarboxate (1.61 g, 7.38 mmol) was added. The mixture was stirred at 0° C. for 75 minutes. TLC was checked and the starting material was consumed. The reaction mixture was quenched with ice-water, extracted with ethyl acetate/Hexane (90/10, 25 ml×2). The combined organic was washed by brine, dried over sodium sulfate and concentrated. The residue was triturated with EtOAc (5 ml)-Hexanes (30 ml). The yellow solids were collected by filtration, washed by hexanes to give compound 7 (1.41 g, 84% yield). $^1H$ NMR (400 MHz, DMSO-$d_6$) δ: 7.69 (m, 1H), 6.77 (m, 1H), 6.53 (m, 1H), 6.40 (br, 2H), 5.56 (s, 1H), 1.55 (s, 9H).

Example 8

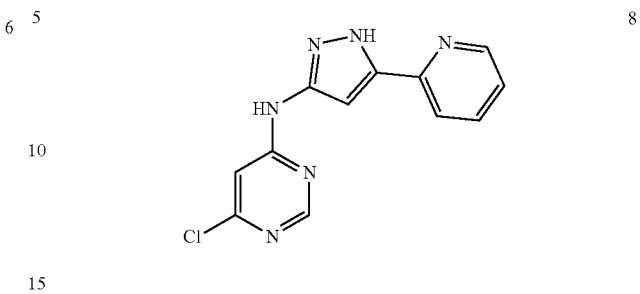

8

A solution of 4,6-dichloropyrimidine (69.75 mg, 0.468 mmol) and 5-(pyridin-2-yl)-1H-pyrazol-3-amine (75.00 mg, 0.468 mmol) in isopropanol (2.5 mL) was added DIPEA (0.24 mL, 1.40 mmol). The mixture was stirred for overnight in a sealed tube at 100° C. Solid formation was observed. The solid was then filtered off, washed, and dried to obtain 6-chloro-N-(5-(pyridin-2-yl)-1H-pyrazol-3-yl)pyrimidin-4-amine compound 8 (65 mg, 51%) as beige solid. $^1H$ NMR (400 MHz, DMSO-d): δ 13.16 (bs, 1H), 10.40 (s, 1H), 8.62 (m, 1H), 8.50 (s, 1H), 7.89 (m, 3H), 7.37 (m, 1H), 6.90 (br, 1H); MS (ESI): Calcd. for $C_{12}H_9ClN_6$: 272, found 273 ($MH^+$).

Example 9

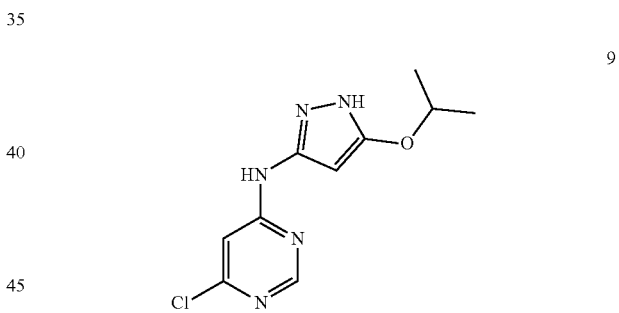

9

To a solution of 4,6-dichloropyrimidine (277 mg, 1.86 mmol) in iPrOH (10 mL) was added 5-Isopropoxy-1H-pyrazol-3-amine (250 mg, 1.77 mmol) and N,N-diisopropylethylamine (0.46 ml, 2.66 mmol) at room temperature. The reaction was stirred at 100° C. for overnight. TLC was checked and the reaction was completed. The solvents were removed under reduced pressure. The crude product was purified by column chromatography (0-10% MeOH in DCM) to give compound 9 as yellow solids (117 mg, 26%). $^1H$ NMR (400 MHz, DMSO-$d_6$) δ 11.98 (br, 1H), 10.10 (br, 1H), 8.41 (s, 1H), 7.00 (br, 1H), 5.60 (br, 1H), 4.50 (m, 1H), 1.28 (d, J=6.4 Hz, 6H); ESI-MS: calcd for $C_{10}H_{12}ClN_5O$ 253, found 254 ($MH^+$).

Example 10

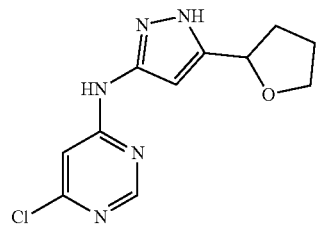

To a solution of 4,6-dichloro-pyrimidine (122 mg, 0.82 mmol) in iPrOH (5 mL) was added 3-(oxolan-2-yl)-1H-pyrazol-5-amine (100 mg, 0.65 mmol) and N,N-diisopropylethylamine (0.23 ml, 1.31 mmol) at room temperature. The reaction was stirred at 85° C. for overnight. TLC was checked and the reaction was completed. The solvents were removed under reduced pressure. The crude product was purified by column chromatography (0-10% MeOH in DCM) to give compound 10 as yellow solids (108 mg, 62%). $^1$H NMR (400 MHz, DMSO-$d_6$) δ 12.41 (s, 1H), 10.24 (br, 1H), 8.44 (s, 1H), 7.30 (br, 1H), 6.10 (br, 1H), 4.87 (m, 1H), 3.80 (m, 2H), 2.30-1.90 (m, 4H); ESI-MS: calcd for ($C_{11}H_{12}ClN_5O$) 265, found 266 (MH$^+$).

Example 11

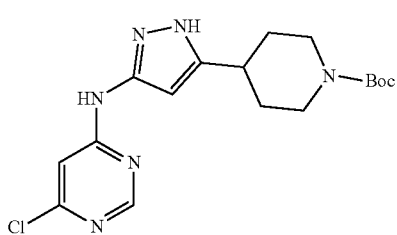

To a solution of 4,6-dichloropyrimidine (175 mg, 1.17 mmol) in iPrOH (10 mL) was added 4-(5-Amino-1H-pyrazol-3-yl)-piperidine-1-carboxylicacid tert-butyl ester (250 mg, 0.94 mmol) and N,N-diisopropylethylamine (0.33 ml, 1.88 mmol) at room temperature. The reaction was stirred at 85° C. for overnight. TLC was checked and the reaction was completed. The solvents were removed under reduced pressure. The crude product was purified by column chromatography (0-10% MeOH in DCM) to give compound 11 as yellow solids (278 mg, 78%). $^1$H NMR (400 MHz, DMSO-$d_6$) δ 12.20 (s, 1H), 10.20 (br, 1H), 8.42 (s, 1H), 7.30 (br, 1H), 6.10 (br, 1H), 4.00 (m, 2H), 2.80 (m, 3H), 1.90 (m, 2H), 1.50 (m, 2H), 1.41 (s, 9H); ESI-MS: calcd for ($C_{17}H_{23}ClN_6O_2$) 378, found 379 (MH$^+$).

Example 12

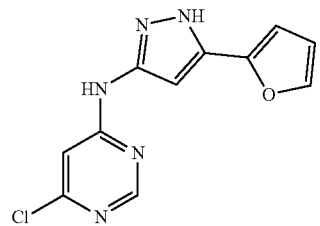

To a solution of 4,6-dichloro-pyrimidine (524 mg, 3.52 mmol) in iPrOH (18 mL) was added 5-Amino-3-(2-furyl) pyrazole (500 mg, 3.35 mmol) and N,N-diisopropylethylamine (0.88 ml, 5.03 mmol) at room temperature. The reaction was stirred at 100° C. for overnight. TLC was checked and the reaction was completed. The solvents were removed under reduced pressure. The crude product was purified by column chromatography (0-10% MeOH in DCM) to give compound 12 as yellow solids (333 mg, 38%). $^1$H NMR (400 MHz, DMSO-$d_6$) δ 12.97 (s, 1H), 10.38 (br, 1H), 8.49 (s, 1H), 7.77 (s, 1H), 7.30 (br, 1H), 7.00-6.40 (m, 3H); ESI-MS: calcd for ($C_{11}H_8ClN_5O$) 261, found 262 (MH$^+$).

Example 13

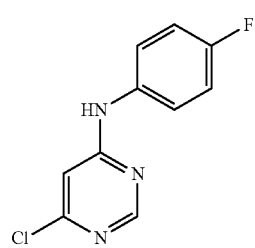

The solution of 4,6-dichloro-5-fluoropyrimidine (600 mg, 4.03 mmol), 4-fluoroaniline (542 mg, 4.83 mmol) and potassium carbonate (1.67 g, 12.08 mmol) in DMSO (5 mL) was heated at 80° C. with Biotage microwave initiator for 30 min. The reaction mixture was added to half-saturated ammonium chloride in water (80 mL) and stirred for 30 min. The solids were collected by filtration, washed by water to afford compound 13 as yellow solids (513 mg, 57% yield). No further purification was performed and the product was used directly for the next step reaction. $^1$H NMR (400 MHz, DMSO-$d_6$) δ 9.87 (s, 1H), 8.45 (s, 1H), 7.62 (m, 2H), 7.19 (m, 2H), 6.75 (s, 1H); ESI-MS: calcd for ($C_{10}H_7ClFN_3$) 223, found 224 (MH$^+$).

Example 14

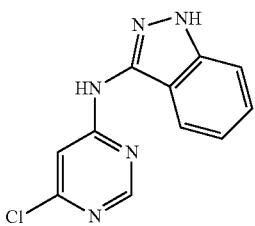

14

A solution of 4,6-dichloropyrimidine (559.40 mg, 3.76 mmol) and 1H-indazol-3-amine (500 mg, 3.76 mmol) in isopropanol (5 mL) was added DIPEA (1.90 mL, 1.41 g, 10.93 mmol). The mixture was stirred for 18 h in a sealed tube at 85° C. Solvent IPA was removed under reduced pressure and the crude residue was purified by column chromatography on silica gel using 10-30% EtOAc in Hexane to obtain 330 mg (36%) of the desired compound 14 as beige solid. $^1$H NMR (400 MHz, DMSO-d): δ 12.64 (s, 1H), 10.73 (s, 1H), 8.53 (s, 1H), 8.02 (d, J=8 Hz, 1H), 7.83 (br, 1H), 7.49 (m, 1H), 7.38 (m, 1H), 7.09 (m, 1H). MS (ESI): Calcd. for $C_{11}H_8ClN_5$: 245, found 246 (MH$^+$).

Example 15

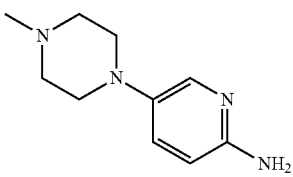

15

A solution of 1-methyl-4-(6-nitro-pyridin-3-yl)-piperazine (2.60 g, 11.70 mmol) in methanol (120 mL) was hydrogenated in the presence of 10% Pd/C (0.3 g) using an H$_2$ balloon. After 16 h, the reaction mixture was filtered through a pad of Celite and rinsed with methanol (3×20 mL). The filtrate was concentrated to afford the title compound 15 (2.31 g, 100%) as pink solids. The product was used directly for the next step reaction without further purification. $^1$H NMR (400 MHz, DMSO-d6) δ 7.58 (d, J=2.8 Hz, 1H), 7.15 (dd, J=8.8 Hz, 2.8 Hz, 1H), 6.38 (d, J=8.8 Hz, 1H), 5.36 (br, 2H), 2.91 (m, 4H), 2.43 (m, 4H), 2.19 (s, 3H; ESI-MS: calcd for $C_{10}H_{16}N_4$) 192, found 193 (MH$^+$).

Example 16

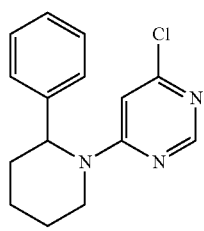

16

A solution of 4,6-dichloropyrimidine (461.94 mg, 3.10 mmol) and 2-phenylpiperidine (500.00 mg, 3.10 mmol) in isopropanol (~5 mL) was added DIPEA (1.62 mL, 9.30 mmol). The solution was stirred for 5 h at rt. H$_2$O (50 mL) was added to the cooled solution and extracted with 10% MeOH/DCM (3×50 mL). The combined organic extracts were dried over anhydrous Na$_2$SO$_4$ and concentrated in vacuo to afford 4-chloro-6-(2-phenylpiperidin-1-yl)pyrimidine compound 16 (750 mg, 88%) as white solid. The crude product was used in the next step without further purification. MS (ESI): Calcd. for $C_{15}H_{16}ClN_3$: 273, found 274 (MH$^+$).

Example 17

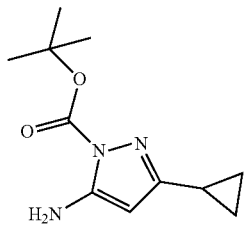

17

A solution of 3-cyclopropyl-1-H-pyrazole-5-amine (3.05 g, 24.77 mmol) in THF (20 ml) was added to a cold suspension of sodium hydride (60% in mineral oil, 1.09 g, 27.24 mmol) in THF (20 ml) at 0° C. slowly. After stirring at 0° C. for 30 minute, di-tert-butyldicarboxate (5.95 g, 27.24 mmol) was added. (THF was used to help the addition of di-tert-butyldicarboxate, total 125 mL was in the bottle). The mixture was stirred at 0° C. for 30 minute. TLC was checked and the starting material was consumed. The reaction mixture was quenched with ice-water, extracted with ethyl acetate (3×50 ml). The combined organic was washed by brine, dried over sodium sulfate and concentrated to minimum amount solvents. Hexanes were added (~100 ml), and the mixture was sonicated to make a homogenous suspension. The yellow solids were collected by filtration, washed by hexanes to give compound 17 as a mixture of 2 isomers (about 1:3) of protection group on the ring (3.73 g, 69% yield). $^1$H NMR (400 MHz, DMSO-d$_6$) δ: for the major isomer: 6.16 (br, 2H), 4.92 (s, 1H), 1.68 (m, 1H), 1.49 (s, 9H), 0.86 (m, 2H), 0.78 (m, 2H); for the minor isomer: 5.35 (s, 1H), 5.20 (br, 2H), 2.05 (m, 1H), 1.49 (s, 9H), 0.88 (m, 2H), 0.78 (m, 2H).

Example 18

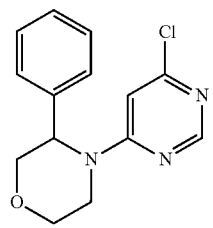

18

A solution of 4,6-dichloropyrimidine (148.97 mg, 0.77 mmol) and 3-phenylmorpholine (125.00 mg, 0.77 mmol) in isopropanol (~3 mL) was added DIPEA (0.40 mL, 2.30 mmol). The solution was stirred for 5 h at rt. H$_2$O (50 mL) was added to the cooled solution and extracted with 10% MeOH/DCM (3×50 mL). The combined organic extracts were dried over anhydrous Na$_2$SO$_4$ and concentrated in vacuo to afford 4-(6-chloropyrimidin-4-yl)-3-phenylmorpholine compound 18 (171 mg, 81%) as thick yellow liquid. The crude product was used in the next step without further purification. MS (ESI): Calcd. for C$_{14}$H$_{14}$ClN$_3$O: 275, found 276 (MH$^+$).

Example 19

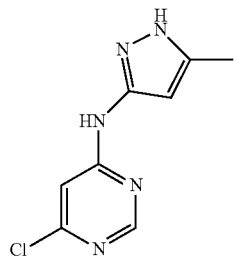

19

A solution of 5-methyl-1H-pyrazol-3-amine (250 mg, 2.57 mmol) and 4,6-dichloropyrimidine (422 mg, 2.83 mmol) in isopropanol (5 mL) was added DIPEA (1.35 mL, 7.72 mmol). The mixture was stirred for 18 h at rt followed by another 5 h at 50° C. After cooling down to rt, precipitation of solids was observed. The solids were filtered, washed with ice-cold isopropanol and dried under vacuum to obtain 205 mg (38%) of compound 19 as beige solids. The product was used to the next step without further purification. $^1$H NMR (400 MHz, DMSO-d): δ 12.10 (bs, 1H), 10.16 (s, 1H), 8.42 (s, 1H), 7.44 (bs, 1H), 6.02 (bs, 1H), 2.21 (s, 3H); MS (ESI): Calcd. for (C$_8$H$_8$ClN$_5$): 209, found 210 (MH$^+$).

Example 20

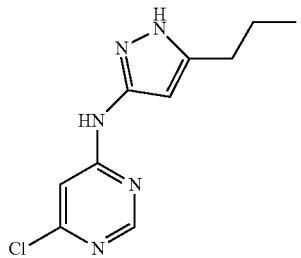

20

A solution of 5-propyl-1H-pyrazol-3-amine (250 mg, 2.00 mmol) and 4,6-dichloropyrimidine (327 mg, 2.20 mmol) in isopropanol (5 mL) was added DIPEA (1.04 mL, 5.99 mmol). The mixture was stirred for 18 h at rt followed by another 18 h at 50° C. The crude reaction mixture was concentrated and the residue was dissolved in DMSO (2 mL). The solution was then added to half-saturated ammonium chloride in water (50 mL) and stirred for 30 min. The solids were collected by filtration, washed by water and dried to obtain compound 20 as beige solids (283 mg, 60% yield). $^1$H NMR (400 MHz, DMSO-d): δ 12.13 (bs, 1H), 10.18 (s, 1H), 8.43 (s, 1H), 7.59 (bs, 1H), 6.07 (bs, 1H), 2.49 (m, 2H), 1.59 (m, 2H), 0.90 (m, 3H); MS (ESI): Calcd. for (C$_{10}$H$_{10}$ClN$_5$) 237, found 238 (MH$^+$).

Example 21

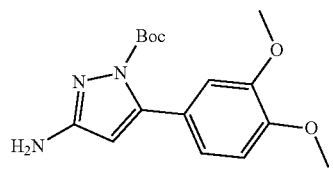

21

To a cold solution of 3-(3,4-dimethoxyphenyl)-1H-pyrazol-5-amine (1.00 g, 4.56 mmol) in THF (25 ml) was added a suspension of sodium hydride (60% in mineral oil, 228 mg, 5.70 mmol) in THF (15 ml) at 0° C. slowly. After stirring at 0° C. for 60 minute, di-tert-butyldicarboxate (1.11 g, 5.11 mmol) was added. (5 ml THF was used to help the addition of di-tert-butyldicarboxate). The mixture was stirred at 0° C. for 60 minute. TLC was checked and the starting material was consumed. The reaction mixture was quenched with ice-water, extracted with ethyl acetate (3×15 ml). The combined organic was washed by brine, dried over sodium sulfate and concentrated to give slurry residue, which become solid overnight at room temperature. 5% EtOAc in Hexanes were added (~15 ml), and the mixture was sonicated to make a homogenous suspension. The solids were collected by filtration and washed by hexanes (2 ml) to give the desired product compound 21 as yellow solids (1.23 g, 84% yield). $^1$H NMR (400 MHz, DMSO-d$_6$) δ: 7.29 (m, 2H), 6.97 (d, J=8.8 Hz, 1H), 6.37 (br, 2H), 5.73 (s, 1H), 3.80 (s, 3H), 3.78 (s, 3H), 1.59 (s, 9H).

Example 22

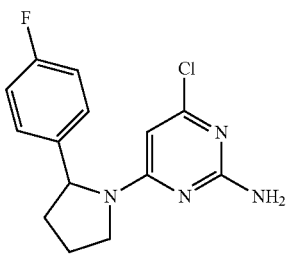

22

To a solution of 2-amino-4,6-dichloropyrimidine (496 mg, 3.03 mmol) in DMSO (5 mL) was added 2-(4-fluorophenyl)pyrrolidine (500 mg, 3.03 mmol) and N,N-diisopropylethylamine (1.05 ml, 6.05 mmol) at room temperature. The reaction was stirred at 85° C. for overnight. After the reaction, the mixture was added half-saturated NH$_4$Cl in water (75 ml) and the mixture was stirred at room temperature for 30 min. the mixture was cooled with ice bath and the solids were collected by filtration, washed by water and air-dried for overnight to obtain compound 22 as yellow solids (871 mg, 99%). $^1$H NMR (400 MHz, DMSO-d$_6$) δ 7.18 (m, 4H), 6.60-6.20 (br, 2H), 5.32 (br, 1H), 4.90 (br, 1H), 3.80-3.50 (m, 2H), 2.30 (br, 1H), 2.00-1.60 (br, 3H); ESI-MS: calcd for ($C_{14}H_{14}ClFN_4$) 292, found 293 ($MH^+$).

Example 23

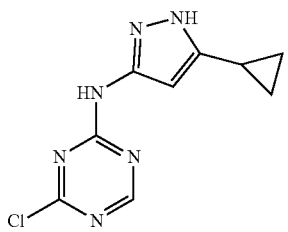

23

To a cold solution of 2,4-dichloro-1,3,5-triazine (2.50 g, 16.67 mmol) in DMF (20 mL) was added a solution of 3-cylopropyl-1-H-pyrazole amine (2.16 g, 17.50 mmol) and N,N-diisopropylethylamine (3.49 ml, 20.00 mmol) in DMF (15 mL) dropwise at 0° C. After addition, the reaction mixture was stirred at 0° C. for 3 hours. TLC was checked and the starting material was consumed. The reaction mixture was added to half-sat. $NH_4Cl$ in water (500 ml) and the mixture was stirred at 0° C. for 30 min. The solids were collected by filtration, washed by water and dried by air. The product compound 23 was obtained as yellow solids (3.55 g, 89% yield). No further purification was conducted. $^1$H NMR (400 MHz, DMSO-$d_6$) δ 12.26 (s, 1H), 10.90 (br, 1H), 8.57 (br, 1H), 6.23 (br, 1H), 1.90 (m, 1H), 0.92 (m, 2H), 0.68 (m, 2H); ESI-MS: calcd for ($C_9H_9ClN_6$) 236, found 237 ($MH^+$).

Example 24

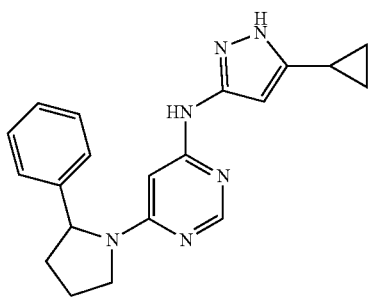

24

To a solution of compound 1 (100 mg, 0.42 mmol) in DMSO (2.5 mL) was added 2-phenylpyrrolidine (68.71 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated $NH_4Cl$ (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 24 as beige solid (93 mg, 63%). $^1$H NMR (400 MHz, DMSO-$d_6$) δ 11.85 (br, 1H), 8.98 (br, 1H), 7.99 (br, 1H), 7.35-7.10 (m, 5H), 5.68 (br, 1H), 5.02 (br, 1H), 3.71 (m, 2H), 2.34 (m, 1H), 2.08-1.80 (m, 4H), 0.89 (m, 2H), 0.61 (m, 2H); ESI-MS: calcd for ($C_{20}H_{22}N_6$) 346, found 347 ($MH^+$).

Example 25

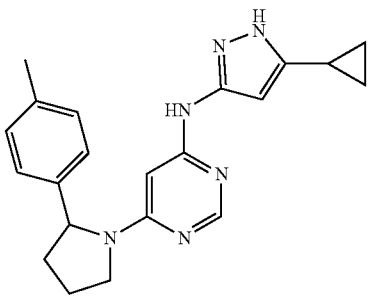

25

To a solution of compound 1 (100 mg, 0.42 mmol) in 1,4-Dioxane (4 mL) was added 2-(p-tolyl)pyrrolidine (82.10 mg, 0.51 mmol), TBAI (313.5 mg, 0.84 mmol) and DIPEA (0.11 mL, 0.64 mmol) at room temperature and the mixture was stirred at 105° C. for overnight and for another 4 h at 150° C. Water (50 mL) was added and the mixture was extracted with DCM (3×50 mL). The combined organic extracts was washed by brine, dried over sodium sulfate and concentrated. The resulting crude product was purified by flash column chromatography on silica gel using 0-5% MeOH in DCM (v/v) as eluent to provide compound 25 as yellow solids (50 mg, 33%). $^1$H NMR (400 MHz, DMSO-$d_6$) δ 11.85 (br, 1H), 8.95 (br, 1H), 7.99 (br, 1H), 7.08 (m, 4H), 5.68 (br, 1H), 3.6 (m, 1H), 2.25-1.80 (m, 9H), 0.90 (m, 2H), 0.61 (m, 2H); ESI-MS: calcd for ($C_{21}H_{24}N_6$) 360, found 361 ($MH^+$).

Example 26

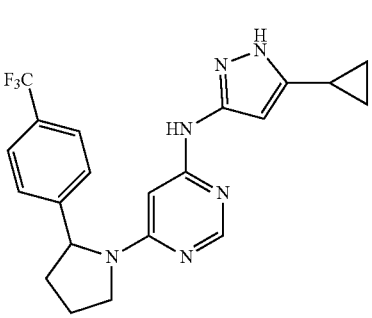

26

To a solution of compound 1 (150 mg, 0.64 mmol) in iPA (2.5 mL) was added 2-(4-(trifluoromethyl)phenyl)pyrrolidine (150.68 mg, 0.70 mmol), and DIPEA (0.17 mL, 0.95 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 26 as white solid (136 mg, 52%). $^1$H NMR (400 MHz, DMSO-$d_6$) δ 11.87 (br, 1H), 9.07 (br, 1H), 7.99 (br, 1H), 7.67 (d, J=8.0 Hz, 2H), 7.39 (d, J=8.4 Hz, 2H), 5.71 (br, 1H), 5.02 (br, 1H), 3.72 (m, 2H), 2.39 (m, 1H), 2.08-1.80

(m, 4H), 0.89 (m, 2H), 0.62 (m, 2H); ESI-MS: calcd for (C₂₁H₂₁F₃N₆) 414, found 415 (MH⁺).

Example 27

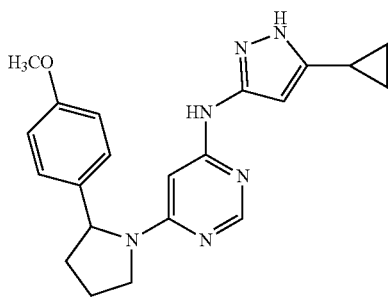

To a solution of compound 1 (100 mg, 0.42 mmol) in DMSO (2.5 mL) was added 2-(4-methoxyphenyl)pyrrolidine (82.73 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated NH₄Cl (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 27 as beige solid (103 mg, 64%). ¹H NMR (400 MHz, DMSO-d₆) δ 11.85 (br, 1H), 8.96 (br, 1H), 8.00 (br, 1H), 7.08 (d, J=8.0 Hz, 2H), 6.86 (d, J=8.4 Hz, 2H), 5.68 (br, 1H), 5.02 (br, 1H), 3.71 (m, 5H), 2.31 (m, 1H), 2.08-1.80 (m, 4H), 0.89 (m, 2H), 0.61 (m, 2H); ESI-MS: calcd for (C₂₁H₂₄N₆O) 376, found 377 (MH⁺).

Example 28

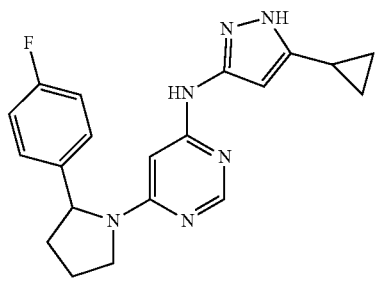

The solution of compound 1 (100 mg, 0.42 mmol), 2-(4-fluorophenyl)pyrrolidine (70 mg, 0.42 mmol) and DIPEA (0.11 ml, 0.63 mmol) DMSO (2.5 mL) was heated at 170° C. for 45 min. with a Biotage microwave initiator. TLC was checked and the starting material was almost consumed. The reaction mixture was added to half-saturated ammonium chloride in water (80 mL) and stirred for 30 min. The solids were collected by filtration, washed by water. The crude product was purified by column chromatography (0-10% MeOH in DCM) to give compound 28 as yellow solids. (74 mg, 48% yield). ¹H NMR (400 MHz, DMSO-d₆) δ 11.85 (s, 1H), 8.99 (s, 1H), 7.99 (s, 1H), 7.21-7.08 (m, 4H), 6.20 (b, 1H), 5.68 (s, 1H), 5.00 (br, 1H), 3.80-3.40 (br, 2H), 2.33 (m, 1H), 2.00-1.70 (m, 4H), 0.89 (m, 2H), 0.62 (m, 2H); ESI-MS: calcd for (C₂₀H₂₁FN₆) 364, found 365 (MH⁺).

Example 29

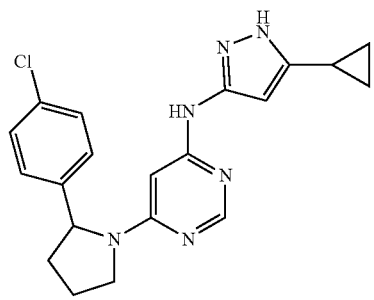

To a solution of compound 1 (100 mg, 0.42 mmol) in DMSO (2.5 mL) was added 2-(4-chlorophenyl)pyrrolidine (84.79 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated NH₄Cl (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 29 as beige solid (102 mg, 63%). ¹H NMR (400 MHz, DMSO-d₆) δ 11.87 (br, 1H), 9.03 (br, 1H), 7.99 (br, 1H), 7.35 (d, J=8.0 Hz, 2H), 7.19 (d, J=8.4 Hz, 2H), 5.68 (br, 1H), 5.02 (br, 1H), 3.70 (m, 2H), 2.34 (m, 1H), 2.08-1.80 (m, 4H), 0.90 (m, 2H), 0.62 (m, 2H); ESI-MS: calcd for (C₂₀H₂₁ClN₆) 380, found 381 (MH⁺).

Example 30

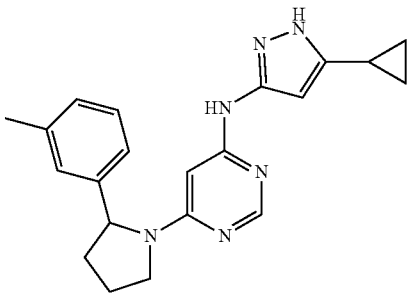

To a solution of compound 1 (100 mg, 0.42 mmol) in DMSO (2.5 mL) was added 2-(m-tolyl)pyrrolidine (75.26 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated NH₄Cl (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 30 as beige solid (36 mg, 24%). $^1$H NMR (400 MHz, DMSO-d$_6$) δ 11.85 (br, 1H), 8.98 (br, 1H), 8.00 (br, 1H), 7.17 (m, 1H), 6.97 (m, 3H), 5.69 (br, 1H), 5.02 (br, 1H), 3.71 (m, 2H), 2.32-2.65 (m, 4H), 2.08-1.80 (m, 4H), 0.89 (m, 2H), 0.61 (m, 2H); ESI-MS: calcd for (C$_{21}$H$_{24}$N$_6$) 360, found 361 (MH$^+$).

Example 31

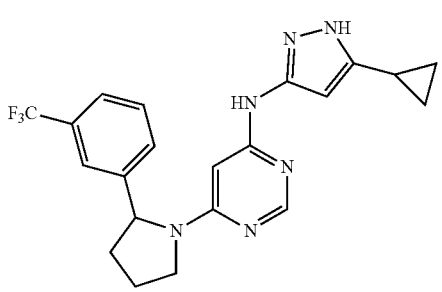

The solution of compound 1 (150 mg, 0.64 mmol), 2-[3-(trifluoromethyl)phenyl]pyrrolidine (157 mg, 0.73 mmol) and KF (110 mg, 1.91 mmol) DMSO (3.5 mL) was heated at 180° C. with Biotage microwave initiator for 1 h. The reaction mixture was added to half-saturated ammonium chloride in water (80 mL) and stirred for 30 min. The solids were collected by filtration, washed by water. The crude product was purified by column chromatography (0-10% MeOH in DCM) to give compound 31 as yellow solids (113 mg, 43% yield). $^1$H NMR (400 MHz, DMSO-d$_6$) δ 11.87 (s, 1H), 9.00 (s, 1H), 7.98 (s, 1H), 7.80-7.20 (m, 4H), 6.40 (br, 1H), 5.75 (s, 1H), 5.30 (br, 1H), 3.73 (s, 1H), 3.72 (br, 1H), 2.38 (m, 1H), 2.00-1.70 (m, 4H), 0.89 (m, 2H), 0.62 (m, 2H); ESI-MS: calcd for (C$_{21}$H$_{21}$F$_3$N$_6$) 414, found 415 (MH$^+$).

Example 32

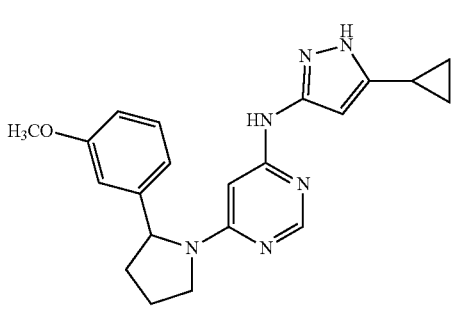

To a solution of compound 1 (100 mg, 0.42 mmol) in DMSO (2.5 mL) was added 2-(3-methoxyphenyl)pyrrolidine (82.73 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated NH$_4$Cl (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 32 as beige solid (42 mg, 26%). $^1$H NMR (400 MHz, DMSO-d$_6$) δ 11.85 (br, 1H), 8.98 (br, 1H), 8.00 (br, 1H), 7.17 (m, 1H), 6.68 (m, 3H), 5.69 (br, 1H), 5.02 (br, 1H), 3.71 (m, 5H), 2.32 (m, 1H), 2.08-1.80 (m, 4H), 0.89 (m, 2H), 0.61 (m, 2H); ESI-MS: calcd for (C$_{21}$H$_{24}$N$_6$0) 376, found 377 (MH$^+$).

Example 33

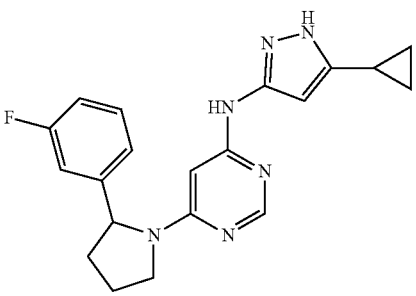

To a solution of compound 1 (150 mg, 0.64 mmol) in iPA (2.5 mL) was added 2-(3-fluorophenyl)pyrrolidine (115.67 mg, 0.70 mmol), and DIPEA (0.17 mL, 0.95 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 33 as white solid (95 mg, 41%). $^1$H NMR (400 MHz, DMSO-d$_6$) δ 11.87 (br, 1H), 9.03 (br, 1H), 7.99 (br, 1H), 7.34 (m, 1H), 7.02 (m, 3H), 5.72 (br, 1H), 5.02 (br, 1H), 3.72 (m, 2H), 2.34 (m, 1H), 2.08-1.80 (m, 4H), 0.87 (m, 2H), 0.63 (m, 2H); ESI-MS: calcd for (C$_{20}$H$_{21}$FN$_6$) 364, found 365 (MH$^+$).

Example 34

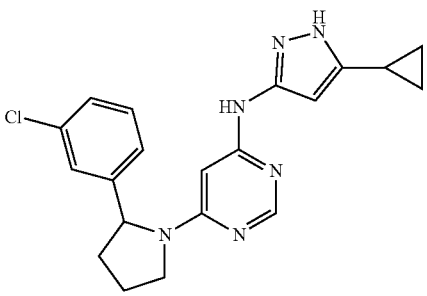

To a solution of compound 1 (100 mg, 0.42 mmol) in DMSO (2.5 mL) was added 2-(3-chlorophenyl)pyrrolidine (84.79 mg, 0.47 mmol), and DIPEA (0.11 mL, 0.64 mmol) at room temperature and the mixture was stirred at 120° C. for overnight. After cooling down to rt, the reaction mixture was slowly added to stirring water (~25 mL). Precipitation of solid was observed. Saturated NH₄Cl (~25 mL) and saturated NaCl (~25 mL) solution were added and the mixture was then stirred for another 30 mins. The solid was then filtered off and dried. The resulting crude solid was then purified by flash column chromatography on silica gel using 0-5% MeOH in DCM (v/v) as eluent to obtain compound 34 as beige solid (45 mg, 28%). ¹H NMR (400 MHz, DMSO-d₆) δ 11.87 (br, 1H), 9.05 (br, 1H), 7.99 (br, 1H), 7.18 (m, 4H), 5.69 (br, 1H), 5.02 (br, 1H), 3.71 (m, 2H), 2.33 (m, 1H), 2.08-1.80 (m, 4H), 0.89 (m, 2H), 0.62 (m, 2H); ESI-MS: calcd for (C₂₀H₂₁ClN₆) 380, found 381 (MH⁺).

Example 35

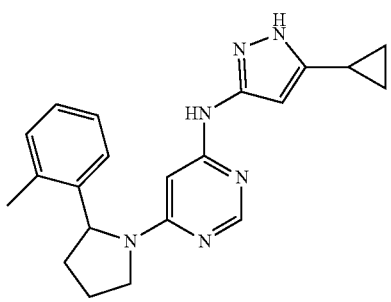

35

To a solution of compound 1 (125 mg, 0.53 mmol) in iPA (2.5 mL) was added 2-(o-tolyl)pyrrolidine (94.08 mg, 0.58 mmol), and DIPEA (0.14 mL, 0.80 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 35 as beige solid (146 mg, 76%). ¹H NMR (400 MHz, DMSO-d₆) δ 11.87 (br, 1H), 9.04 (br, 1H), 8.02 (br, 1H), 7.15-6.80 (m, 4H), 5.65 (br, 1H), 5.02 (br, 1H), 3.72 (m, 2H), 2.40 (m, 4H), 2.08-1.80 (m, 4H), 0.90 (m, 2H), 0.62 (m, 2H); ESI-MS: calcd for (C₂₁H₂₄N₆) 360, found 361 (MH⁺).

Example 36

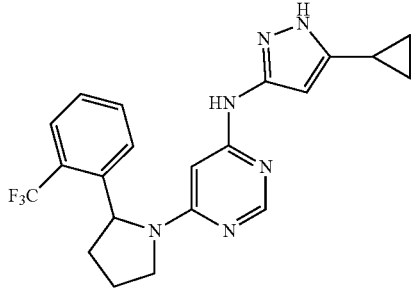

36

To a solution of compound 1 (150 mg, 0.64 mmol) in iPA (2.5 mL) was added 2-(2-(trifluoromethyl)phenyl)pyrrolidine (150.68 mg, 0.70 mmol), and DIPEA (0.17 mL, 0.95 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 36 as beige solid (122 mg, 46%). ¹H NMR (400 MHz, DMSO-d₆) δ 11.88 (br, 1H), 9.04 (br, 1H), 7.97 (br, 1H), 7.74 (m, 1H), 7.55 (m, 1H), 7.43 (m, 1H), 7.24 (m, 1H), 5.62 (br, 1H), 5.02 (br, 1H), 3.72 (m, 2H), 2.42 (m, 1H), 2.08-1.75 (m, 4H), 0.90 (m, 2H), 0.62 (m, 2H); ESI-MS: calcd for (C₂₁H₂₁F₃N₆) 414, found 415 (MH⁺).

Example 37

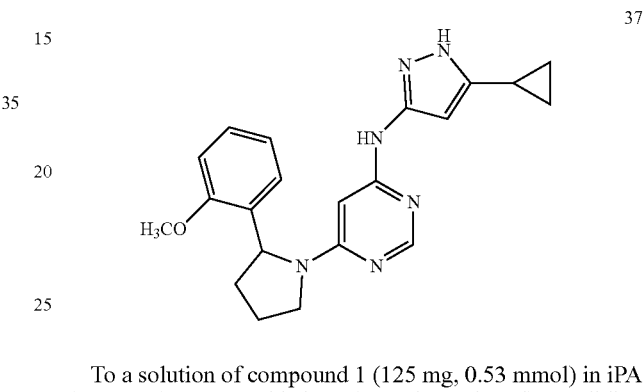

37

To a solution of compound 1 (125 mg, 0.53 mmol) in iPA (2.5 mL) was added 2-(2-methoxyphenyl)pyrrolidine (103.41 mg, 0.58 mmol), and DIPEA (0.14 mL, 0.80 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 37 as beige solid (153 mg, 77%). ¹H NMR (400 MHz, DMSO-d₆) δ 11.84 (br, 1H), 8.98 (br, 1H), 7.99 (br, 1H), 7.20 (m, 1H), 7.02 (m, 1H), 6.81 (m, 2H), 5.69 (br, 1H), 5.02 (br, 1H), 3.86 (s, 3H), 3.72 (m, 2H), 2.40 (m, 1H), 2.08-1.75 (m, 4H), 0.89 (m, 2H), 0.61 (m, 2H); ESI-MS: calcd for (C₂₁H₂₄N₆O) 376, found 377 (MH⁺).

Example 38

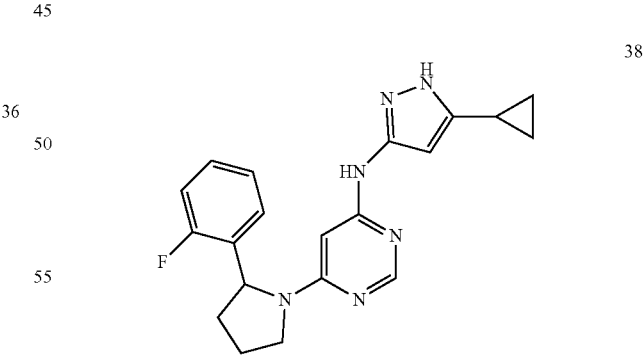

38

To a solution of compound 1 (150 mg, 0.64 mmol) in iPA (2.5 mL) was added 2-(2-fluorophenyl)pyrrolidine (115.67 mg, 0.70 mmol), and DIPEA (0.17 mL, 0.95 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 38 as beige solid (161 mg, 69%). ¹H NMR (400 MHz, DMSO-d₆) δ 11.88 (br, 1H), 9.05 (br, 1H), 7.99 (br, 1H), 7.27 (m, 1H), 7.21 (m, 1H), 7.09 (m, 1H), 7.00 (m, 1H), 5.72 (br, 1H), 5.32 (br, 1H), 3.72 (m, 2H), 2.35 (m, 1H), 2.08-1.75 (m, 4H), 0.90 (m, 2H), 0.63 (m, 2H); ESI-MS: calcd for ($C_{20}H_{21}FN_6$) 364, found 365 (MH⁺).

Example 39

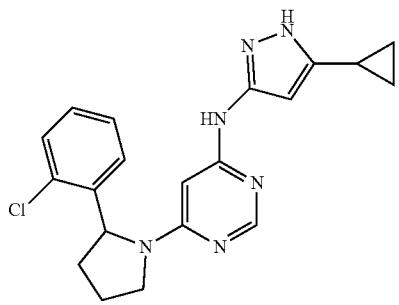

39

To a solution of compound 1 (125 mg, 0.53 mmol) in iPA (2.5 mL) was added 2-(2-chlorophenyl)pyrrolidine (105.99 mg, 0.58 mmol), and DIPEA (0.14 mL, 0.80 mmol) at room temperature and the mixture was stirred at 120° C. for overnight. TLC was taken and the reaction was complete. The crude reaction mixture was concentrated and the residue was subjected to flash column chromatography on silica gel using 0-5% MeOH in DCM (v/v) as eluent to obtain compound 39 as beige solid (117 mg, 58%). ¹H NMR (400 MHz, DMSO-d₆) δ 11.88 (br, 1H), 9.06 (br, 1H), 7.98 (br, 1H), 7.46 (m, 1H), 7.25 (m, 2H), 7.01 (m, 1H), 5.71 (br, 1H), 5.02 (br, 1H), 3.72 (m, 2H), 2.40 (m, 1H), 2.08-1.75 (m, 4H), 0.90 (m, 2H), 0.63 (m, 2H); ESI-MS: calcd for ($C_{20}H_{21}ClN_6$) 380, found 381 (MH⁺).

Example 40

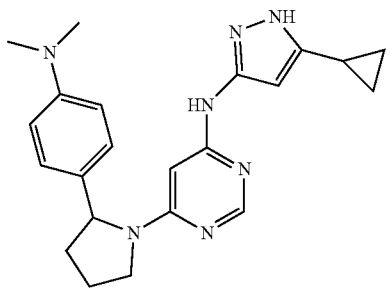

40

The solution of compound 1 (100 mg, 0.42 mmol), dimethyl-(4-pyrrolidine-2yl-phenyl)amine (81 mg, 0.42 mmol) and DIPEA (0.11 ml, 0.63 mmol) DMSO (2.5 mL) was heated at 170° C. for h with a Biotage microwave initiator, then stirred at 150° C. for 24 h with oil bath. TLC was used to monitor the reaction. The reaction mixture was added to half-saturated ammonium chloride in water (80 mL) and stirred for 30 min. The solids were collected by filtration, washed by water. The crude product was purified by column chromatography (0-10% MeOH in DCM) to give compound 40 as yellow solids. (14 mg, 8.5% yield). ¹H NMR (400 MHz, DMSO-d₆) δ 11.83 (s, 1H), 8.92 (s, 1H), 8.00 (s, 1H), 6.96 (d, J=8.4 Hz, 2H), 6.65 (d, J=8.8 Hz, 2H), 6.20 (b, 1H), 5.65 (s, 1H), 5.00 (br, 1H), 3.80-3.40 (br, 2H), 2.84 (s, 6H), 2.33 (m, 1H), 2.00-1.70 (m, 4H), 0.89 (m, 2H), 0.62 (m, 2H); ESI-MS: calcd for ($C_{22}H_{27}N_7$) 389, found 390 (MH⁺).

Example 41

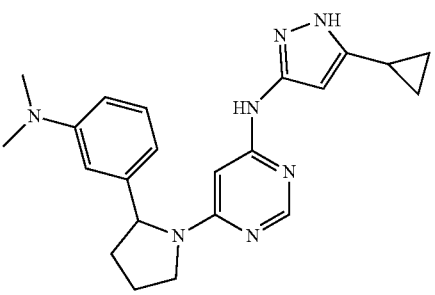

41

Method 1:

The solution of compound 1 (100 mg, 0.42 mmol), N,N-dimethyl-3-(pyrrolidin-2-yl)aniline (81 mg, 0.42 mmol) and DIPEA (0.11 ml, 0.63 mmol) DMSO (2.5 mL) was heated at 150° C. for 24 h with oil bath. TLC was used to monitor the reaction (complicated). The reaction mixture was added to half-saturated ammonium chloride in water (80 mL) and stirred for 30 min. The solids were collected by filtration, washed by water. The crude product was purified by column chromatography (0-10% MeOH in DCM) to give compound 41 as yellow solids. (28 mg, 17% yield). ¹H NMR (400 MHz, DMSO-d₆) δ 11.83 (s, 1H), 8.95 (s, 1H), 8.00 (s, 1H), 7.07 (br, 1H), 6.60-6.30 (m, 3H), 5.75 (br, 1H), 5.20-4.80 (br, 2H), 3.80-3.40 (br, 2H), 2.85 (s, 6H), 2.33 (m, 1H), 2.00-1.70 (m, 4H), 0.89 (m, 2H), 0.62 (m, 2H); ESI-MS: calcd for ($C_{22}H_{27}N_7$) 389, found 390 (MH⁺).

Method 2:

The solution of compound 1 (150 mg, 0.64 mmol), N,N-dimethyl-3-(pyrrolidin-2-yl)aniline (121 mg, 0.64 mmol) and KF (111 mg, 0.64 mmol) DMSO (3.5 mL) was heated at 180° C. with Biotage microwave initiator for 1 h. The reaction mixture was added to half-saturated ammonium chloride in water (80 mL) and stirred for 30 min. The solids were collected by filtration, washed by water. The crude product was purified by column chromatography (0-10% MeOH in DCM) to give compound 41 as yellow solids. (91 mg, 36% yield). ¹H NMR (400 MHz, DMSO-d₆) δ 11.84 (s, 1H), 8.95 (s, 1H), 8.00 (s, 1H), 7.07 (t, J=8.0 Hz, 1H), 6.55 (dd, J=2.4 Hz, J=8.4 Hz, 1H), 6.49 (s, 1H), 6.39 (d, J=7.6 Hz, 1H), 5.70 (br, 1H), 5.20-4.80 (br, 2H), 3.80-3.40 (br, 2H), 2.85 (s, 6H), 2.33 (m, 1H), 2.00-1.70 (m, 4H), 0.89 (m, 2H), 0.62 (m, 2H); ESI-MS: calcd for ($C_{22}H_{27}N_7$) 389, found 390 (MH⁺).

Example 42

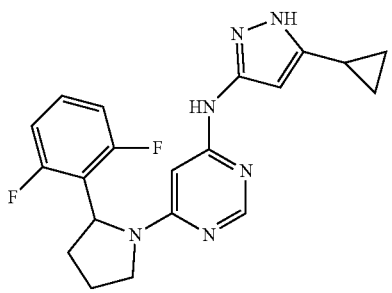

To a solution of 6-chloro-N-(5-cyclopropyl-1H-pyrazol-3-yl)pyrimidin-4-amine compound 1 (150 mg, 0.64 mmol) in DMSO (2.5 mL) was added 2-(2,6-difluorophenyl)pyrrolidine (128.26 mg, 0.70 mmol), and DIPEA (0.17 mL, 0.95 mmol) at room temperature and the mixture was stirred at 120° C. for overnight. After cooling down to rt, the reaction mixture was slowly added to stirring water (~25 mL). Precipitation of solid was observed. Saturated NH$_4$Cl (~25 mL) and saturated NaCl (~25 mL) solution were added and the mixture was stirred for another 30 mins. The solid was then filtered off and dried. The resulting crude solid was purified by flash column chromatography on silica gel using 0-10% MeOH in DCM (v/v) as eluent to obtain compound 42 as beige solid (145 mg, 60%). $^1$H NMR (400 MHz, DMSO-d$_6$) δ 11.86 (br, 1H), 8.99 (br, 1H), 7.93 (br, 1H), 7.28 (m, 1H), 7.00 (m, 2H), 6.29 (br, 1H), 5.70 (br, 1H), 5.31 (br, 1H), 3.49 (m, 2H), 2.45 (m, 1H), 2.05-1.80 (m, 4H), 0.90 (m, 2H), 0.63 (m, 2H); ESI-MS: calcd for (C$_{20}$H$_{20}$F$_2$N$_6$) 382, found 383 (MH$^+$).

Example 43

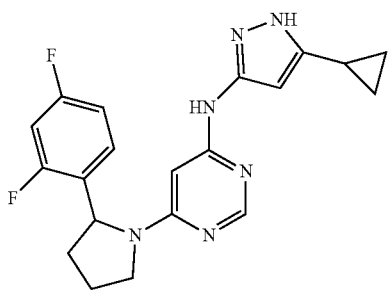

The solution of compound 1 (150 mg, 0.64 mmol), 2-(2,4-difluorophenyl)pyrrolidine (134 mg, 0.73 mmol) and KF (185 mg, 3.18 mmol) DMSO (5 mL) was heated at 170° C. with Biotage microwave initiator for 135 min. The reaction mixture was added to half-saturated ammonium chloride in water (80 mL) and stirred for 30 min. The solids were collected by filtration, washed by water. The crude product was purified by column chromatography (30-70% EtOAc in hexanes) to give compound 43 as yellow solids (38 mg, 16% yield). $^1$H NMR (400 MHz, DMSO-d$_6$) δ 11.87 (s, 1H), 9.05 (s, 1H), 7.99 (s, 1H), 7.22 (m, 1H), 7.20-6.80 (m, 2H), 6.00-5.74 (br, 1H), 5.40-5.20 (br, 1H), 3.90-3.40 (m, 2H), 2.32 (m, 1H), 2.10-1.70 (m, 4H), 0.88 (m, 2H), 0.63 (m, 2H); ESI-MS: calcd for (C$_{20}$H$_{20}$F$_2$N$_6$) 382, found 383 (MH$^+$).

Example 44

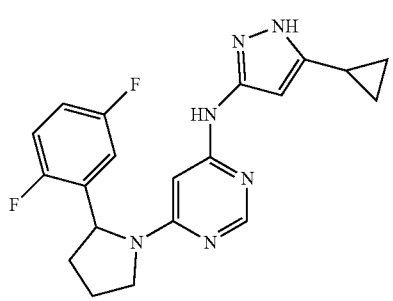

Method 1:

The solution of compound 1 (100 mg, 0.42 mmol), 2-(2,5-Difluorophenyl)pyrrolidine (78 mg, 0.42 mmol) and DIPEA (0.11 ml, 0.63 mmol) DMSO (2.5 mL) was heated at 150° C. for 24 h with oil bath. TLC was used to monitor the reaction (complicated). The reaction mixture was added to half-saturated ammonium chloride in water (80 mL) and stirred for 30 min. The solids were collected by filtration, washed by water. The crude product was purified by column chromatography (0-10% MeOH in DCM) to give compound 44 as yellow solids. (23 mg, 14% yield). $^1$H NMR (400 MHz, DMSO-d$_6$) δ 11.88 (s, 1H), 9.09 (s, 1H), 7.99 (s, 1H), 7.25 (m, 1H), 7.09 (m, 1H), 6.79 (m, 1H), 5.75 (br, 1H), 5.20-4.80 (br, 2H), 3.80-3.40 (br, 2H), 2.33 (m, 1H), 2.00-1.70 (m, 4H), 0.88 (m, 2H), 0.64 (m, 2H); ESI-MS: calcd for (C$_{20}$H$_{20}$F$_2$N$_6$) 382, found 383 (MH$^+$).

Method 2:

The solution of compound 1 (150 mg, 0.64 mmol), 2-(2,5-Difluorophenyl)pyrrolidine (117 mg, 0.64 mmol) and KF (185 mg, 3.18 mmol) DMSO (3.5 mL) was heated at 180° C. with Biotage microwave initiator for 1 h. The reaction mixture was added to half-saturated ammonium chloride in water (80 mL) and stirred for 30 min. The solids were collected by filtration, washed by water. The crude product was purified by column chromatography (0-10% MeOH in DCM) to give compound 44 as yellow solids (120 mg, 49% yield). $^1$H NMR (400 MHz, DMSO-d$_6$) δ 11.83 (s, 1H), 8.95 (s, 1H), 8.00 (s, 1H), 7.07 (br, 1H), 6.60-6.30 (m, 3H), 5.75 (br, 1H), 5.20-4.80 (br, 2H), 3.80-3.40 (br, 2H), 2.85 (s, 6H), 2.33 (m, 1H), 2.00-1.70 (m, 4H), 0.89 (m, 2H), 0.62 (m, 2H); ESI-MS: calcd for (C$_{22}$H$_{27}$N$_7$) 389, found 390 (MH$^+$).

Example 45

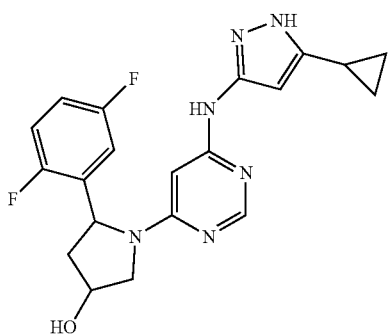

The solution of compound 1 (100 mg, 0.42 mmol), 5-(2,5-difluorophenyl)pyrrolidin-3-ol hydrochloride (101 mg, 0.43 mmol) and KF (74 mg, 1.27 mmol) DMSO (3.5 mL) was heated at 180° C. with Biotage microwave initiator for 1 h. The reaction mixture was added to half-saturated ammonium chloride in water (80 mL) and stirred for 30 min. The solids were collected by filtration, washed by water. The crude product was purified by column chromatography (0-10% MeOH in DCM) to give compound 45 as yellow solids (30 mg, 18% yield). $^1$H NMR (400 MHz, DMSO-$d_6$) δ 11.87 (s, 1H), 9.09 (s, 1H), 8.00 (s, 1H), 7.20 (m, 1H), 7.04 (m, 1H), 6.88 (m, 1H), 6.40 (br, 1H), 5.75 (s, 1H), 5.12 (m, 2H), 4.44 (m, 1H), 3.80-3.40 (m, 2H), 2.33 (m, 1H), 2.00-1.70 (m, 2H), 0.89 (m, 2H), 0.64 (m, 2H); ESI-MS: calcd for ($C_{20}H_{20}F_2N_6O$) 398, found 399 (MH$^+$).

Example 46

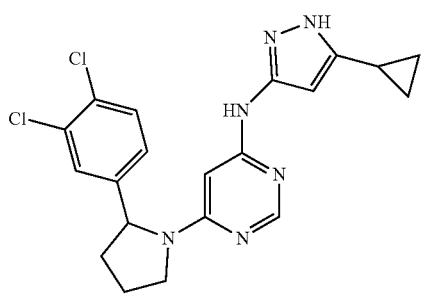

The solution of compound 1 (100 mg, 0.42 mmol), 2-(3,4-dichlorophenyl)pyrrolidine (92 mg, 0.42 mmol) and DIPEA (0.11 ml, 0.63 mmol) DMSO (2.5 mL) was stirred at 150° C. for 24 h with oil bath. TLC was used to monitor the reaction (complicated). The reaction mixture was added to half-saturated ammonium chloride in water (80 mL) and stirred for 30 min. The solids were collected by filtration, washed by water. The crude product was purified by column chromatography (0-10% MeOH in DCM) to give compound 46 as yellow solids. (12 mg, 6.8% yield). $^1$H NMR (400 MHz, DMSO-$d_6$) δ 11.88 (s, 1H), 9.06 (s, 1H), 7.99 (s, 1H), 7.54 (d, J=8.4 Hz, 1H), 7.41 (s, 1H), 7.15 (d, J=8.0 Hz, 1H), 6.20 (b, 1H), 5.75 (s, 1H), 5.00 (br, 1H), 3.80-3.40 (br, 2H), 2.33 (m, 1H), 2.00-1.70 (m, 4H), 0.88 (m, 2H), 0.62 (m, 2H); ESI-MS: calcd for ($C_{20}H_{20}Cl_2N_6$) 414, found 415 (MH$^+$).

Example 47

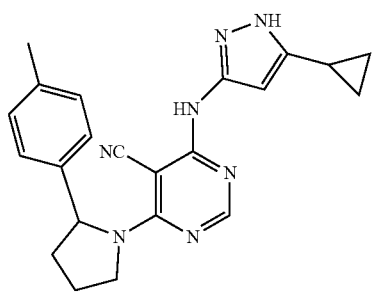

The solution of compound 2 (150 mg, 0.58 mmol), 2-(4-methylphenyl)pyrrolidine (93 mg, 0.58 mmol) and DIPEA (0.15 ml, 0.86 mmol) DMSO (3.5 mL) was stirred at 105° C. for 2 hours. TLC was checked and the starting material was consumed. The reaction mixture was added to half-saturated ammonium chloride in water (80 mL) and stirred for 30 min, then cooled with ice bath. The solids were collected by filtration, washed by water. The crude product was purified by column chromatography (0-10% MeOH in DCM) to give compound 47 as yellow solids. (131 mg, 59% yield). $^1$H NMR (400 MHz, DMSO-$d_6$) δ 12.14 (br, 1H), 8.61 (br, 1H), 8.05 (s, 1H), 7.09 (d, J=8.0 Hz, 2H), 7.02 (d, J=8.0 Hz, 2H), 6.10 (s, 1H), 5.53 (br, 1H), 4.13 (br, 1H), 3.84 (br, 1H), 2.33 (m, 1H), 2.25 (s, 3H), 2.00-1.70 (m, 4H), 0.89 (m, 2H), 0.65 (m, 2H); ESI-MS: calcd for ($C_{22}H_{23}N_7$) 385, found 386 (MH$^+$).

Example 48

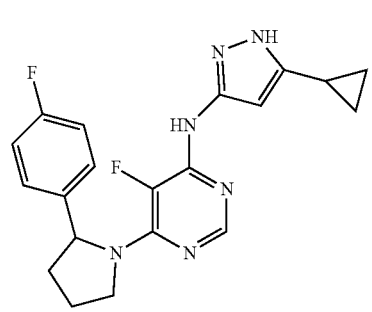

The solution of compound 3 (150 mg, 0.59 mmol), 2-(4-Fluorophenyl)pyrrolidine (117 mg, 0.71 mmol) and KF (103 mg, 1.77 mmol) DMSO (3.5 mL) was heated at 180° C. with Biotage microwave initiator for 30 min. The reaction mixture was added to half-saturated ammonium chloride in water (80 mL) and stirred for 30 min. The solids were collected by filtration, washed by water. The crude product was purified by column chromatography (0-10% MeOH in DCM) to give compound 48 as yellow solids (131 mg, 58% yield). $^1$H NMR (400 MHz, DMSO-$d_6$) δ 11.90 (s, 1H), 9.00 (s, 1H), 7.83 (s, 1H), 7.21 (m, 2H), 7.10 (m, 2H), 6.06 (br, 1H), 5.34 (m, 1H), 3.97 (m, 1H), 3.70 (m, 1H), 2.32 (m, 1H), 2.00-1.70 (m, 4H), 0.87 (m, 2H), 0.63 (m, 2H); ESI-MS: calcd for ($C_{20}H_{20}F_2N_6$) 382, found 383 (MH$^+$).

Example 49

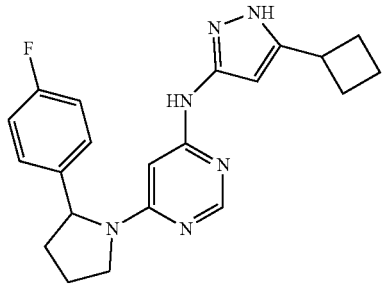

To a solution of 6-chloro-N-(5-cyclobutyl-1H-pyrazol-3-yl)pyrimidin-4-amine compound 4 (150 mg, 0.601 mmol) in DMSO (2.5 mL) was added 2-(4-fluorophenyl)pyrrolidine (119.09 mg, 0.721 mmol), and DIPEA (0.16 mL, 0.90 mmol) at room temperature and the mixture was stirred at 120° C. for overnight. After cooling down to rt, the reaction mixture was slowly added to half-saturated NH$_4$Cl (~50 mL) while stirring. Precipitation of solid was observed. The mixture was continued stirring for 30 mins. The solid was then filtered off and dried. The resulting crude solid was purified by flash column chromatography on silica gel using 0-5% MeOH in DCM (v/v) as eluent to obtain compound 49 as beige solid (49 mg, 22%). $^1$H NMR (400 MHz, DMSO-d$_6$) δ 11.88 (br, 1H), 9.03 (br, 1H), 8.01 (br, 1H), 7.19 (m, 4H), 6.25 (br, 1H), 5.86 (br, 1H), 5.02 (br, 1H), 3.42 (m, 1H), 2.49-1.80 (m, 10H); ESI-MS: calcd for (C$_{21}$H$_{23}$FN$_6$) 378, found 379 (MH$^+$).

Example 50

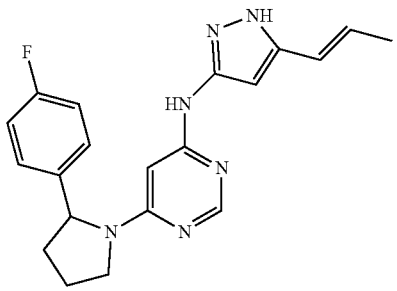

To a solution of (E)-6-chloro-N-(5-(prop-1-en-1-yl)-1H-pyrazol-3-yl)pyrimidin-4-amine compound 5 (150 mg, 0.636 mmol) in DMSO (2.5 mL) was added 2-(4-fluorophenyl)pyrrolidine (126.18 mg, 0.764 mmol), and DIPEA (0.17 mL, 0.95 mmol) at room temperature and the mixture was stirred at 120° C. for overnight. After cooling down to rt, the reaction mixture was slowly added to half-saturated NH$_4$Cl (~50 mL) while stirring. Precipitation of solid was observed. The mixture was continued stirring for 30 mins. The solid was then filtered off and dried. The resulting crude solid was purified by flash column chromatography on silica gel using 0-5% MeOH in DCM (v/v) as eluent to obtain compound 50 as beige solid (42 mg, 18%). $^1$H NMR (400 MHz, DMSO-d$_6$) δ 12.12 (br, 1H), 9.09 (br, 1H), 8.02 (br, 1H), 6.90-7.50 (m, 5H), 6.24 (m, 3H), 5.02 (br, 1H), 3.71 (m, 2H), 2.34 (m, 2H), 2.05-1.80 (m, 5H); ESI-MS: calcd for (C$_{20}$H$_{21}$FN$_6$) 364, found 365 (MH$^+$).

Example 51

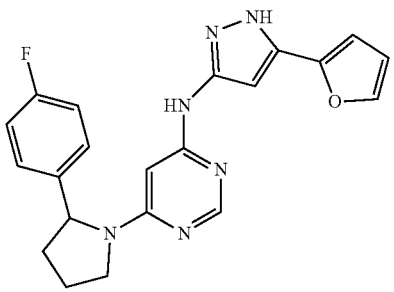

A mixture of 4-chloro-6-(2-(4-fluorophenyl)pyrrolidin-1-yl)pyrimidine compound 6 (200 mg, 0.720 mmol), tert-butyl 3-amino-5-(furan-2-yl)-1H-pyrazole-1-carboxylate compound 7 (197.46 mg, 0.792 mmol), xantphos (4,5-diphenyl-phosphanyl-9,9'-dimethyl-9-H-xanthene, 104.17 mg, 0.180 mmol), K$_2$CO$_3$ (497.63 mg, 3.60 mmol) and palladium(II) acetate (24.25 mg, 0.108 mmol) in 1,4-dioxane (10 ml) was purged with argon for 1 hour. The mixture was heated in an oil bath for overnight at 85° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 51 as brown solids (190 mg, 69% yield). $^1$H NMR (400 MHz, DMSO-d$_6$) δ 12.62 (br, 1H), 9.34 (s, 1H), 8.07 (s, 1H), 7.73 (s, 1H), 7.20 (d, J=5.2 Hz, 2H), 7.13 (d, J=8.8 Hz, 2H), 6.76 (m, 1H), 6.59 (m, 1H), 6.34 (br, 2H), 5.02 (br, 1H), 3.73 (m, 2H), 2.34 (m, 1H), 1.97-1.75 (m, 3H); ESI-MS: calcd for (C$_{21}$H$_{19}$FN$_6$O) 390, found 391 (MH$^+$).

Example 52

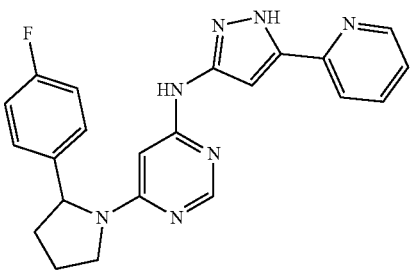

To a solution of 6-chloro-N-(5-(pyridin-2-yl)-1H-pyrazol-3-yl)pyrimidin-4-amine compound 8 (60 mg, 0.22 mmol) in DMSO (2.5 mL) was added 2-(4-fluorophenyl)pyrrolidine (43.62 mg, 0.26 mmol), and DIPEA (0.06 mL, 0.33 mmol) at room temperature and the mixture was stirred at 120° C. for overnight. After cooling down to rt, the reaction mixture was slowly added to stirring water (~25 mL). Precipitation of solid was observed. Saturated NH$_4$Cl (~25 mL) and saturated NaCl (~25 mL) solution were added and the mixture was then stirred for another 30 mins. The solid was then filtered off and dried. The resulting crude solid was then purified by flash column chromatography on silica gel using 0-10% MeOH in DCM (v/v) as eluent to obtain compound 52 as off-white solids (54 mg, 61%). $^1$H NMR (400 MHz, DMSO-d$_6$) δ 12.63 (br, 1H), 9.27 (br, 1H), 8.60 (s, 1H), 8.07 (br, 1H), 7.86 (m, 2H), 7.33 (m, 1H), 7.21 (d, J=8.0 Hz, 2H), 7.11 (d, J=8.4 Hz, 2H), 6.74 (br, 1H), 6.22 (br, 1H), 5.02 (br, 1H), 3.74 (m, 2H), 2.33 (m, 1H), 1.97-1.75 (m, 4H); ESI-MS: calcd for ($C_{22}H_{20}FN_7$) 401, found 402 (MH$^+$).

Example 53

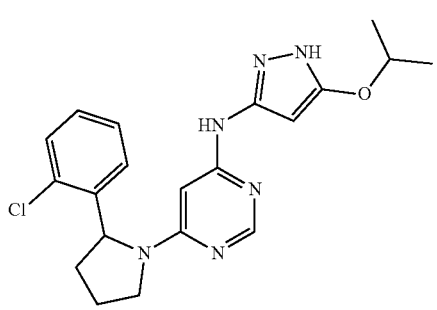

The mixture of compound 9 (95 mg, 0.37 mmol), 2-(2-chlorophenyl)pyrrolidine (78 mg, 0.43 mmol) and KF (66 mg, 1.12 mmol) DMSO (3.5 mL) was heated at 180° C. with Biotage microwave initiator for 90 min. TLC was checked and the starting material was almost consumed. The reaction mixture was added to half-saturated ammonium chloride in water (75 mL) and stirred for 30 min. The solids were collected by filtration, washed by water. The crude product was purified by column chromatography (0-10% MeOH in DCM) to give compound 53 as yellow solids. (47 mg, 31% yield). $^1$H NMR (400 MHz, DMSO-d$_6$) δ 11.68 (br, 1H), 9.47 (s, 1H), 8.04 (br, 1H), 7.50-6.80 (m, 4H), 5.80-5.00 (m, 3H), 4.50 (br, 1H), 3.80-3.40 (br, 2H), 2.40 (m, 1H), 2.00-1.70 (m, 3H), 1.25 (d, J=5.6 Hz, 6H); ESI-MS: calcd for ($C_{20}H_{23}ClN_6O$) 398, found 399 (MH$^+$).

Example 54

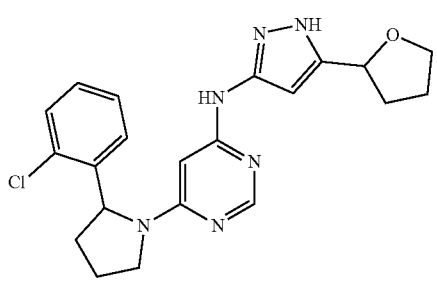

The mixture of compound 10 (100 mg, 0.38 mmol), 2-(2-chlorophenyl)pyrrolidine (78 mg, 0.43 mmol) and KF (66 mg, 1.12 mmol) DMSO (3.5 mL) was heated at 180° C. with Biotage microwave initiator for 90 min. TLC was checked and the starting material was almost consumed. The reaction mixture was added to half-saturated ammonium chloride in water (75 mL) and stirred for 30 min. The solids were collected by filtration, washed by water. The crude product was purified by column chromatography (0-10% MeOH in DCM) to give compound 54 as yellow solids. (61 mg, 39% yield). 1H NMR (400 MHz, DMSO-d6) δ 12.10 (br, 1H), 9.14 (s, 1H), 8.00 (br, 1H), 7.45 (d, J=8.4 Hz, 1H), 7.25 (m, 2H), 7.00 (d, J=9.6 Hz, 1H), 6.4 (br, 1H), 6.0 (br, 1H), 5.35 (br, 1H), 4.80 (br, 1H), 4.00-3.20 (m, 4H), 2.38 (br, 1H), 3.18 (m, 1H), 2.00-1.70 (m, 6H); ESI-MS: calcd for ($C_{21}H_{23}ClN_6O$) 410, found 411 (MH$^+$).

Example 55

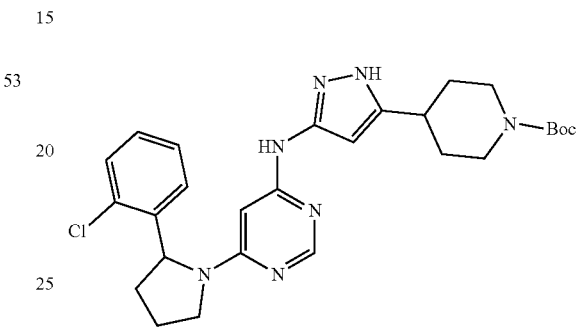

The mixture of compound 11 (230 mg, 0.61 mmol), 2-(2-chlorophenyl)pyrrolidine (127 mg, 0.70 mmol) and KF (106 mg, 1.82 mmol) DMSO (3.5 mL) was heated at 180° C. with Biotage microwave initiator for 90 min. TLC was checked and the starting material was almost consumed. The reaction mixture was added to half-saturated ammonium chloride in water (75 mL) and stirred for 30 min. The solids were collected by filtration, washed by water. The crude product was purified by column chromatography (0-10% MeOH in DCM) to give compound 55 as yellow solids. (29 mg, 9% yield). $^1$H NMR (400 MHz, DMSO-d$_6$) δ 11.94 (br, 1H), 9.07 (s, 1H), 7.99 (br, 1H), 7.45 (d, J=9.2 Hz, 1H), 7.24 (m, 2H), 7.01 (d, J=9.2 Hz, 1H), 6.20-5.60 (br, 2H), 5.40 (br, 1H), 4.20-3.40 (m, 6H), 2.73 (m, 3H), 2.39 (m, 1H), 2.00-1.60 (m, 5H), 1.41 (s, 9H); ESI-MS: calcd for ($C_{27}H_{34}ClN_7O_2$) 523, found 524 (MH$^+$).

Example 56

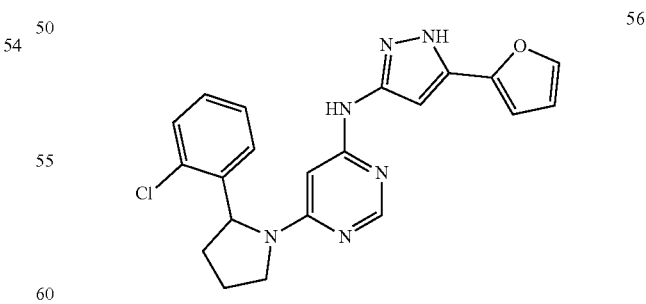

The mixture of compound 12 (150 mg, 0.57 mmol), 2-(2-chlorophenyl)pyrrolidine (115 mg, 0.63 mmol) and KF (99 mg, 1.71 mmol) DMSO (3.5 mL) was heated at 180° C. with Biotage microwave initiator for 90 min. TLC was checked and the starting material was almost consumed. The reaction mixture was added to half-saturated ammonium chloride in water (75 mL) and stirred for 30 min. The solids were collected by filtration, washed by water. The crude product was purified by column chromatography (0-10% MeOH in DCM) to give compound 56 as yellow solids. (71 mg, 31% yield). $^1$H NMR (400 MHz, DMSO-$d_6$) δ 12.68 (s, 1H), 9.32 (s, 1H), 8.04 (s, 1H), 7.50-6.40 (m, 8H), 5.30 (br, 1H), 3.80-3.40 (br, 2H), 2.39 (m, 1H), 2.00-1.70 (m, 3H); ESI-MS: calcd for ($C_{21}H_{19}ClN_6O$) 406, found 407 (MH$^+$).

was concentrated. The crude product was then subjected to column chromatography (silica gel, 0-10% MeOH in DCM) followed by trituration with MeOH to obtain compound 58 as white solids (17 mg, 5% yield). $^1$H NMR (400 MHz, DMSO-$d_6$) δ 11.96 (br, 1H), 8.35 (br, 1H), 8.20 (s, 1H), 8.13 (s, 1H), 7.21 (m, 4H), 4.90 (br, 1H), 3.79 (m, 2H), 2.33 (m, 1H), 1.97-1.75 (m, 3H); ESI-MS: calcd for ($C_{18}H_{15}FN_6S$) 366, found 367 (MH$^+$).

Example 57

Example 59

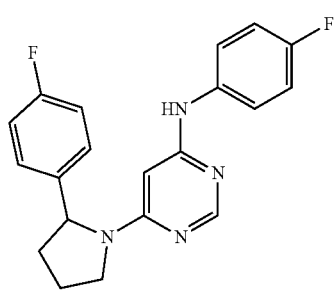

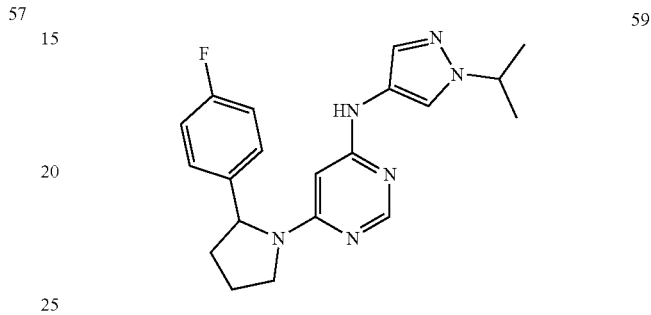

The solution of compound 13 (150 mg, 0.67 mmol), 2-(4-Fluorophenyl)pyrrolidine (115 mg, 0.70 mmol) and KF (116 mg, 2.00 mmol) DMSO (3.5 mL) was heated at 180° C. with Biotage microwave initiator for 80 min. The reaction mixture was added to half-saturated ammonium chloride in water (80 mL) and stirred for 30 min. The solids were collected by filtration, washed by water. The crude product was purified by column chromatography (0-10% MeOH in DCM) to give compound 57 as yellow solids (90 mg, 38% yield). $^1$H NMR (400 MHz, DMSO-$d_6$) δ 8.95 (s, 1H), 8.08 (s, 1H), 7.43 (br, 2H), 7.20-7.00 (m, 6H), 5.49 (br, 1H), 5.00 (br, 1H), 3.80-3.40 (m, 2H), 2.33 (m, 1H), 2.00-1.70 (m, 3H); ESI-MS: calcd for ($C_{20}H_{18}F_2N_4$) 352, found 353 (MH$^+$).

A mixture of 4-chloro-6-(2-(4-fluorophenyl)pyrrolidin-1-yl)pyrimidine compound 6 (200 mg, 0.720 mmol), 1-isopropyl-1H-pyrazol-4-amine (112.68 mg, 0.900 mmol), xantphos (4,5-diphenylphosphanyl-9,9'-dimethyl-9-H-xanthene, 104.17 mg, 0.180 mmol), $K_2CO_3$ (497.63 mg, 3.60 mmol) and palladium(II) acetate (24.25 mg, 0.108 mmol) in 1,4-dioxane (10 ml) was purged with argon for 1 hour. The mixture was heated in an oil bath for overnight at 90° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain compound 59 as orange solids (133 mg, 50% yield). $^1$H NMR (400 MHz, DMSO-$d_6$) δ 8.62 (br, 1H), 8.04 (s, 1H), 7.68 (br, 1H), 7.26 (s, 1H), 7.14 (m, 4H), 5.32 (br, 1H), 4.98 (br, 1H), 4.39 (m, 1H), 3.73 (m, 2H), 2.34 (m, 1H), 1.91 (m, 3H), 1.37 (d, J=6.8 Hz, 6H); ESI-MS: calcd for ($C_{20}H_{23}FN_6$) 366, found 367 (MH$^+$).

Example 58

Example 60

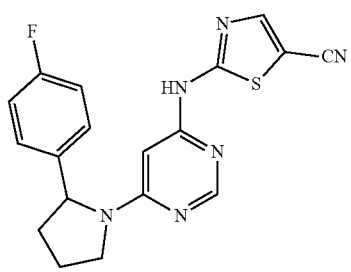 [SMILES: N#Cc1cnc(Nc2cc(N3CCCC3c3ccc(F)cc3)ncn2)s1]

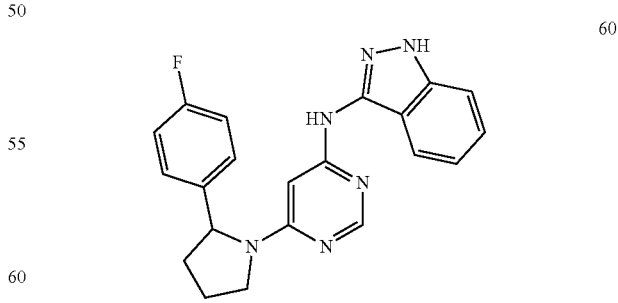

A mixture of 4-chloro-6-(2-(4-fluorophenyl)pyrrolidin-1-yl)pyrimidine compound 6 (200 mg, 0.720 mmol), 2-aminothiazole-5-carbonitrile (135.19 mg, 1.08 mmol), xantphos (4,5-diphenylphosphanyl-9,9'-dimethyl-9-H-xanthene, 104.17 mg, 0.180 mmol), $K_3PO_4$ (229.29 mg, 1.08 mmol) and palladium(II) acetate (24.25 mg, 0.108 mmol) in 1,4-dioxane (10 ml) was purged with argon for 1 hour. The mixture was heated in an oil bath at 85° C. for 5 h. TLC was checked and the starting material was consumed. After cooling to room temperature, the reaction mixture was passed through a pad of celite using 10% MeOH/DCM and To a solution of N-(6-chloropyrimidin-4-yl)-1H-indazol-3-amine compound 14 (150 mg, 0.610 mmol) in DMSO (2.5 mL) was added 2-(4-fluorophenyl)pyrrolidine (121.05 mg, 0.733 mmol), and DIPEA (0.16 mL, 0.92 mmol) at room temperature and the mixture was stirred at 120° C. for overnight. After cooling down to rt, the reaction mixture was slowly added to half-saturated NH₄Cl (~50 mL) while stirring. Precipitation of solid was observed. The mixture was continued stirring for 30 mins. Filtration of the solid followed by trituration with DCM provided compound 60 as beige solid (105 mg, 46%). ¹H NMR (400 MHz, DMSO-d₆) δ 12.33 (br, 1H), 9.66 (br, 1H), 8.08 (m, 2H), 7.41 (m, 1H), 7.38 (m, 1H), 7.34 (m, 2H), 7.32 (m, 2H), 7.30 (m, 1H), 6.85 (br, 1H), 5.31 (br, 1H), 3.75 (m, 1H), 2.45 (m, 1H), 1.85 (m, 3H); ESI-MS: calcd for (C₂₁H₁₉FN₆) 374, found 375 (MH⁺).

Example 61

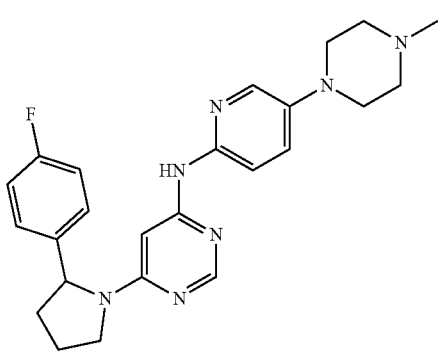

61

A mixture of 4-chloro-6-(2-(4-fluorophenyl)pyrrolidin-1-yl)pyrimidine compound 6 (200 mg, 0.720 mmol), 5-(4-methylpiperazin-1-yl)pyridin-2-amine compound 15 (152.30 mg, 0.792 mmol), xantphos (4,5-diphenylphospha-nyl-9,9'-dimethyl-9-H-xanthene, 104.17 mg, 0.180 mmol), K₂CO₃ (497.63 mg, 3.60 mmol) and palladium(II) acetate (24.25 mg, 0.108 mmol) in 1,4-dioxane (10 ml) was purged with argon for 1 hour. The mixture was heated in an oil bath for overnight at 105° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 61 as brown solids (244 mg, 78% yield). ¹H NMR (400 MHz, DMSO-d₆) δδ 9.28 (s, 1H), 8.07 (s, 1H), 7.82 (s, 1H), 7.34 (m, 2H), 7.23 (m, 2H), 7.14 (m, 2H), 6.72 (br, 1H), 5.02 (br, 1H), 3.74 (m, 2H), 3.17 (m, 4H), 2.47-2.44 (m, 4H), 2.38 (s, 3H), 2.00-1.75 (m, 4H); ESI-MS: calcd for (C₂₄H₂₈FN₇) 433, found 434 (MH⁺).

Example 62

The solution of compound 1 (150 mg, 0.64 mmol), 2-(4-fluorophenyl)azetidine (97 mg, 064 mmol) and KF (110 mg, 1.91 mmol) DMSO (3.5 mL) was heated at 180° C. with Biotage microwave initiator for 1 h. The reaction mixture was added to half-saturated ammonium chloride in water (80 mL) and stirred for 30 min. The solids were collected by filtration, washed by water. The crude product was purified by column chromatography (0-10% MeOH in DCM) to give compound 62 as yellow solids (32 mg, 14% yield). ¹H NMR (400 MHz, DMSO-d₆) δ 11.87 (s, 1H), 9.11 (s, 1H), 804 (s, 1H), 7.46 (m, 2H), 7.20 (m, 2H), 6.16 (br, 1H), 5.71 (s, 1H), 5.18 (t, J=7.2 Hz, 1H), 4.05 (m, 1H), 3.91 (m, 1H), 2.73 (m, 1H), 2.19 (m, 1H), 1.81 (m, 1H), 0.89 (m, 2H), 0.61 (m, 2H); ESI-MS: calcd for C₁₉H₁₉FN₆ 350, found 351 (MH⁺).

Example 63

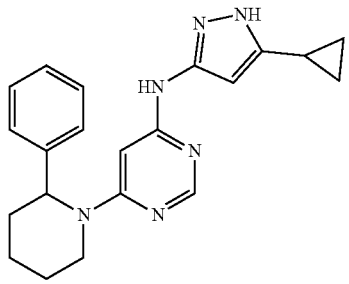

63

A mixture of 4-chloro-6-(2-phenylpiperidin-1-yl)pyrimidine compound 16 (200 mg, 0.731 mmol), tert-butyl 3-amino-5-cyclopropyl-1H-pyrazole-1-carboxylate compound 17 (179.43 mg, 0.804 mmol), xantphos (4,5-diphenylphosphanyl-9,9'-dimethyl-9-H-xanthene, 105.68 mg, 0.183 mmol), K₂CO₃ (504.83 mg, 3.65 mmol) and palladium(II) acetate (24.60 mg, 0.110 mmol) in 1,4-dioxane (10 ml) was purged with argon for 1 hour. The mixture was heated in an oil bath for overnight at 105° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 63 as yellow solids (46 mg, 17% yield). ¹H NMR (400 MHz, DMSO-d₆) δ 11.88 (br, 1H), 9.11 (s, 1H), 8.08 (s, 1H), 7.33 (m, 2H), 7.21 (m, 3H), 6.70 (br, 1H), 5.76 (s, 1H), 5.69 (br, 1H), 4.19 (m, 1H), 2.94 (m, 1H), 2.35 (m, 1H), 1.82 (m, 2H), 1.64-1.37 (m, 5H), 0.89 (m, 2H), 0.63 (m, 2H); ESI-MS: calcd for (C₂₁H₂₄N₆) 360, found 361 (MH⁺).

Example 64

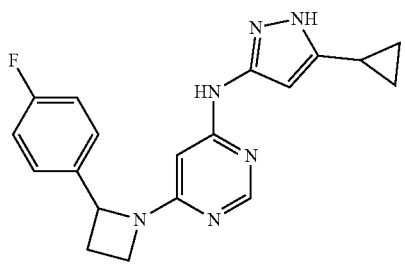

62

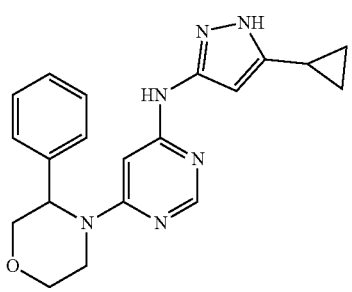

64

A mixture of 4-(6-chloropyrimidin-4-yl)-3-phenylmorpholine compound 18 (150 mg, 0.544 mmol), tert-butyl 3-amino-5-cyclopropyl-1H-pyrazole-1-carboxylate compound 17 (133.61 mg, 0.598 mmol), xantphos (4,5-diphenylphosphanyl-9,9'-dimethyl-9-H-xanthene, 78.69 mg, 0.136 mmol), $K_2CO_3$ (375.92 mg, 2.72 mmol) and palladium(II) acetate (18.32 mg, 0.082 mmol) in 1,4-dioxane (10 ml) was purged with argon for 1 hour. The mixture was heated in an oil bath for overnight at 105° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 64 as brown solids (78 mg, 40% yield). $^1$H NMR (400 MHz, DMSO-d$_6$) δ 11.86 (br, 1H), 9.19 (s, 1H), 8.11 (s, 1H), 7.35-7.20 (m, 5H), 6.64 (br, 1H), 5.77 (s, 1H), 5.38 (s, 1H), 4.35 (m, 2H), 3.91 (m, 2H), 3.88 (m, 1H), 3.58 (m, 1H), 3.25 (m, 1H), 1.82 (m, 1H), 0.89 (m, 2H), 0.64 (m, 2H); ESI-MS: calcd for ($C_{20}H_{22}N_6O$) 362.2, found 363.3 (MH$^+$).

Example 65

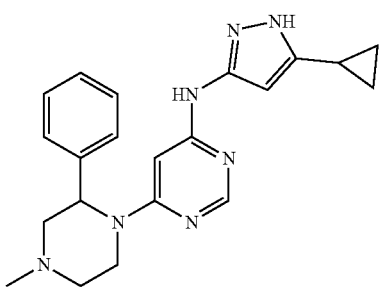

The solution of compound 1 (150 mg, 0.64 mmol), 1-Methyl-3-phenylpiperazine (112 mg, 0.64 mmol), NaI (190 mg, 1.27 mmol) and DIPEA (0.22 ml, 1.27 mmol) DMSO (3.5 mL) was stirred at 135° C. for 48 h with oil bath. TLC was used to monitor the reaction. After cooled to room temperature, the reaction mixture was added to half-saturated ammonium chloride in water (80 mL) and stirred for 30 min. The solids were collected by filtration, washed by water. The crude product was purified by column chromatography (0-10% MeOH in DCM) to give compound 65 as yellow solids. (51 mg, 21% yield). $^1$H NMR (400 MHz, DMSO-d$_6$) δ 11.91 (s, 1H), 9.12 (s, 1H), 8.08 (s, 1H), 7.30-7.00 (m, 5H), 6.70 (b, 1H), 5.75 (b, 1H), 5.54 (br, 1H), 4.02 (br, 1H), 3.32 (m, 1H), 3.12 (m, 1H), 2.80 (m, 1H), 2.32 (m, 1H), 2.16 (s, 3H), 1.98 (m, 1H), 1.82 (m, 1H), 0.88 (m, 2H), 0.62 (m, 2H); ESI-MS: calcd for ($C_{21}H_{25}N_7$) 375, found 376 (MH$^+$).

Example 66

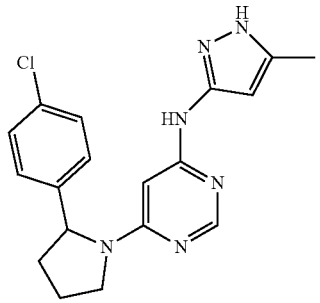

To a solution of 6-chloro-N-(5-methyl-1H-pyrazol-3-yl)pyrimidin-4-amine compound 19 (100 mg, 0.48 mmol) in DMSO (2.5 mL) was added 2-(4-chlorophenyl)pyrrolidine (95.32 mg, 0.52 mmol), and DIPEA (0.12 mL, 0.72 mmol) at room temperature and the mixture was stirred at 120° C. for overnight. After cooling down to rt, the reaction mixture was slowly added to half saturated NH4Cl solution in water (~50 mL). Precipitation of solid was observed. The solid was then filtered off and dried. The resulting crude solid was then purified by flash column chromatography on silica gel using 0-10% MeOH in DCM (v/v) as eluent to obtain compound 66 as white solids (92 mg, 54%). $^1$H NMR (400 MHz, DMSO-d$_6$) δ 11.80 (br, 1H), 9.01 (br, 1H), 7.99 (br, 1H), 7.35 (d, J=8.0 Hz, 2H), 7.19 (d, J=8.4 Hz, 2H), 6.27 (br, 1H), 5.76 (br, 1H), 5.02 (br, 1H), 3.70 (m, 2H), 2.34 (m, 1H), 2.15 (s, 3H), 21.95-1.75 (m, 3H); ESI-MS: calcd for ($C_{18}H_{19}ClN_6$) 354, found 355 (MH$^+$).

Example 67

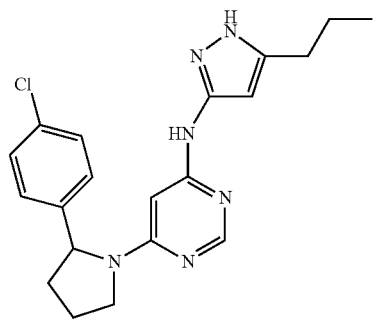

To a solution of 6-chloro-N-(5-propyl-1H-pyrazol-3-yl)pyrimidin-4-amine compound 20 (100 mg, 0.42 mmol) in DMSO (2.5 mL) was added 2-(4-chlorophenyl)pyrrolidine (84.07 mg, 0.46 mmol), and DIPEA (0.11 mL, 0.63 mmol) at room temperature and the mixture was stirred at 120° C. for overnight. After cooling down to rt, the reaction mixture was slowly added to half saturated NH4Cl solution in water (~50 mL). Precipitation of solid was observed. The solid was then filtered off and dried. The resulting crude solid was then purified by flash column chromatography on silica gel using 0-10% MeOH in DCM (v/v) as eluent to obtain compound 67 as beige solids (84 mg, 52%). $^1$H NMR (400 MHz, DMSO-d$_6$) δ 11.83 (br, 1H), 9.02 (br, 1H), 7.99 (br, 1H), 7.35 (d, J=8.0 Hz, 2H), 7.19 (d, J=8.4 Hz, 2H), 6.29 (br, 1H), 5.78 (br, 1H), 5.02 (br, 1H), 3.71 (m, 2H), 2.48 (m, 2H), 2.34 (m, 1H), 1.95-1.75 (m, 3H), 1.57 (m, 2H), 0.91 (t, J=7.2 Hz, 3H); ESI-MS: calcd for (C$_{20}$H$_{23}$ClN$_6$) 382, found 383 (MH$^+$).

Example 68

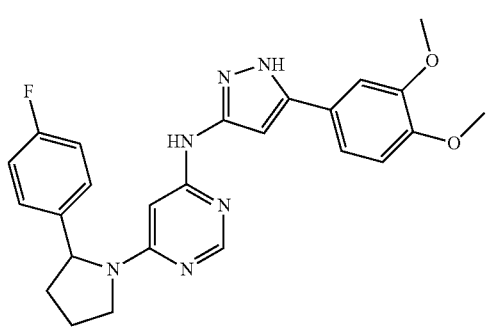

68

A mixture of 4-chloro-6-(2-(4-fluorophenyl)pyrrolidin-1-yl)pyrimidine compound 6 (200 mg, 0.720 mmol), tert-butyl 3-amino-5-(3,4-dimethoxyphenyl)-1H-pyrazole-1-carboxylate compound 21 (287.48 mg, 0.900 mmol), xantphos (4,5-diphenylphosphanyl-9,9'-dimethyl-9-H-xanthene, 104.17 mg, 0.180 mmol), K$_2$CO$_3$ (497.63 mg, 3.60 mmol) and palladium(II) acetate (24.25 mg, 0.108 mmol) in 1,4-dioxane (10 ml) was purged with argon for 1 hour. The mixture was heated in an oil bath for overnight at 85° C.; followed by another 3 h at 120° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain compound 68 as orange solids (190 mg, 57% yield). $^1$H NMR (400 MHz, DMSO-d$_6$) δ 12.46 (br, 1H), 9.24 (br, 1H), 8.06 (br, 1H), 7.30 (m, 1H), 7.21 (m, 3H), 7.10 (m, 2H), 7.02 (m, 1H), 6.40 (m, 2H), 5.08 (br, 1H), 3.83 (s, 3H), 3.78 (s, 1H), 3.73 (m, 2H), 3.75 (m, 2H), 2.34 (m, 1H), 1.95-1.75 (m, 3H); ESI-MS: calcd for (C$_{25}$H$_{25}$FN$_6$O$_2$) 460, found 461 (MH$^+$).

Example 69

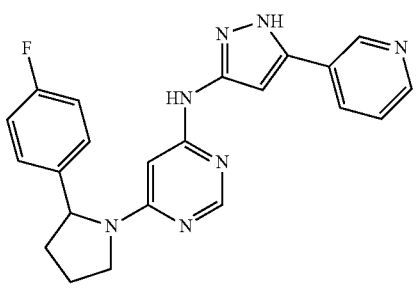

69

A 5 mL microwave mixture vessel equipped with a stir bar was charged with 4-chloro-6-(2-(4-fluorophenyl)pyrrolidin-1-yl)pyrimidine compound 6 (0.100 mg, 0.360 mmol), 5-(pyridin-3-yl)-1H-pyrazol-3-amine (63.44 mg, 0.396 mmol) and HCl in 1,4-dioxane (4.00 M, 0.10 mL, 0.396 mmol) in N-methylpyrrolidone (3 mL). The mixture was heated to 200° C. for 30 minutes in a Biotage Microwave Initiator reactor, then cooled to ambient temperature. The mixture was slowly added to half-saturated NaHCO$_3$ solution in water (~50 mL). Precipitation of solid was observed. The solid was then filtered off and dried. The resulting crude solid was then purified by flash column chromatography on silica gel using 0-5% MeOH in DCM (v/v) as eluent to obtain compound 69 as brown solids (20 mg, 14%). $^1$H NMR (400 MHz, DMSO-d$_6$) δ 12.84 (br, 1H), 9.29 (br, 1H), 8.93 (br, 1H), 8.93 (br, 1H), 8.08 (br, 2H), 7.47 (br, 1H), 7.10 (m, 4H), 6.63 (br, 1H), 5.04 (br, 1H), 3.74 (m, 2H), 2.33 (m, 1H), 1.95-1.75 (m, 3H); ESI-MS: calcd for (C$_{22}$H$_{20}$FN$_7$) 401, found 402 (MH$^+$).

Example 70

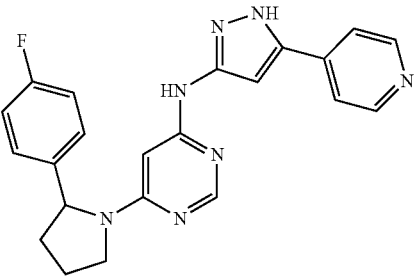

70

A 5 mL microwave mixture vessel equipped with a stir bar was charged with 4-chloro-6-(2-(4-fluorophenyl)pyrrolidin-1-yl)pyrimidine compound 6 (0.200 mg, 0.720 mmol), 5-(pyridin-4-yl)-1H-pyrazol-3-amine (126.89 mg, 0.792 mmol) and HCl in 1,4-dioxane (4.00 M, 0.19 mL, 0.792 mmol) in N-methylpyrrolidone (3.5 mL). The mixture was heated to 200° C. for 30 minutes in a Biotage Microwave Initiator reactor, then cooled to ambient temperature. The mixture was slowly added to half-saturated NaHCO$_3$ solution in water (~50 mL). Precipitation of solid was observed. The solid was then filtered off and dried. The resulting crude solid was then purified by flash column chromatography on silica gel using 0-5% MeOH in DCM (v/v) as eluent to obtain compound 70 as orange solids (38 mg, 13%). $^1$H NMR (400 MHz, DMSO-d$_6$) δ 13.02 (br, 1H), 9.34 (br, 1H), 8.61 (br, 2H), 8.08 (br, 1H), 7.67 (s, 2H), 7.20 (m, 4H), 6.76 (br, 1H), 6.35 (br, 1H), 5.02 (br, 1H), 3.74 (m, 2H), 2.33 (m, 1H), 1.95-1.75 (m, 3H); ESI-MS: calcd for (C$_{22}$H$_{20}$FN$_7$) 401, found 402 (MH$^+$).

Example 71

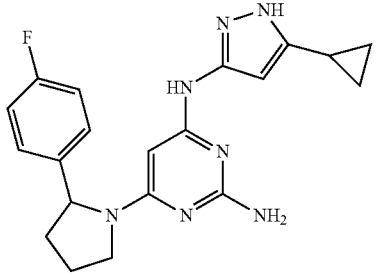

71

A mixture compound 22 (307 mg, 1.05 mmol), compound 17 (270 mg, 1.21 mmol), palladium(II) acetate (35 mg, 0.16 mmol), xantphos (4,5-diphenylphosphanyl-9,9'-dimethyl-9-H-xanthene, 152 mg, 0.28 mmol) and K$_2$CO$_3$ (725 mg, 5.25 mmol) in 1,4-dioxane (12 ml) was purged with argon for 30 min. The mixture was stirred at 80° C. for overnight, then heated with Biotage microwave initiator at 120° C. for overnight. TLC was checked and the starting material was consumed. The reaction mixture was filtered through a pad of celite, washed with DCM/MeOH (10/1) and concentrated. The crude product was purified by column chromatography (silica gel, 0-10% MeOH in DCM) to give compound 71 as yellow solids (58 mg, 6.5% yield). $^1$H NMR (400 MHz, DMSO-d$_6$) δ 12.40-11.80 (br, 1H), 9.20-8.60 (br, 1H), 7.20-7.00 (m, 4H), 6.40-4.80 (br, m, 5H), 3.80-3.40 (m, 2H), 2.30 (m, 1H), 1.80-1.60 (m, 4H), 0.89 (m, 2H), 0.64 (m, 2H); ESI-MS: calcd for (C$_{20}$H$_{22}$FN$_7$) 379, found 380 (MH$^+$).

Example 72

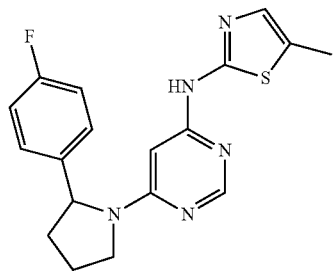

72

A mixture of 4-chloro-6-(2-(4-fluorophenyl)pyrrolidin-1-yl)pyrimidine compound 6 (200 mg, 0.720 mmol), 5-methylthiazol-2-amine (102.77 mg, 0.900 mmol), xantphos (4,5-diphenylphosphanyl-9,9'-dimethyl-9-H-xanthene, 104.17 mg, 0.180 mmol), K$_2$CO$_3$ (497.63 mg, 3.60 mmol) and palladium(II) acetate (24.25 mg, 0.108 mmol) in 1,4-dioxane (10 ml) was purged with argon for 1 hour. The mixture was heated in an oil bath for overnight at 85° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain compound 72 as white solids (66 mg, 26% yield). $^1$H NMR (400 MHz, DMSO-d$_6$) δ 10.81 (br, 1H), 8.20 (br, 1H), 7.20 (m, 4H), 6.60 (s, 1H), 5.86 (br, 1H), 4.96 (br, 1H), 3.75 (m, 2H), 2.36 (m, 1H), 2.28 (s, 3H), 1.95-1.75 (m, 3H); ESI-MS: calcd for (C$_{18}$H$_{18}$FN$_5$S) 355, found 356 (MH$^+$).

Example 73

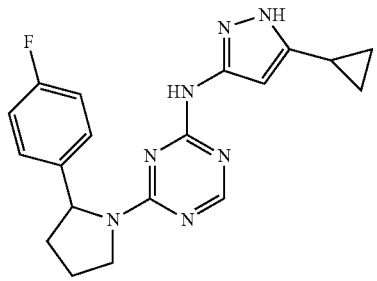

73

The solution of compound 23 (200 mg, 0.85 mmol), 2-(4-Fluorophenyl)pyrrolidine (147 mg, 0.89 mmol) and DIPEA (0.18 ml, 1.06 mmol) in DMSO (2 mL) was stirred at 85° C. for 5 h. The reaction mixture was added to half-saturated ammonium chloride in water (80 mL) and stirred for 30 min. The solids were collected by filtration, washed by water, air-dried to give compound 73 as yellow solids (318 mg, 100% yield). (TLC was one spot and no further purification was performed). $^1$H NMR (400 MHz, DMSO-d$_6$) δ 11.88 (br, 1H), 9.70 (br, 1H), 8.18 (s, 1H), 7.15 (m, 4H), 5.56 (br, 1H), 5.26 (m, 1H), 3.80 (m, 1H), 3.67 (m, 1H), 2.33 (m, 1H), 2.10-1.70 (m, 4H), 0.87 (m, 2H), 0.63 (m, 2H); ESI-MS: calcd for (C$_{19}$H$_{20}$FN$_7$) 365, found 366 (MH$^+$).

Example 74

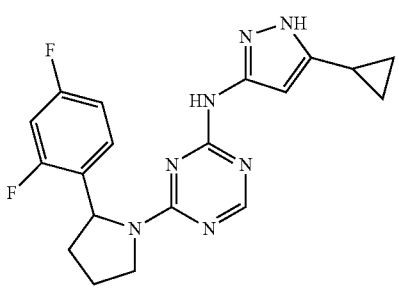

74

The solution of compound 23 (150 mg, 0.63 mmol), 2-(2,4-difluorophenyl)pyrrolidine (127 mg, 0.70 mmol) and DIPEA (0.14 ml, 0.79 mmol) DMSO (2 mL) was stirred at 90° C. for overnight. The reaction mixture was added to half-saturated ammonium chloride in water (75 mL) and stirred for 30 min and then cooled with ice bath. The solids were collected by filtration, washed by water, air-dried. The crude product was purified on column (10-80% EtOAc in DCM) to give compound 74 as yellow solids (63 mg, 26% yield). $^1$H NMR (400 MHz, DMSO-d$_6$) δ 11.88 (br, 1H), 9.60 (br, 1H), 8.19 (s, 1H), 7.30-6.80 (m, 3H), 5.59 (br, 1H), 5.37 (m, 1H), 3.84 (m, 1H), 3.67 (m, 1H), 2.38 (m, 1H), 2.10-1.70 (m, 4H), 0.90 (m, 2H), 0.70-0.60 (m, 2H); ESI-MS: calcd for (C$_{19}$H$_{19}$F$_2$N$_7$) 383, found 384 (MH$^+$).

Example 75

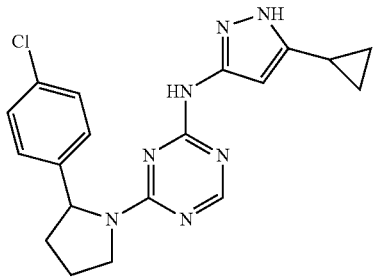

The solution of compound 23 (150 mg, 0.63 mmol), 2-(4-Chlorophenyl)pyrrolidine (121 mg, 0.67 mmol) and DIPEA (0.14 ml, 0.79 mmol) DMSO (2 mL) was stirred at 90° C. for overnight. The reaction mixture was added to half-saturated ammonium chloride in water (75 mL) and stirred for 30 min and then cooled with ice bath. The solids were collected by filtration, washed by water, air-dried. The crude triturated with DCM and the solids were collected by filtration to give the product compound 75 as yellow solids (146 mg, 60% yield). $^1$H NMR (400 MHz, DMSO-$d_6$) δ 11.85 (br, 1H), 9.60 (br, 1H), 8.18 (s, 1H), 7.30-6.80 (m, 4H), 5.54 (br, 1H), 5.24 (m, 1H), 3.80 (m, 1H), 3.67 (m, 1H), 2.37 (m, 1H), 2.10-1.60 (m, 4H), 0.88 (m, 2H), 0.70-0.60 (m, 2H); ESI-MS: calcd for ($C_{19}H_{20}ClN_7$) 381, found 382 (MH$^+$).

Example 76

The KinaseProfiler™ Service Assay Protocols (Millipore) were used to test the kinase inhibiting activity of novel compounds from this invention. To do this, the buffer composition was as follows: 20 mM MOPS, 1 mM EDTA, 0.01% Brij-35, 5% Glycerol, 0.1% β-mercaptoethanol, 1 mg/mL BSA. Test compounds were initially dissolved in DMSO at the desired concentration, then serially diluted into the kinase assay buffer. In a final reaction volume of 25 μL, TrkA(h) (5-10 mU) is incubated with 8 mM MOPS pH 7.0, 0.2 mM EDTA, 200 μM LRRASLG (Kemptide), 10 mM MgAcetate and [γ$^{33}$P-ATP]. The reaction was initiated by the addition of the MgATP mix. After incubation for 40 minute at room temperature, the reaction was stopped by addition of 5 μL of a 3% phosphoric acid solution. 10 μL of the reaction was then spotted onto a P30 filtermat and washed three times for 5 minutes in 50 mM phosphoric acid and once in methanol prior to drying and scintillation counting. Wells containing substrate but no kinase and wells containing a phosphopeptide control were used to set 0% and 100% phosphorylation value, respectively.

A number of studies were performed to analyze the consequences of TrkA kinase inhibition in cell lines. KM12 cells (human colorectal adenocarcinoma, 2000 cells/36□l/well) are seeded into 384-well microplates, which are then placed in a humidified $CO_2$ incubator at 37° C. overnight. The next day, 4□l/well of 10× concentrated drug is added and the plates are returned to the incubator for 72 hr. After 72 hr incubation, plates are removed and 8□l/well CellTi-terBlue (Promega) viability reagent is added. Plates are returned to the incubator for 3 hr, after which fluorescence measurements are read on the Victor X3 plate reader (Perkin Elmer). Data are analyzed using Excel (Microsoft), and $GI_{50}$ values are determined using Prism (Graphpad).

Table 1 shows representative data for the inhibition of Trk kinases by the compounds of this invention at a concentration of 1 μM. Table 1 also shows representative GI50 data for the inhibition of KM-12 cancer cell lines.

TABLE 1

| Example Number | % Inhibition @ 1 μM (TrkA(h)) | GI50 (nM), Km-12 cell line |
|---|---|---|
| 24 | 101 | 122 |
| 25 | 100 | 155 |
| 26 | 98 | 119 |
| 27 | 101 | 100 |
| 28 | 103 | 78 |
| 29 | 105 | 108 |
| 30 | 97 | >500 |
| 31 | 61 | >500 |
| 32 | 91 | >500 |
| 33 | 103 | 434 |
| 34 | 101 | >500 |
| 35 | 92 | 320 |
| 36 | 93 | 107 |
| 37 | 101 | >500 |
| 38 | 95 | 420 |
| 39 | 97 | 39 |
| 40 | 102 | 353 |
| 41 | 101 | >500 |
| 42 | 101 | 26 |
| 43 | 105 | 36 |
| 44 | 103 | 194 |
| 45 | 96 | >500 |
| 46 | 100 | >500 |
| 47 | -6 | >500 |
| 48 | 51 | >500 |
| 49 | 101 | 31 |
| 50 | 99 | 81 |
| 51 | 79 | 578 |
| 52 | 30 | >500 |
| 53 | 96 | 208 |
| 54 | 70 | >500 |
| 55 | 6 | >500 |
| 56 | 47 | >500 |
| 57 | 44 | >500 |
| 58 | 7 | >500 |
| 59 | 0 | >500 |
| 60 | 79 | >500 |
| 61 | -12 | >500 |
| 62 | 105 | >500 |
| 63 | 99 | 207 |
| 64 | 85 | >500 |
| 65 | 79 | 339 |
| 66 | 95 | 372 |
| 67 | 99 | 123 |
| 71 | 100 | 46 |
| 73 | 100 | 22 |
| 74 | 100 | 15 |
| 75 | 100 | 31 |

What is claimed is:
1. A compound of the formula:

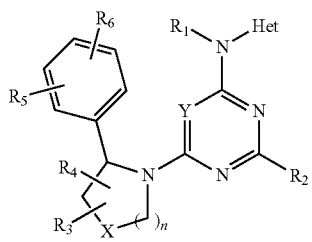

or a pharmaceutically acceptable salt thereof, wherein:

R$_1$ is selected from the group consisting of hydrogen, and C$_1$-C$_4$ alkyl;

R$_2$ is selected from the group consisting of hydrogen, NH$_2$ and C$_1$-C$_4$ alkyl;

R$_3$ and R$_4$ are independently selected from the group consisting of hydrogen, F, CN, oxo, C$_1$-C$_4$ alkyl, cycloalkyl, C$_1$-C$_6$ alkoxy, C$_2$-C$_4$ alkenyl, and C$_2$-C$_4$ alkynyl;

R$_5$ and R$_6$ are independently selected from the group consisting of hydrogen, F, Cl, Br, I, CN, C$_1$-C$_4$ alkyl, C$_1$-C$_6$ alkoxy, C$_2$-C$_6$ alkenyl, CF$_3$, CF$_2$H, CFH$_2$, C$_2$-C$_6$ alkynyl, and CON(R$_7$)R$_8$;

R$_7$ and R$_8$ are independently selected from the group consisting of hydrogen, C$_1$-C$_4$ alkyl, C$_2$-C$_6$ alkenyl, C$_2$-C$_6$ alkynyl, C$_1$-C$_6$ alkoxy, C$_1$-C$_6$alkylthio, C$_2$-C$_6$ alkanoyl, C$_1$-C$_6$alkoxycarbonyl, and C$_2$-C$_6$ alkanoyloxy;

n=0-3;

X is selected from the group consisting of CH$_2$, NR, O or S, R represents hydrogen, C$_1$-C$_4$ alkyl, cycloalkyl, C$_1$-C$_6$ alkoxy, C$_2$-C$_4$ alkenyl, and C$_2$-C$_4$ alkynyl; and Y is selected from the group consisting of N and CR$_9$, wherein R$_9$ is selected from the group consisting of hydrogen, F, Cl, Br, I, CN, NO$_2$, C$_1$-C$_4$ alkyl, C$_1$-C$_6$ alkoxy, C$_2$-C$_6$ alkenyl, CF$_3$, CF$_2$H, CFH$_2$, C$_2$-C$_6$ alkynyl, N(R$_7$)R$_8$, and CON(R$_7$)R$_8$;

Het represents C$_2$-C$_8$ heteroaryl, which is substituted with from 0 to 4 substituents independently chosen from:

(1) halogen, hydroxy, amino, amide, cyano, —COOH, —SO$_2$NH$_2$, oxo, nitro and alkoxycarbonyl;

(2) CON(R$_7$)R$_8$, N(R$_7$)R$_8$; and (3) C$_1$-C$_6$ alkyl, C$_2$-C$_6$ alkenyl, C$_2$-C$_6$ alkynyl, C$_3$-C$_{10}$ aryl or heteroaryl, C$_3$-C$_4$ cycloalkyl, (C$_3$-C$_7$ cycloalkyl)C$_1$-C$_4$ alkyl, C$_1$-C$_6$haloalkyl, C$_1$-C$_6$ alkoxy, C$_1$-C$_6$alkylthio, C$_2$-C$_6$ alkanoyl, C$_1$-C$_6$alkoxycarbonyl, C$_2$-C$_6$ alkanoyloxy, mono- and di-(C$_3$-C$_8$ cycloalkyl)aminoC$_0$-C$_4$alkyl, (4- to 7-membered heterocycle)C$_0$-C$_4$alkyl, C$_1$-C$_6$ alkylsulfonyl, mono- and di-(C$_1$-C$_6$ alkyl) sulfonamido, and mono- and di-(C$_1$-C$_6$ alkyl)aminocarbonyl, each of which is substituted with from 0 to 4 substituents independently chosen from halogen, hydroxy, cyano, amino, —OCH$_3$, —COOH and oxo, with the proviso that when —OCH$_3$ is selected, the Het substituent is a C$_6$ aryl, and the compound is selected from the group consisting of:

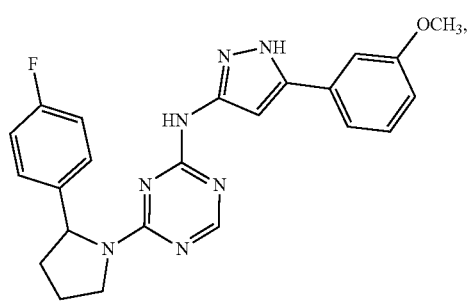

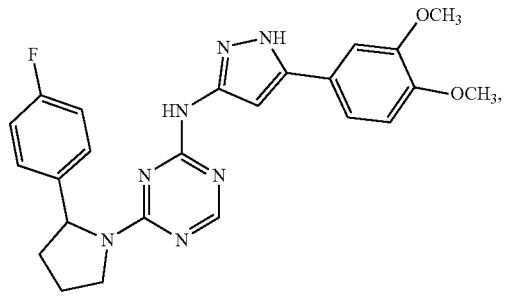

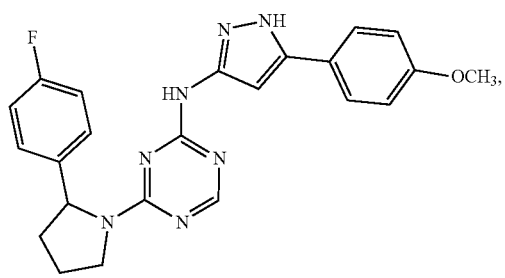

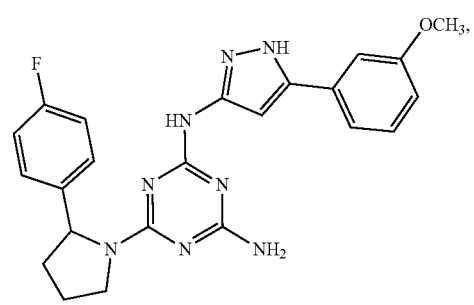

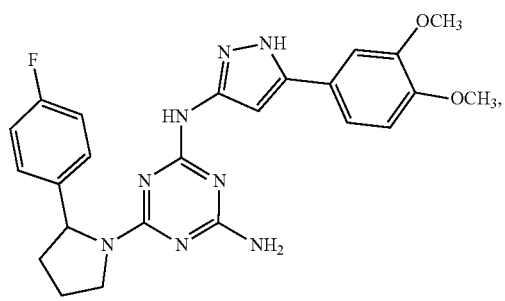

and

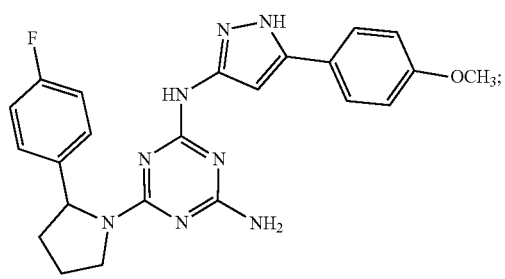

with the proviso that when Het is substituted with C$_3$-C$_4$ cycloalkyl, the compound is selected from the group consisting of:

-continued
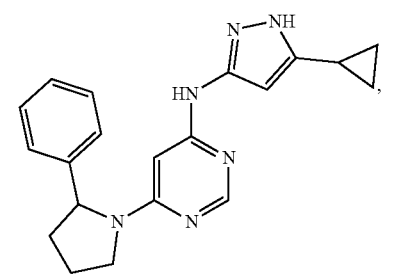
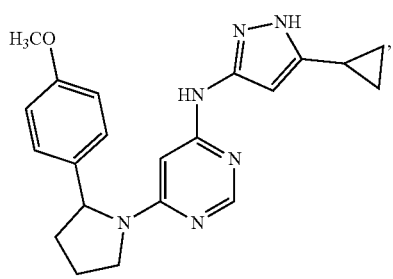
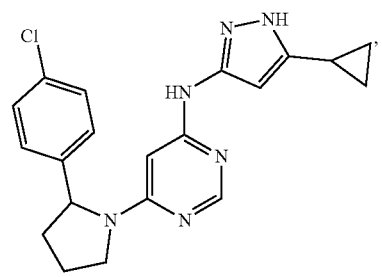
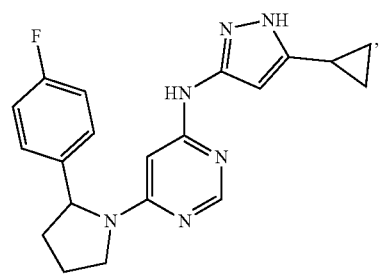
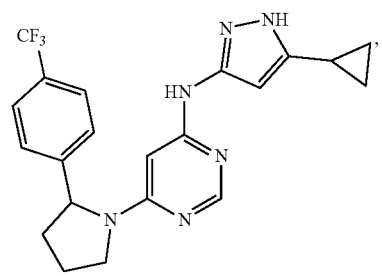
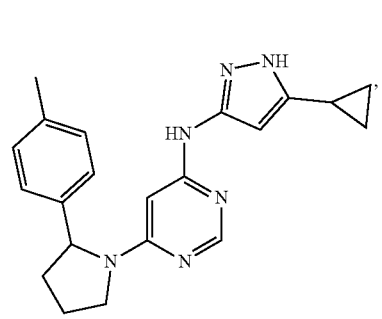
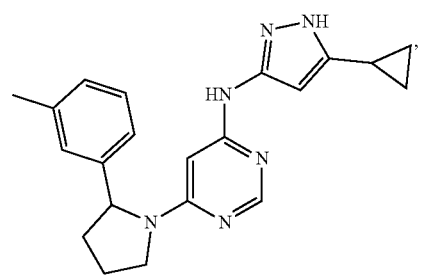
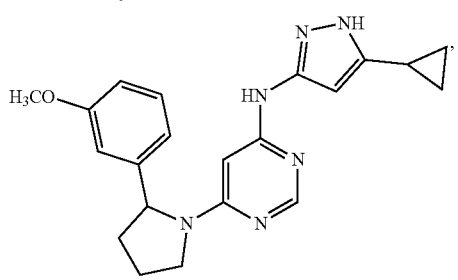
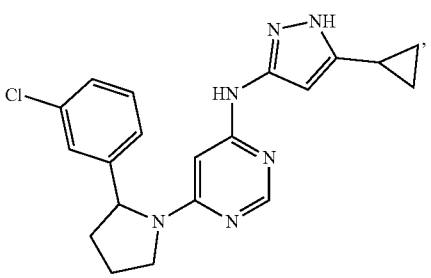
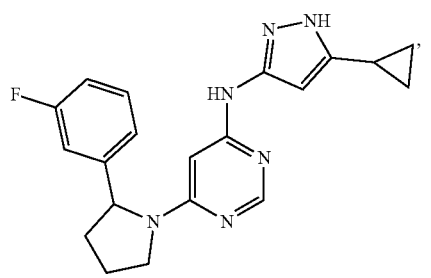
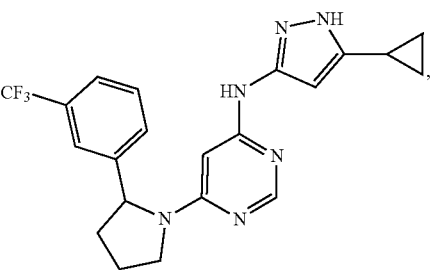
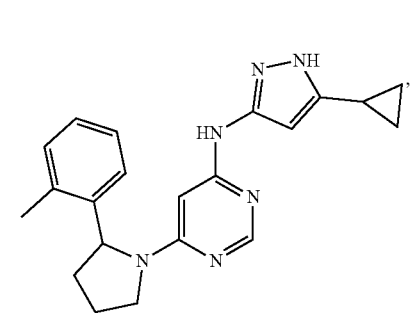

117
-continued
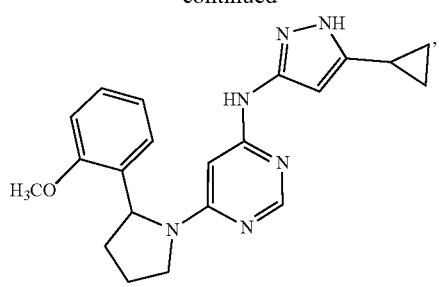
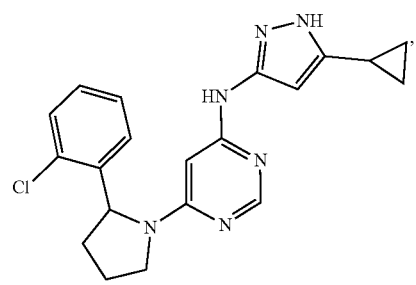
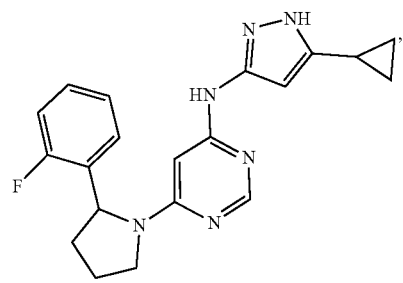
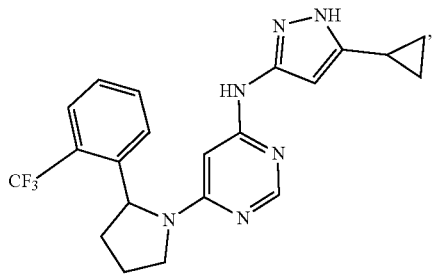
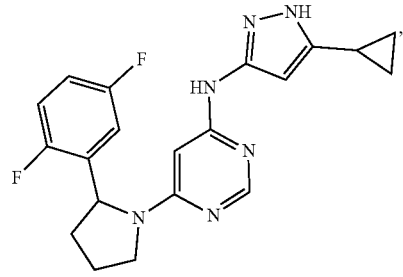
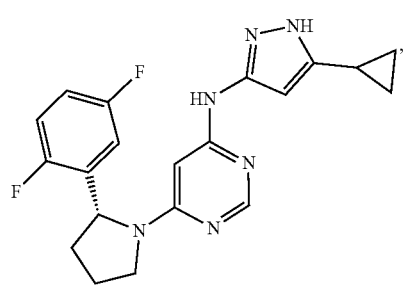
118
-continued
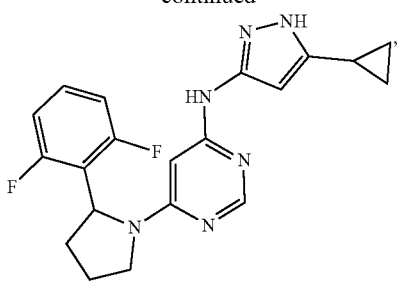
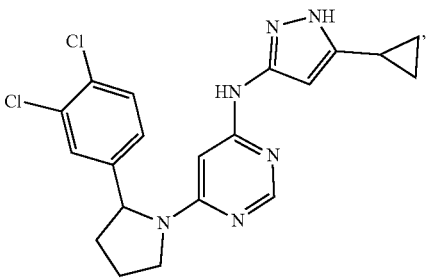
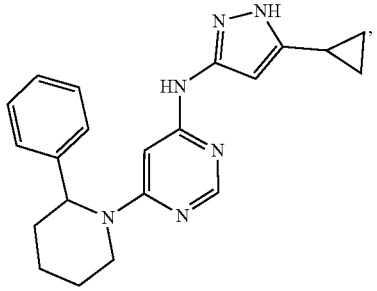
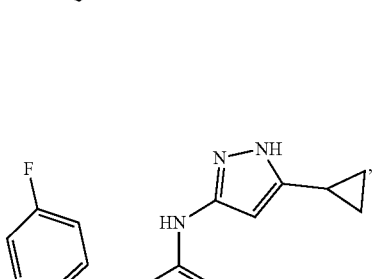
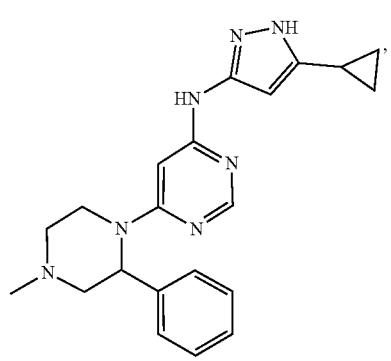

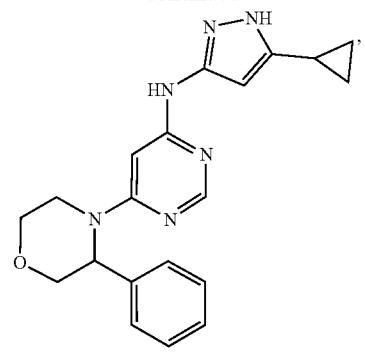
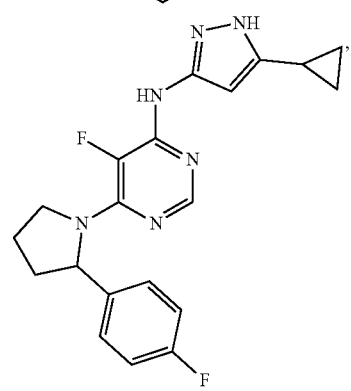
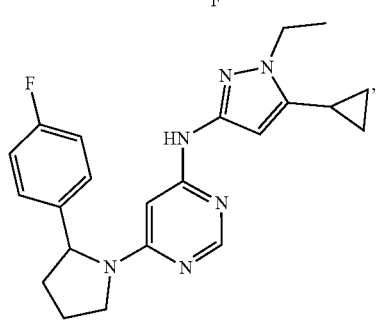
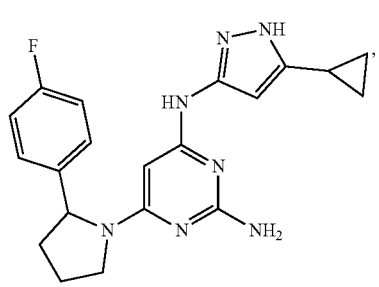
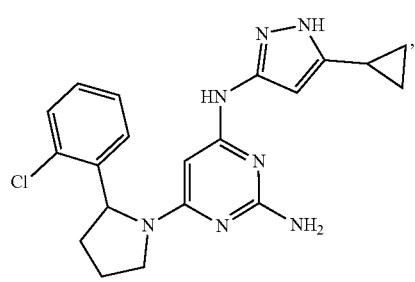
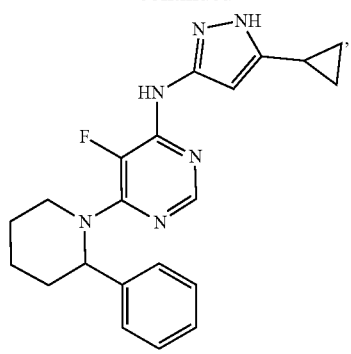
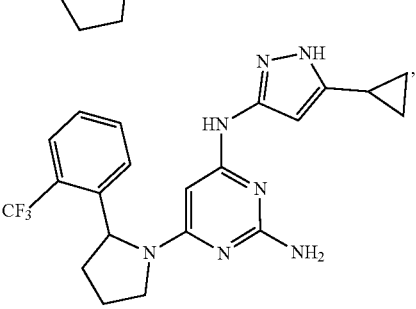
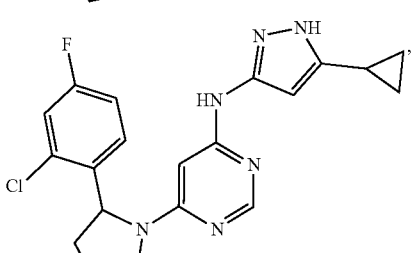
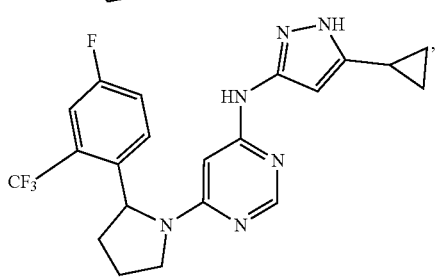

-continued
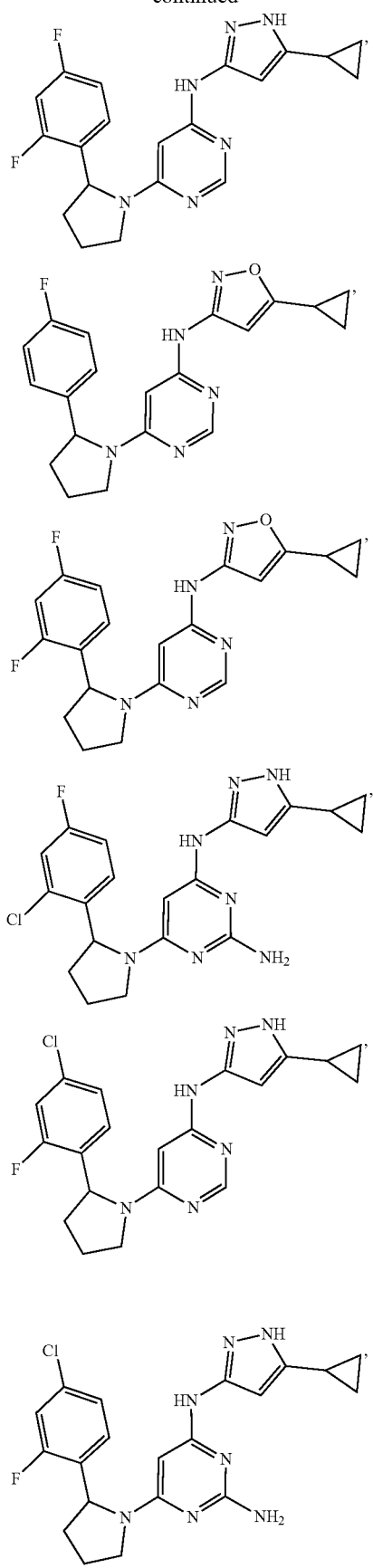
-continued
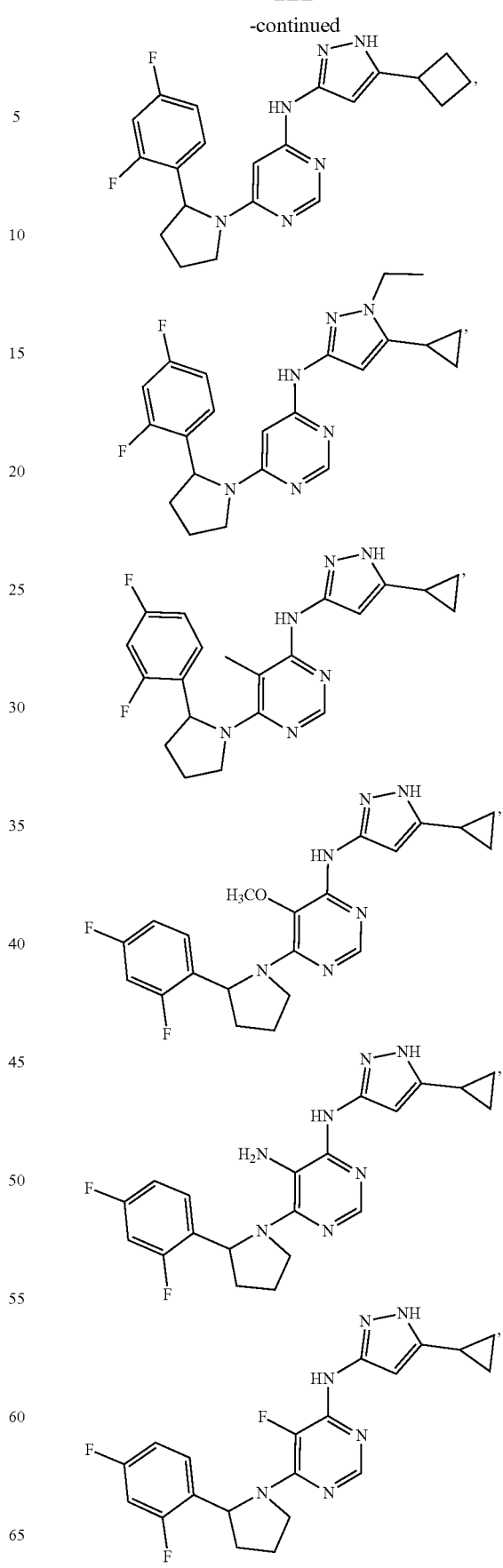

123
-continued
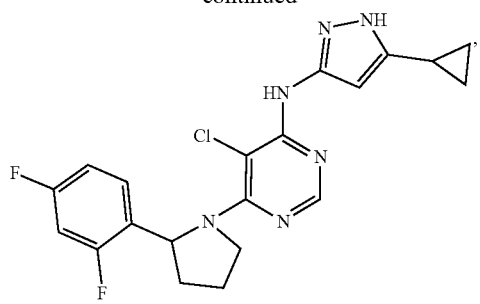
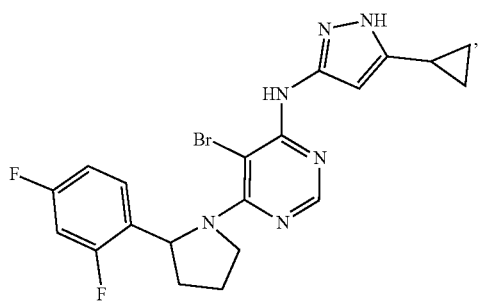
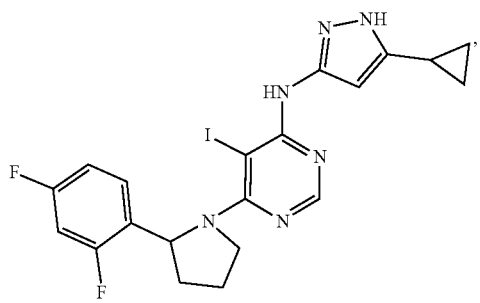
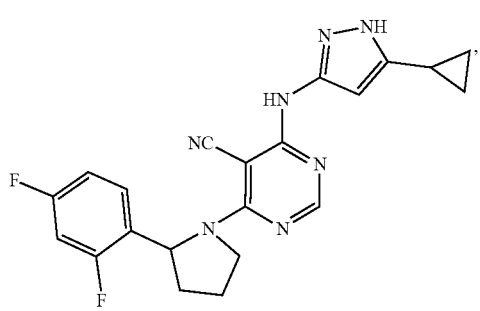
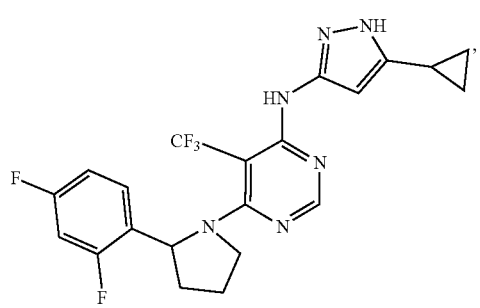
124
-continued
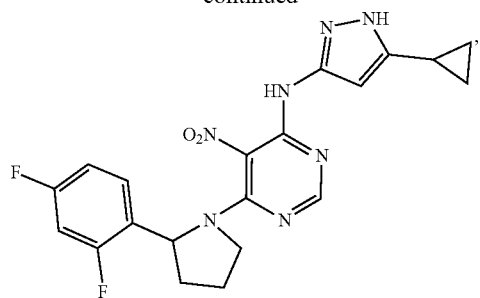
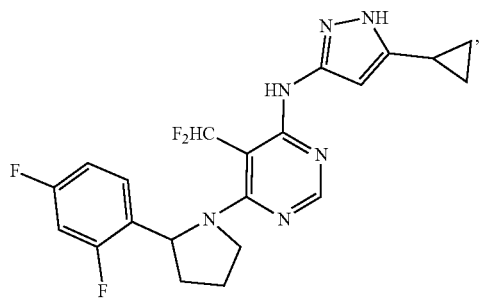
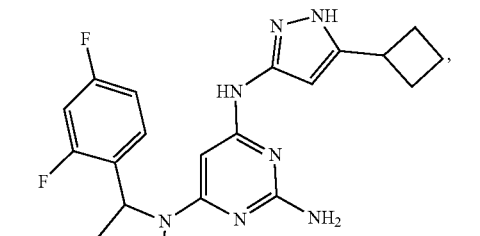
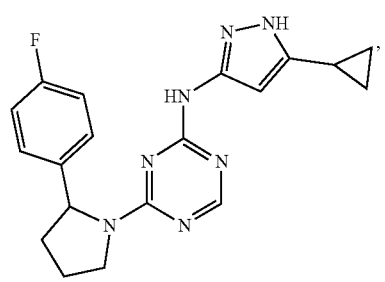
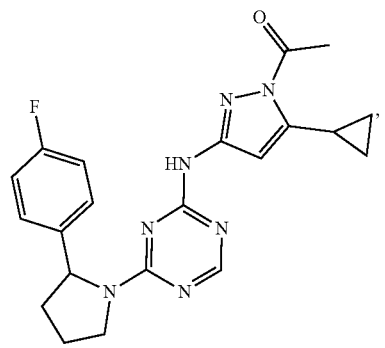

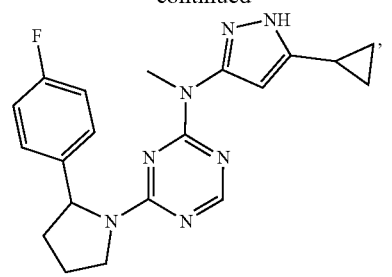
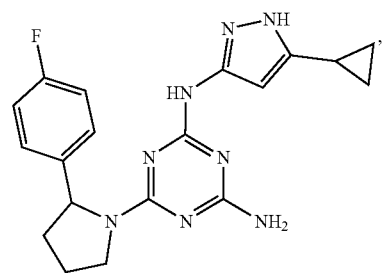
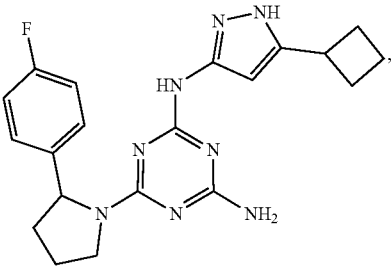
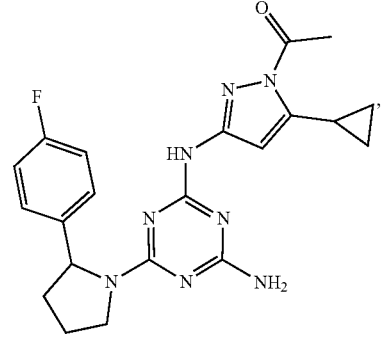
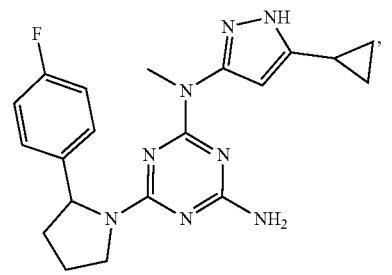
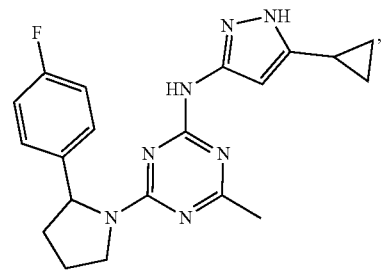
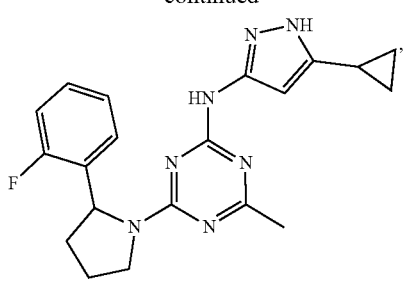
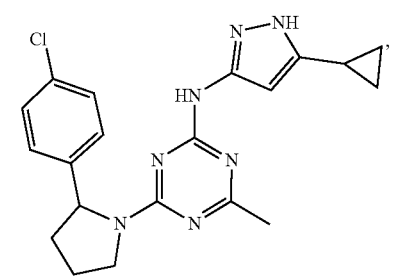
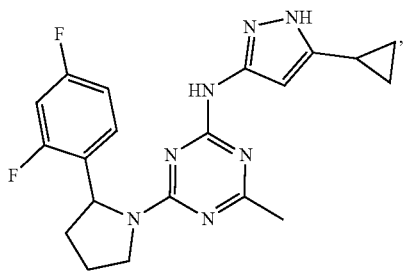
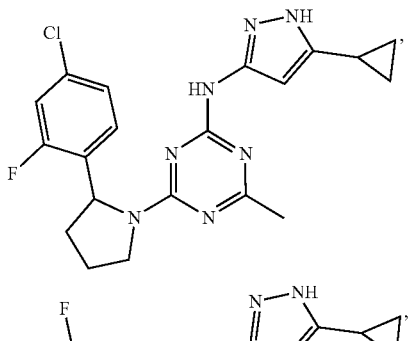
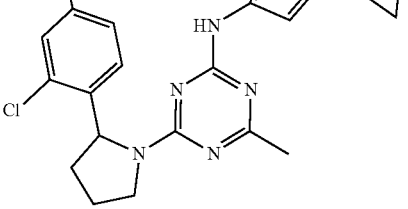
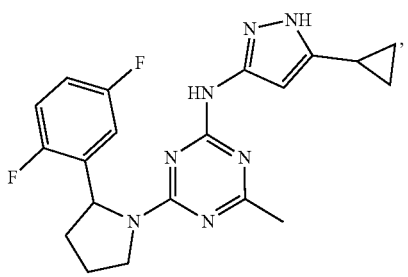

-continued
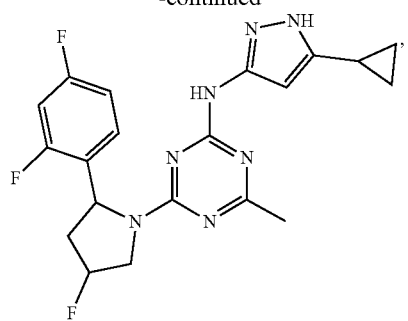
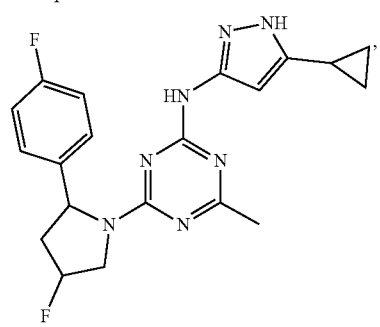
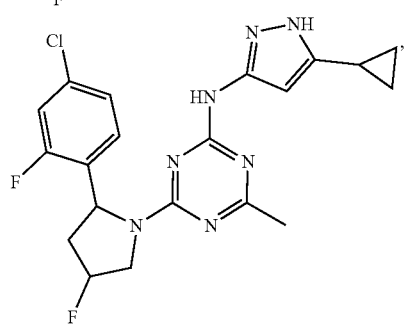
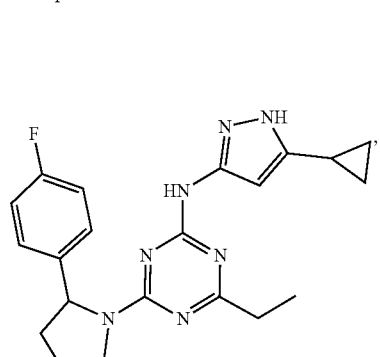
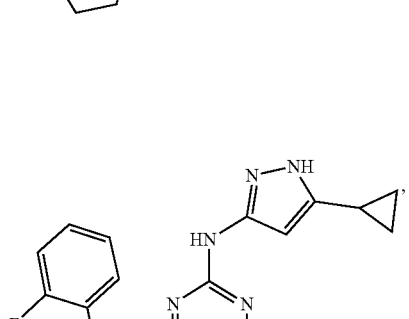
-continued
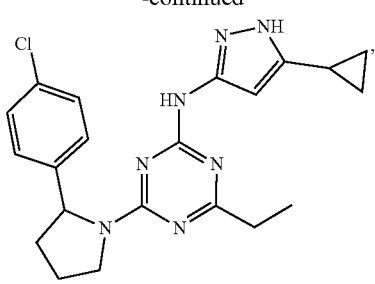
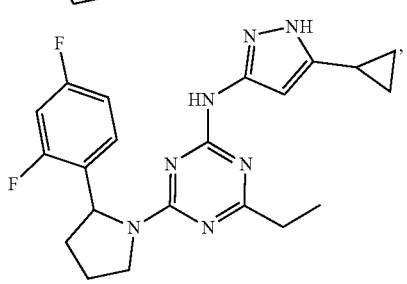
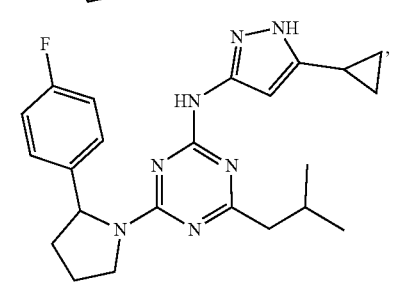
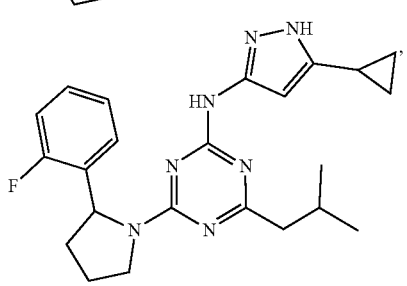
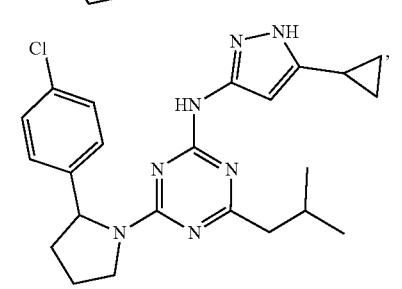
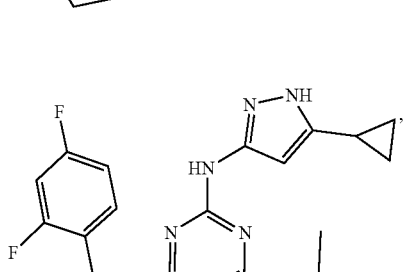

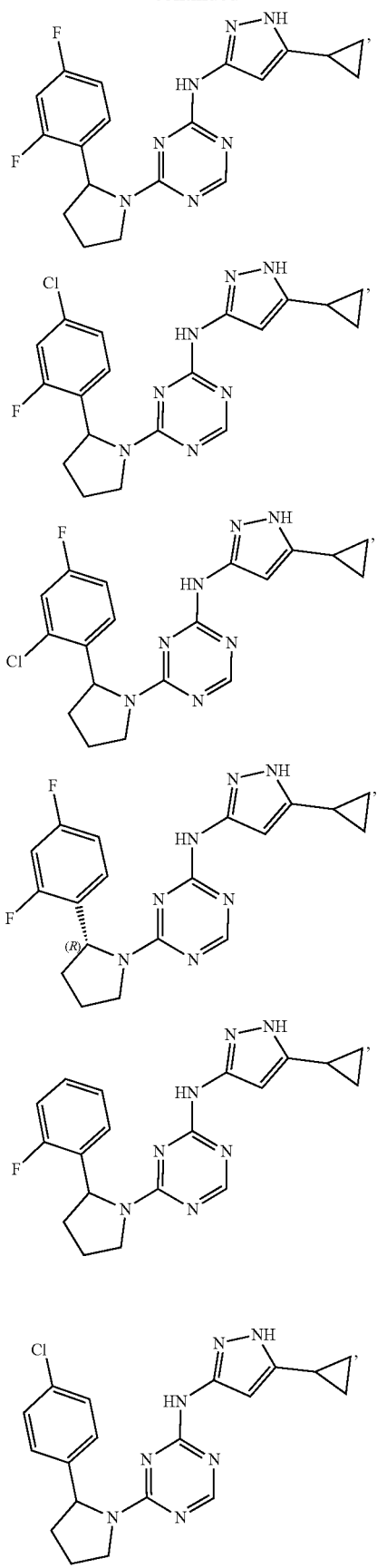
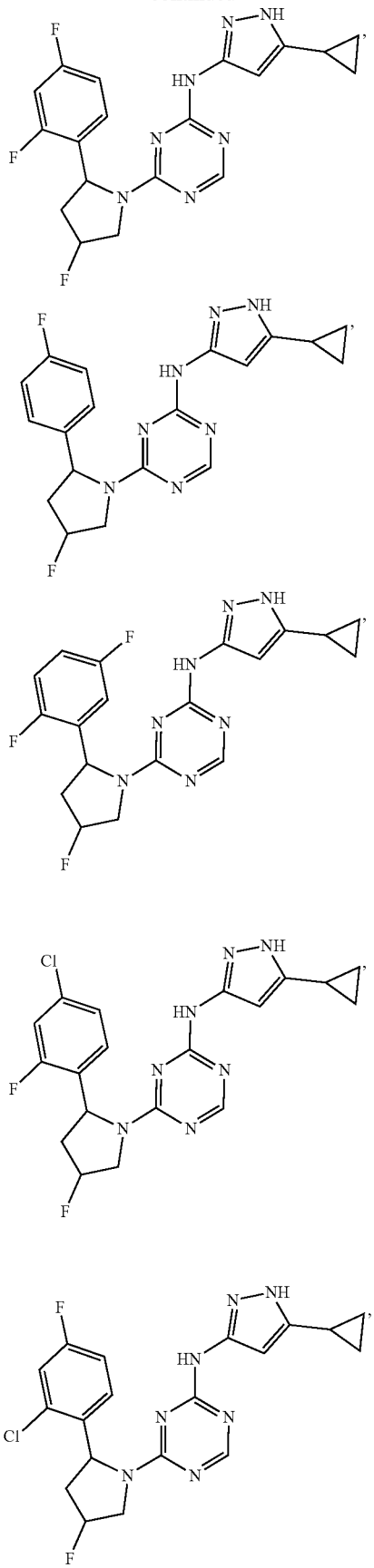

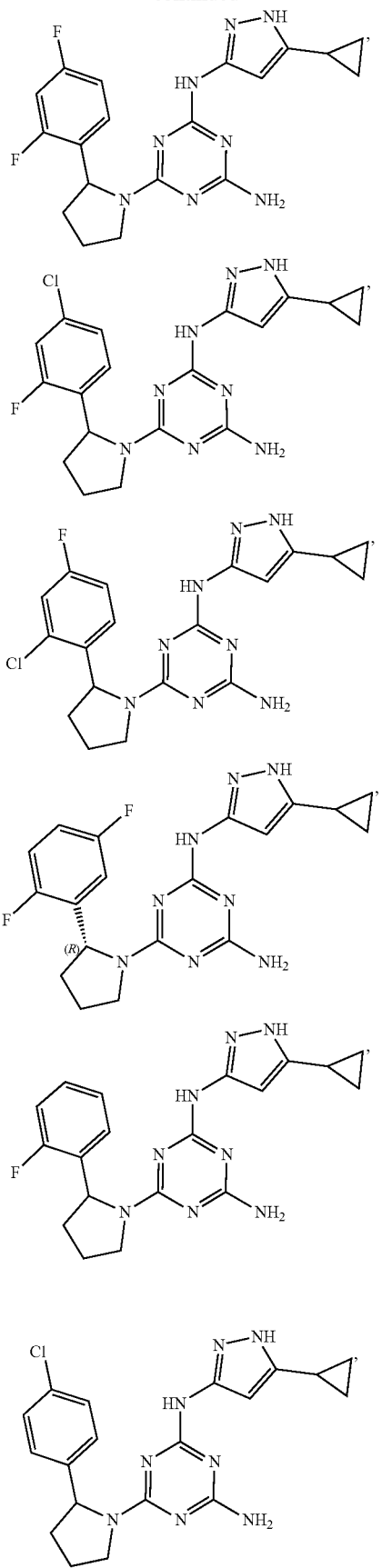
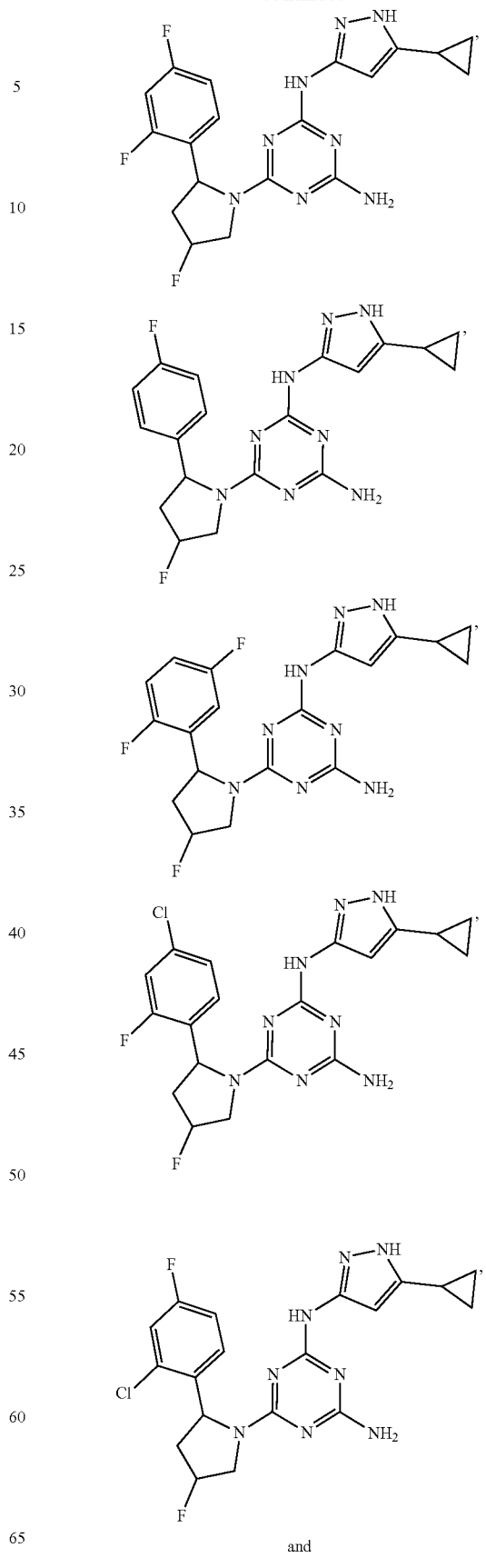
and

-continued

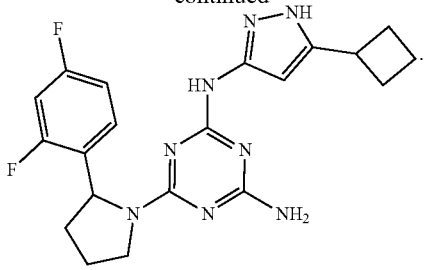

2. A compound of claim 1 with the formula:

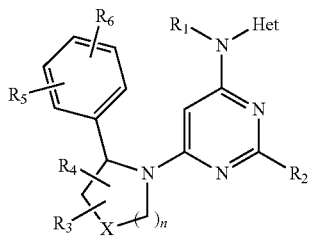

or a pharmaceutically acceptable salt thereof, wherein:
  $R_1$ is selected from the group consisting of hydrogen, and $C_1$-$C_4$ alkyl;
  $R_2$ is selected from the group consisting of hydrogen, $NH_2$, and $C_1$-$C_4$ alkyl;
  $R_3$ and $R_4$ are independently selected from the group consisting of hydrogen, F, CN, oxo, $C_1$-$C_4$ alkyl, cycloalkyl, $C_1$-$C_6$ alkoxy, $C_2$-$C_4$ alkenyl, and $C_2$-$C_4$ alkynyl;
  $R_5$ and $R_6$ are independently selected from the group consisting of hydrogen, F, Cl, Br, I, CN, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, and $CON(R_7)R_8$;
  $R_7$ and $R_8$ are independently selected from the group consisting of hydrogen, $C_1$-$C_4$ alkyl, $C_2$-$C_6$ alkenyl, $C_2$-$C_6$ alkynyl, $C_1$-$C_6$ alkoxy, $C_1$-$C_6$alkylthio, $C_2$-$C_6$ alkanoyl, $C_1$-$C_6$alkoxycarbonyl, and $C_2$-$C_6$ alkanoyloxy;
  n=0-3; and
  X is selected from the group consisting of $CH_2$, NR, O or S, R represents hydrogen, $C_1$-$C_4$alkyl, cycloalkyl, $C_1$-$C_6$ alkoxy, $C_2$-$C_4$ alkenyl, and $C_2$-$C_4$ alkynyl;
  Het represents $C_2$-$C_8$ heteroaryl, which is substituted with from 0 to 4 substituents independently chosen from the group consisting of:
    (1) halogen, hydroxy, amino, amide, cyano, —COOH, —$SO_2NH_2$, oxo, nitro and alkoxycarbonyl;
    (2) $CON(R_7)R_8$, $N(R_7)R_8$; and
    (3) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl)$C_1$-$C_4$ alkyl, $C_1$-$C_6$haloalkyl, $C_1$-$C_6$ alkoxy, $C_1$-$C_6$alkylthio, $C_2$-$C_6$ alkanoyl, $C_1$-$C_6$alkoxycarbonyl, $C_2$-$C_6$ alkanoyloxy, mono- and di-($C_3$-$C_8$ cycloalkyl) amino$C_0$-$C_4$alkyl, (4- to 7-membered heterocycle) $C_0$-$C_4$alkyl, $C_1$-$C_6$ alkylsulfonyl, mono- and di-($C_1$-$C_6$alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

3. A compound of the formula:

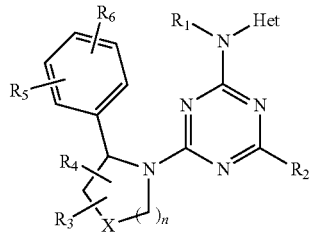

or a pharmaceutically acceptable salt thereof, wherein:
  $R_1$ is selected from the group consisting of hydrogen, and $C_1$-$C_4$ alkyl;
  $R_2$ is selected from the group consisting of hydrogen $NH_2$, and $C_1$-$C_4$ alkyl;
  $R_3$ and $R_4$ are independently selected from the group consisting of hydrogen, F, CN, oxo, $C_1$-$C_4$ alkyl, cycloalkyl, $C_1$-$C_6$ alkoxy, $C_2$-$C_4$ alkenyl, and $C_2$-$C_4$ alkynyl;
  $R_5$ and $R_6$ are independently selected from the group consisting of hydrogen, F, Cl, Br, I, CN, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, and $CON(R_7)R_8$;
  $R_7$ and $R_8$ are independently selected from the group consisting of hydrogen, $C_1$-$C_4$ alkyl, $C_2$-$C_6$ alkenyl, $C_2$-$C_6$ alkynyl, $C_1$-$C_6$ alkoxy, $C_1$-$C_6$alkylthio, $C_2$-$C_6$ alkanoyl, $C_1$-$C_6$alkoxycarbonyl, and $C_2$-$C_6$ alkanoyloxy;
  n=0-3; and
  X is selected from the group consisting of $CH_2$, NR, O or S, R represents hydrogen, $C_1$-$C_4$alkyl, cycloalkyl, $C_1$-$C_6$ alkoxy, $C_2$-$C_4$ alkenyl, and $C_2$-$C_4$ alkynyl;
  Het represents $C_2$-$C_8$ heteroaryl, which is substituted with from 0 to 4 substituents independently chosen from the group consisting of:
    (1) halogen, hydroxy, amino, amide, cyano, —COOH, —$SO_2NH_2$, oxo, nitro and alkoxycarbonyl;
    (2) $CON(R_7)R_8$, $N(R_7)R_8$; and
    (3) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl)$C_1$-$C_4$ alkyl, $C_1$-$C_6$haloalkyl, $C_1$-$C_6$ alkoxy, $C_1$-$C_6$alkylthio, $C_2$-$C_6$ alkanoyl, $C_1$-$C_6$alkoxycarbonyl, $C_2$-$C_6$ alkanoyloxy, mono- and di-($C_3$-$C_8$ cycloalkyl) amino$C_0$-$C_4$alkyl, (4- to 7-membered heterocycle) $C_0$-$C_4$alkyl, $C_1$-$C_6$ alkylsulfonyl, mono- and di-($C_1$-$C_6$alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

4. A compound of claim 1, with the formula:

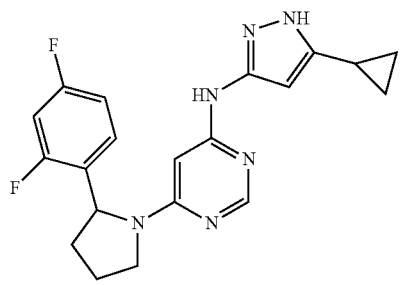 [SMILES: Fc1ccc(C2CCCN2c2cc(Nc3cc(C4CC4)[nH]n3)ncn2)c(F)c1]

or a pharmaceutically acceptable salt thereof.

5. A compound of the formula:
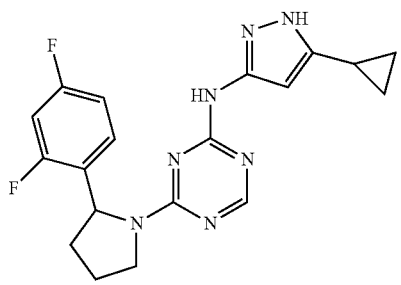
or a pharmaceutically acceptable salt thereof.
6. A compound of claim 1 with the formula
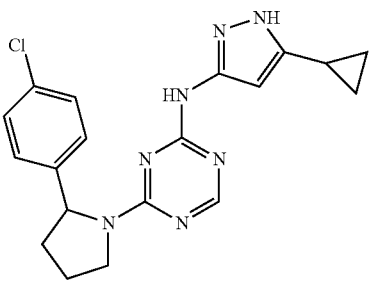 [SMILES: Clc1ccc(C2CCCN2c2ncnc(Nc3cc(C4CC4)[nH]n3)n2)cc1]
or a pharmaceutically acceptable salt thereof.
7. A pharmaceutical composition comprising a compound of claim 1, or a pharmaceutically acceptable salt thereof, and a pharmaceutically acceptable diluent or carrier.
* * * * *